US011649246B2

(12) United States Patent
Park et al.

(10) Patent No.: US 11,649,246 B2
(45) Date of Patent: May 16, 2023

(54) SALTS OF 4-AMINO-N-(L-((3-CHLORO-2-FLUOROPHENYL)AMINO)-6-METHYL-ISOQUINOLIN-5-YL)THIENO[3,2-D]PYRIMIDINE-7-CARBOXAMIDE, AND CRYSTALLINE FORMS THEREOF

(71) Applicant: Hanmi Pharm. Co., Ltd., Hwaseong-si (KR)

(72) Inventors: Chang Hee Park, Hwaseong-si (KR); Seung Hyun Jung, Hwaseong-si (KR); Young Gil Ahn, Hwaseong-si (KR); Kwee Hyun Suh, Hwaseong-si (KR)

(73) Assignee: Hanmi Pharm. Co., Ltd., Seoul (KR)

( * ) Notice: Subject to any disclaimer, the term of this patent is extended or adjusted under 35 U.S.C. 154(b) by 0 days.

(21) Appl. No.: 16/768,535

(22) PCT Filed: Nov. 29, 2018

(86) PCT No.: PCT/KR2018/014968
§ 371 (c)(1),
(2) Date: May 29, 2020

(87) PCT Pub. No.: WO2019/107971
PCT Pub. Date: Jun. 6, 2019

(65) Prior Publication Data
US 2020/0308187 A1  Oct. 1, 2020

Related U.S. Application Data

(60) Provisional application No. 62/592,676, filed on Nov. 30, 2017.

(51) Int. Cl.
| | | |
|---|---|---|
| C07D 495/04 | (2006.01) | |
| A61P 35/00 | (2006.01) | |
| C07C 309/00 | (2006.01) | |
| C07C 309/04 | (2006.01) | |
| C07C 309/30 | (2006.01) | |

(52) U.S. Cl.
CPC ........ C07D 495/04 (2013.01); *C07B 2200/13* (2013.01)

(58) Field of Classification Search
CPC ... C07D 495/04; C07B 2200/13; A61P 35/00; C07C 309/30; C07C 309/04; C07C 309/00
See application file for complete search history.

(56) References Cited

U.S. PATENT DOCUMENTS

| | | | |
|---|---|---|---|
| 7,056,942 B2 | 6/2006 | Hildesheim et al. | |
| 11,261,160 B2* | 3/2022 | Srinivasan | C07D 215/20 |
| 2014/0371219 A1 | 12/2014 | Bae et al. | |
| 2016/0296514 A1 | 10/2016 | Hoelder et al. | |

FOREIGN PATENT DOCUMENTS

| | | |
|---|---|---|
| KR | 10-2011-0044053 A | 4/2011 |
| KR | 10-2011-0055202 A | 5/2011 |
| KR | 10-2011-0089108 A | 8/2011 |
| WO | 2013100632 A1 | 7/2013 |

OTHER PUBLICATIONS

Van de Water, B., "Cellular stress responses and molecular mechanisms of nephrotoxicity." Toxicology letters 162.1 (2006): 83-93.*
Saez-Rodriguez, J., "Modeling signaling networks to advance new cancer therapies." Annual review of biomedical engineering 17 (2015): 143-163.*
Cohen, P., "The development and therapeutic potential of protein kinase inhibitors." Current opinion in chemical biology 3.4 (1999): 459-465.*
Stieger, N. "Recrystallization of active pharmaceutical ingredients." Crystallization-Science and Technology (2012): 183-204.*
Serajuddin, A.T.M. "Salt formation to improve drug solubility." Advanced drug delivery reviews 59.7 (2007): 603-616.*
Berge, S. M., "Pharmaceutical salts." Journal of pharmaceutical sciences 66.1 (1977): 1-19.*
International Search Report and Written Opinion for PCT/KR2018/014968, dated Mar. 8, 2019, 15 pages.
Byrn et al., "Pharmaceutical Solids: A Strategic Approach to Regulatory Considerations", Pharmaceutical Research, Jul. 1, 1995, vol. 12, No. 7, pp. 945-954.
Kawaguchi et al., "Drug and Crystal Polymorphism", Journal of Human Environmental Engineering, 2002, vol. 4, No. 2, pp. 310-317.
Oshima, Hiroshi, "Crystallization of Polymorphs and Pseudo-polymorphs and Its Control", Pharm Stage, Jan. 15, 2027, vol. 6, No. 10, pp. 48-53.
Shirai et al., "Rapid Microwave Drying for Slip Cast Bodies", Journal of the Ceramic Society of Japan, 2006, vol. 114, No. 2, pp. 217-219.
Takada, Noriyuki, "API Form Screening and Selection in Drug Discovery Stage", Pharm Stage, Jan. 14, 2007, vol. 6, No. 10, pp. 20-25.
Yamano, Mitsuhisa, "Approach to Crystal Polymorph in Process Research of New Drug", Journal of Synthetic Organic Chemistry Japan, vol. 65, No. 9, Sep. 1, 2007, pp. 907-913.
European Supplementary Search Report for EP 18 88 2348, dated Mar. 2, 2021, 9 pages.
Bernstein, J., "Crystal growth, polymorphism and structure-property relationships in organic crystals", J. Phys. D. Appl. Phys., 1993, vol. 26, pp. B56-B76.
Cruz-Cabeza et al., "Facts and fictions about polymorphism", Chem. Soc. Rev., 2015, vol. 44, pp. 8619-8635.
Morissette et al., "High-throughput crystallization: polymorphs, salts, co-crystals and solvates of pharmaceutical solids", Advanced Drug Delivery Reviews, 2004, vol. 56, pp. 275-300.

(Continued)

*Primary Examiner* — John M Mauro
(74) *Attorney, Agent, or Firm* — Armstrong Teasdale LLP

(57) ABSTRACT

The present invention relates to a crystalline form of a salt of 4-amino-N-(1-((3-chloro-2-fluorophenyl)amino)-6-methylisoquinolin-5-yl)thieno[3,2-d]pyrimidine-7-carboxamide, and a pharmaceutical composition containing the same. The crystalline form of the salt of the compound can be easily used for preparing a pharmaceutical composition containing the same as an active ingredient.

19 Claims, 35 Drawing Sheets

(56) References Cited

OTHER PUBLICATIONS

Bastin et al, "Salt Selection and Optimization Procedures for Pharmaceutical New Chemical Entities", Organic Process Research a Development, 2000, vol. 4, pp. 427-435.

Brittain, Harry G., Polymorphism in Pharmaceutical Solids, Drugs and The Pharmaceutical Sciences, 192, 2009, Chapter 4, Classical Methods of Preparation of Polymorphs and Alternative Solid Forms, pp. 76-138.

* cited by examiner

DSC Diagram for Formula (I) bis-hydrochloride salt

DVS Isotherm Diagram for Formula (I) bis-hydrochloride salt

PXRD Pattern for Formula (I) bis-methanesulfonate salt

PXRD Pattern for Formula (I) bis-benzenesulfonate salt

PXRD Pattern for Formula (I) bis-hydrobromide salt

DSC Diagram for Formula (I) bis-hydrochloride salt Polymorph Form I

DSC Diagram for Formula (I) bis-hydrochloride salt Polymorph Form I

PXRD Pattern for Formula (I) bis-hydrochloride salt Polymorph Form II

DSC Diagram for Formula (I) bis-hydrochloride salt Polymorph Form II

PXRD Pattern for Formula (I) bis-hydrochloride salt Polymorph Form III

DSC Diagram for Formula (I) bis-hydrochloride salt polymorph Form III

PXRD Pattern for Formula (I) bis-hydrochloride salt Polymorph Form IV

PXRD Pattern Chart for Formula (I) bis-hydrochloride salt Polymorph Form V

PXRD Pattern for Formula (I) bis-hydrochloride salt Polymorph Form VI

DSC Diagram for Formula (I) bis-hydrochloride salt polymorph Form VI

PXRD Pattern for Formula (I) bis-*p*-toluenesulfonate salt Form A Polymorph

PXRD Pattern for Formula (I) bis-*p*-toluenesulfonate salt Form B Polymorph

PXRD Pattern for crystalline Formula (I) bis-ethanesulfonate salt

PXRD Pattern for crystalline Formula (I) free base

PXRD Pattern for amorphous Formula (I) free base

PXRD Pattern for amorphous Formula (I) bis-hydrochloride salt

SALTS OF 4-AMINO-N-(L-((3-CHLORO-2-FLUOROPHENYL)AMINO)-6-METHYL-ISOQUINOLIN-5-YL)THIENO[3,2-D]PYRIMIDINE-7-CARBOXAMIDE, AND CRYSTALLINE FORMS THEREOF

CROSS-REFERENCE TO RELATED APPLICATIONS

This application is a U.S. National Phase Application of PCT/KR2018/014968, filed Nov. 29, 2018, which claims the benefit of priority to U.S. Provisional Application Ser. No. 62/592,676 filed on Nov. 30, 2017, the contents of which are hereby expressly incorporated by reference in their entirety.

TECHNICAL FIELD

The present invention relates to salts of 4-amino-N-(1-((3-chloro-2-fluorophenyl)amino)-6-methylisoquinolin-5-yl)thieno[3,2-d]pyrimidine-7-carboxamide, crystalline forms thereof and pharmaceutical compositions thereof.

BACKGROUND ART

The compound 4-amino-N-(1-((3-chloro-2-fluorophenyl)amino)-6-methylisoquinolin-5-yl)thieno[3,2-d]pyrimidine-7-carboxamide (referred to herein as Formula (I)), is disclosed in PCT application WO 2013/100632. The compound is a pan-RAF inhibitor and has a selective inhibitory activity for RAF, FMS, DDR1 and DDR2 kinases.

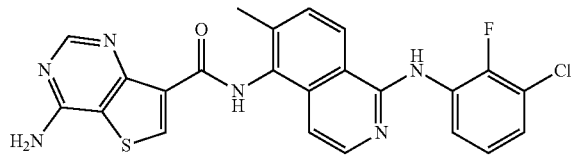

Formula (I)

The compound of Formula (I) prepared in the above cited reference is an amorphous solid. As compared to crystalline forms, amorphous forms are generally less suitable for large-scale production of pharmaceutical drugs and have poor solubility.

Different crystalline forms of pharmaceutical agents can provide different and improved properties with respect to stability, solubility, dissolution rate, hardness, compressibility and melting point, among other physical and mechanical properties.

DISCLOSURE OF INVENTION

Technical Problem

There is a need in the chemical and therapeutic arts for identification of new salts and crystalline forms of Formula (I) having improved physiochemical properties, and methods for reproducibly generating such salts and crystalline forms.

Solution to Problem

The present invention relates to salts and crystalline forms of a pan-RAF inhibitor Formula (I), which has the systematic name 4-amino-N-(1-((3-chloro-2-fluorophenyl)amino)-6-methylisoquinolin-5-yl)thieno[3,2-d]pyrimidine-7-carboxamide, and which can be depicted by the formula:

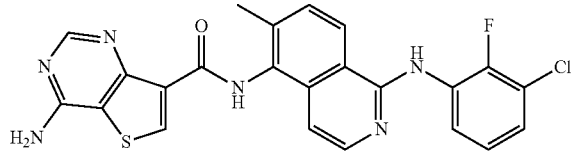

Formula (I)

The compound of Formula (I) is described by chemical structure and chemical name. The chemical structure predominates in the case of any inconsistency between the chemical structure and the chemical name.

In some embodiments, a compound 4-amino-N-(1-((3-chloro-2-fluorophenyl)amino)-6-methylisoquinolin-5-yl)thieno[3,2-d]pyrimidine-7-carboxamide of Formula (I), or a pharmaceutically acceptable salt thereof, in crystalline form is provided.

Formula (I)

In some other embodiments, a salt of Formula (I) is provided, wherein the salt is selected from the group consisting of a hydrochloride salt, a hydrogensulfate salt, a p-toluenesulfonate salt, an ethanesulfonate salt, and a methanesulfonate salt.

In some such embodiments, the salt is selected from group consisting of the bis-hydrochloride salt, the bis-hydrogensulfate salt, the bis-p-toluenesulfonate salt, the bis-ethanesulfonate salt, and the bis-methanesulfonate salt.

In some other embodiments, a crystalline bis-hydrochloride salt polymorph Form I of Formula (I) is provided as follows:

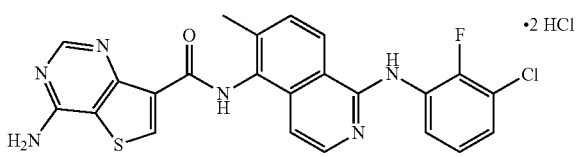

Formula (I)
·2 HCl

The Formula (I) bis-hydrochloride salt polymorph Form I: (a) is a trihydrate; and (b) is characterized by a powder X-ray diffraction pattern having three or more peaks selected from those at diffraction angle 2θ±0.2° values of 5.89°, 7.77°, 8.31°, 11.80°, 16.68°, 23.22°, 23.69°, 26.89°, 27.51°, and 29.53° when irradiated with a Cu-Kα light source.

In some other embodiments, a pharmaceutical composition comprising any of the Formula (I) salts and crystalline forms of the present invention and at least one pharmaceutically acceptable excipient is provided.

In some other embodiments, a method for preventing or treating abnormal cell growth disease in a mammal wherein the abnormal cell growth disease is caused by abnormal activation of a protein kinase is provided. The method comprises administering a pharmaceutical composition comprising any of the Formula (I) salts and crystalline forms of the present invention and at least one pharmaceutically acceptable excipient to the mammal. In some such embodiments, the mammal is a human.

In some other embodiments, a method for preparing a crystalline salt form of Formula (I) is provided. The method comprises the steps of: (a) adding an organic solvent to the free base of the compound of Formula (I) to form an admixture; (b) adding 2 to 3 equivalents of an acid to each equivalent of Formula (I) free base in the admixture obtained in step (a) to form a slurry containing solid Formula (I) crystalline salt; and (c) isolating the solid Formula (I) crystalline salt from the slurry. The acid is selected from the group consisting of hydrochloric acid, sulfuric acid, p-toluenesulfonic acid, ethanesulfonic acid, methanesulfonic acid salt, and mixtures thereof.

In some other embodiments, a method for preparing crystalline bis-hydrochloride polymorph Form I or Form V of Formula (I) is provided. The method comprises: (a) admixing Formula (I) free base with a solvent; (b) adding from about 2 to about 3 equivalents of hydrochloric acid per equivalent of Formula (I) to the admixture to form a slurry comprising solid crystalline Formula (I) bis-hydrochloride; (c) isolating solid crystalline Formula (I) bis-hydrochloride from the slurry; and (d) drying the crystalline Formula (I) bis-hydrochloride. When the solvent is ethanol, the dried crystalline Formula (I) bis-hydrochloride is exposed to air comprising water vapor, and the resulting polymorph is the Form I polymorph. When the solvent is dimethylformamide ("DMF"), the resulting polymorph is the Form V polymorph.

In some other embodiments, a method for preparing crystalline bis-hydrochloride polymorph Form I of Formula (I) is provided. The method comprises: (a) admixing Formula (I) free base with ethanol; (b) adding from about 2 to about 3 equivalents of hydrochloric acid per equivalent of Formula (I) to the admixture to form a slurry comprising solid Formula (I) bis-hydrochloride; (c) isolating solid crystalline Formula (I) bis-hydrochloride from the slurry; and (d) drying the crystalline Formula (I) bis-hydrochloride. The dried crystalline Formula (I) bis-hydrochloride is exposed to air comprising water vapor, and the resulting polymorph is the Form I polymorph.

In some other embodiments, the free base, salt and crystalline forms of Formula (I) include those of: crystalline bis-hydrochloride salt polymorph Form I characterized by a powder X-ray diffraction ("PXRD") pattern in accordance with FIG. 35; crystalline bis-hydrochloride salt polymorph Form II characterized by a PXRD pattern in accordance with FIG. 14; crystalline bis-hydrochloride salt polymorph Form III characterized by a PXRD pattern in accordance with FIG. 17; crystalline bis-hydrochloride salt polymorph Form IV characterized by a PXRD pattern in accordance with FIG. 20; crystalline bis-hydrochloride salt polymorph Form V characterized by a PXRD pattern in accordance with FIG. 21; crystalline bis-hydrochloride salt polymorph Form VI characterized by a PXRD pattern in accordance with FIG. 22; crystalline bis-hydrogensulfate salt polymorph characterized by a PXRD pattern in accordance with FIG. 4; crystalline bis-p-toluenesulfonate salt polymorph Form A characterized by a PXRD pattern in accordance with FIG. 26; crystalline bis-p-toluenesulfonate salt polymorph Form B characterized by a PXRD pattern in accordance with FIG. 27; crystalline bis-ethanesulfonate salt polymorph characterized by a PXRD pattern in accordance with FIG. 28; crystalline bis-methanesulfonate salt polymorph characterized by a PXRD pattern in accordance with FIG. 7; and crystalline free base characterized by a PXRD pattern in accordance with FIG. 29.

Advantageous Effects of Invention

The present invention can provide new salts and crystalline forms of Formula (I) having improved physiochemical properties, and methods for reproducibly generating such salts and crystalline forms.

MODE FOR THE INVENTION

Figure 1:
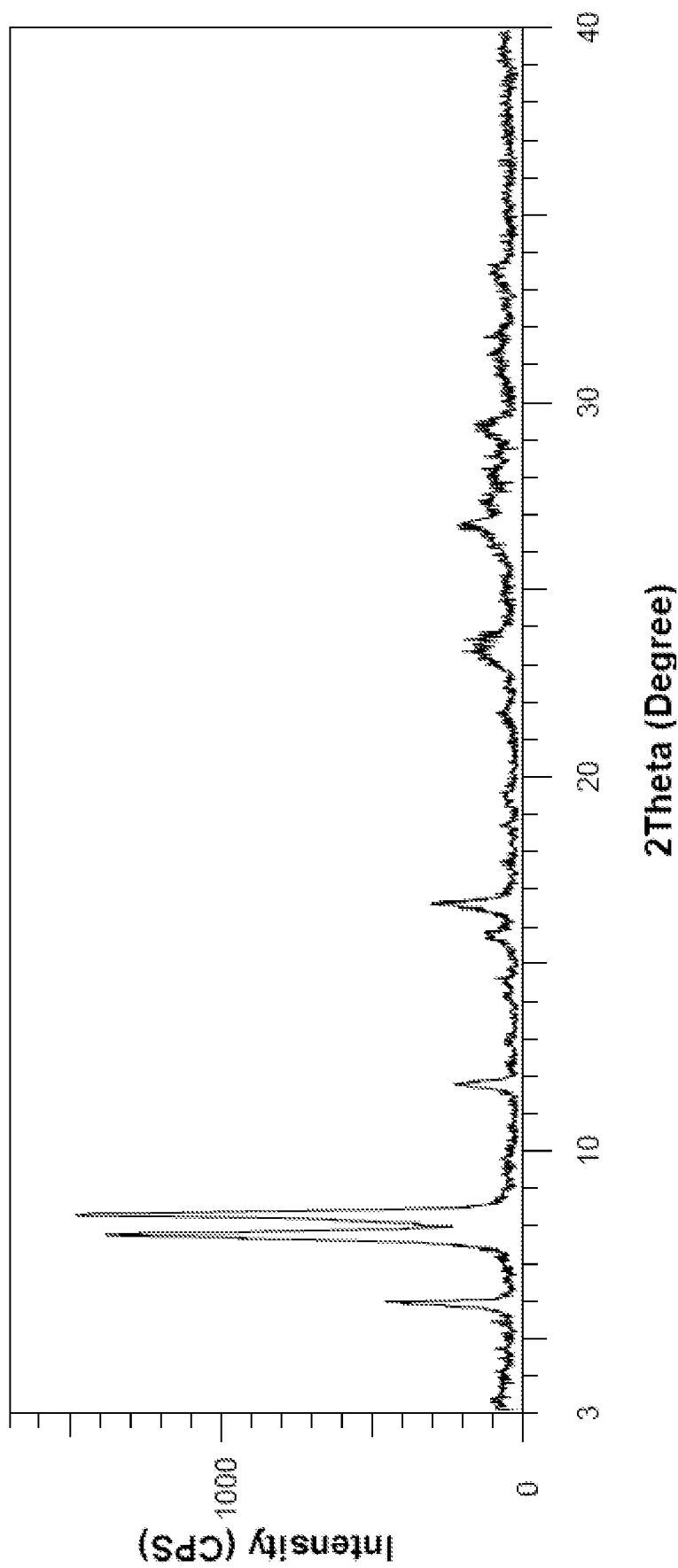
FIG. 1 shows a powder X-ray diffraction ("PXRD") pattern for crystalline Formula (I) bis-hydrochloride salt.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Although methods and materials similar or equivalent to those described herein can be used in the practice or testing of the invention, suitable methods and materials are described below. All publications, patent applications, patents, and other references mentioned herein are incorporated by reference in their entirety.

In accordance with the present invention, it has been discovered that a hydrochloric acid salt, a sulfuric acid salt, a p-toluenesulfonic acid salt, an ethanesulfonic acid salt and a methanesulfonic acid salt of the compound of Formula (I), and crystalline forms thereof, have improved physicochemical characteristics as compared to amorphous forms and free base forms including, for instance, long-term stable maintenance without the requirement of particular storage conditions, and excellent water-solubility.

The present invention provides for crystalline forms of the compound of Formula (I). The present invention still further provides for various crystalline polymorphic forms of salts of the compound Formula (I). The present invention yet further provides for processes for preparing various salt and crystalline polymorphic forms of the compound of Formula (I).

Unless otherwise defined, all terms including technical and scientific terms used herein have the same meaning as commonly understood within the context by one of ordinary skill in the art to which this invention belongs. However, unless otherwise specified, the term described below will have the meaning indicated below over the entire specification:

As used herein, the term "about" refers to being within 5% of a particular value or range, and preferably within 1% to 2%. For example, "about 10%" refers to 9.5% to 10.5%, and preferably, 9.8% to 10.2%. For another example, "about 100° C." refers to 95° C. to 105° C., and preferably, 98° C. to 102° C.

As used herein, the term "free base" refers to the parent compound of Formula (I) as distinct from any salt thereof.

As used herein, the term "substantially pure" means at least 95% pure, preferably 99% pure, where 95% pure means not more than 5%, and 99% pure means not more than 1%, of any other form of the compound of Formula (I) being present (e.g., other crystalline form or amorphous form). As used herein, the term "essentially" means at least 90%, at least 95%, at least 99%, at least 99.5% or at least 99.9% on a referenced basis.

As used herein, a "polymorph" or "polymorphism" refers to the ability of a substance to exist in more than one crystal form, where the different crystal forms of a particular substance are referred to as "polymorphs." In general, it is believed that polymorphism may be affected by the ability of a molecule of a substance to change its conformation or to form different intermolecular or intra-molecular interactions, particularly hydrogen bonds, which is reflected in different atom arrangements in the crystal lattices of different polymorphs. The different polymorphs of a substance may possess different energies of the crystal lattice and, thus, in solid state they may show different physical properties such as, for instance and without limitation, form, density, melting point, color, stability, solubility, and dissolution rate, which may, in turn, affect properties such as, and without limitation, stability, dissolution rate and/or bioavailability of a given polymorph and its suitability for use as a pharmaceutical and in pharmaceutical compositions.

As used herein, in reference to salts of Formula (I), the terms bis- (e.g., bis-hydrochloride), 2- (e.g., 2 HCl), and di- (e.g., dihydrochloride) are used interchangeably. For example, as used herein, bis-hydrochloride, bis-chloride and dihydrochloride have the same meaning.

A crystalline form may be characterized by the presence of observable peaks in a PXRD pattern measured on the crystalline form. The PXRD patterns measured or calculated for the salts and crystalline forms reported herein represent a fingerprint that can be compared to other experimentally determined patterns to find a match. Identity of the respective crystalline forms is established by overlap or match of an experimentally determined PXRD pattern with the PXRD pattern of the crystalline forms reported herein. In various embodiments, the salts and crystalline forms are characterized by PXRD peaks. Thus, in various embodiments, a salt or crystalline form is characterized by a match of: one, two, three, four, five, six, seven, eight, nine, ten, or more, peaks; two or more peaks; three or more peaks; four or more peaks; five or more peaks, and so on, from the respective PXRD patterns. In some embodiments, a salt or crystalline form may be characterized by a match of peaks having a relative intensity (I/Io) of about 5% or more or about 10% or more where I indicates the intensity of each peak and Io indicates the intensity of the highest peak.

Unless otherwise specified, it must be apparent to a skilled practitioner that the values of peaks from PXRD studies reported in this invention are associated with experimental errors typically observable in this field. Specifically, unless otherwise specified, a peak is interpreted as to be located within ±0.5° of the value reported herein or, more specifically, a peak is interpreted as to be located within ±0.2° of the value reported herein.

In some embodiments, the percent crystallinity of any of the salts or crystalline forms of the compound of Formula (I) described herein can vary with respect to the total amount of the compound of Formula (I). In particular, certain embodiments provide for the percent crystallinity of a salt or crystalline form of the compound of Formula (I) being at least 10%, at least 20%, at least 30%, at least 40%, at least 50%, at least, 60%, at least 70%, at least 80%, at least 90%, at least 95%, or at least 99%. In some embodiments, the percent crystallinity can be substantially 100%, where substantially 100% indicates that the entire amount of the compound of Formula (I) appears to be crystalline as best can be determined using methods known in the art. Accordingly, pharmaceutical compositions and therapeutically effective amounts of the compound of Formula (I) can include amounts that vary in crystallinity. These include instances where the compound of Formula (I) is used as an active pharmaceutical ingredient (API) in various formulations and solid forms, including where an amount of the compound of Formula (I) in a solid form is subsequently dissolved, partially dissolved, or suspended or dispersed in a liquid.

Salts of the Compound of Formula (I)

In some embodiments, the present invention provides salts of the compound of Formula (I).

Formula (I) free base is poorly soluble in water with a solubility of less than 0.4 µg/mL. Salt forms of free base compounds may result in improved water solubility. Salt forms should also possess overall physicochemical properties required for pharmaceutical applications, such as for example but not limited to, reproducibility for the preparation of particular crystalline polymorphs, a high degree of crystallinity, stability of crystalline forms, chemical stability, and low hygroscopicity.

Compound of Formula (I) free base may be prepared according to the procedure described in WO 2013/100632, which is hereby incorporated by reference in its entirety.

For the identification of suitable salt types for the compound of Formula (I), salts of the compound of Formula (I) free base were prepared using various acids and solvents according to various conditions and procedures, and the physicochemical properties of the thus-obtained salts were evaluated. In some embodiments, Formula (I) salts include a hydrochloric acid salt (hydrochloride salt), a sulfuric acid salt (hydrogensulfate salt), a p-toluenesulfonic acid salt (p-toluenesulfonate salt), an ethanesulfonic acid salt (ethanesulfonate salt) and a methanesulfonic acid salt (methanesulfonate salt).

In some embodiments, a salt of Formula (I) is selected from a hydrochloride salt, a hydrogensulfate salt, a p-toluenesulfonate salt, an ethanesulfonate salt and a methanesulfonate salt.

In some embodiments, the Formula (I) salt is selected from the bis-hydrochloride salt, the bis-hydrogensulfate salt, the bis-p-toluenesulfonate salt, the bis-ethanesulfonate salt, and the bis-methanesulfonate salt.

In one embodiment, the Formula (I) salt is the bis-hydrochloride salt. In another embodiment, the Formula (I) salt is the bis-hydrogensulfate salt. In another embodiment, the Formula (I) salt is the bis-p-toluenesulfonate salt. In another embodiment, the Formula (I) salt is the bis-ethanesulfonate salt. In another embodiment, the Formula (I) salt is the bis-methanesulfonate salt.

In some embodiments, the Formula (I) salt is in amorphous form. In some embodiments, the Formula (I) salt is in crystalline form. In some embodiments, the Formula (I) salt is a mixture of amorphous and crystalline forms.

Crystalline Forms of the Compound of Formula (I) and Salts Thereof

In some embodiments, crystalline the compound of Formula (I) and salts thereof are provided. Based on experimentation to date, crystalline forms of Formula (I) salts thereof provide for improved physicochemical properties as compared to free base forms and amorphous forms.

In some embodiments, the crystalline form of the compound of Formula (I) is a free base. In some embodiments, the free base is characterized by a PXRD pattern in accordance with FIG. 29. In some such embodiments, the free base is characterized by a PXRD pattern having one, two, three, four, five, six or seven peaks, three or more peaks, or five or more peaks selected from those at diffraction angle 2θ±0.2° values of 4.6°, 9.2°, 12.7°, 13.8°, 25.9°, 26.5°, and 27.0°, when irradiated with a Cu-Kα light source. In some embodiments, the free base is characterized by a PXRD pattern having one, two, three, four, or five peaks, or three or more peaks selected from those at diffraction angle 2θ±0.2° values of 9.2°, 12.7°, 13.8°, 25.9° and 27.0°.

In some other embodiments, the crystalline form of the compound of Formula (I) is a salt. In some such embodiments, the salt is selected from a hydrochloride salt, a hydrogensulfate salt, a p-toluenesulfonate salt, an ethanesulfonate salt, and a methanesulfonate salt. In some such embodiments, the salt is selected from the bis-hydrochloride salt, the bis-hydrogensulfate salt, the bis-p-toluenesulfonate salt, the bis-ethanesulfonate salt, the bis-methanesulfonate salt, and the bis-benzenesulfonate salt.

In one embodiment of the present invention, provided are various crystalline forms of the hydrochloride salt of the compound of Formula (I).

Figure 35:
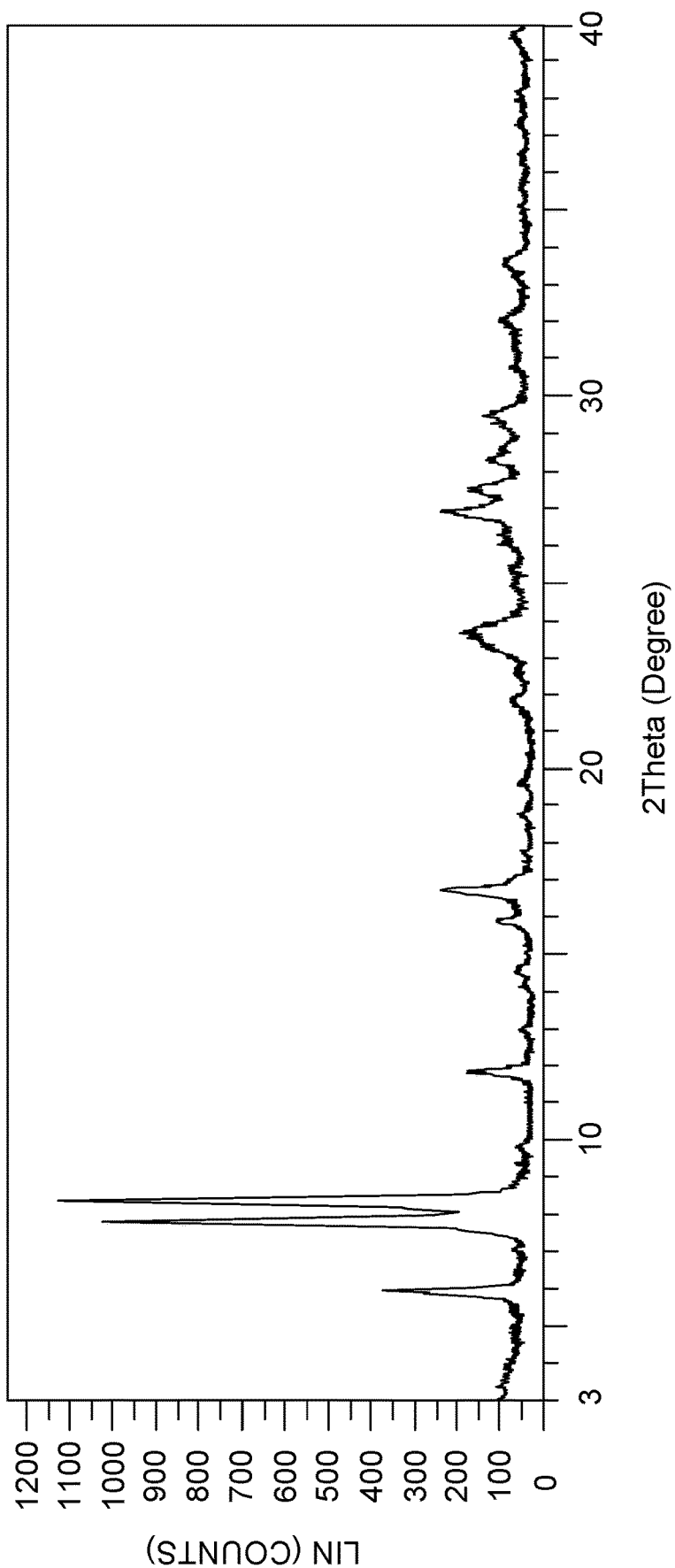
FIG. 35 shows a PXRD pattern for Formula (I) bis-hydrochloride salt crystalline polymorph Form I.

In some embodiments, the Formula (I) salt is bis-hydrochloride salt polymorph Form I characterized by a PXRD pattern in accordance with FIG. 35. In some such embodiments, bis-hydrochloride salt polymorph Form I is characterized by a PXRD pattern having one, two, three, four, five, six, seven, eight, nine or ten peaks, three or more peaks, or five or more peaks selected from those at diffraction angle 2θ±0.2° values of 5.89°, 7.77°, 8.31°, 11.80°, 16.68°, 23.22°, 23.69°, 26.89°, 27.51°, 28.29°, and 29.53° when irradiated with a Cu-Kα light source. In some such embodiments, bis-hydrochloride salt polymorph Form I is characterized by a PXRD pattern having one, two, three, four, five, six, seven, or eight peaks, three or more peaks, or five or more peaks selected from those at diffraction angle 2θ±0.2° values of 5.89°, 7.77°, 8.31° 11.80°, 16.68°, 23.69°, 26.89°, and 27.51. In some embodiments, bis-hydrochloride salt polymorph Form I is characterized by a PXRD pattern having one, two, three, four, or five peaks, or three or more peaks selected from those at diffraction angle 2θ±0.2° values of 5.89°, 7.77°, 8.31°, 16.68° and 26.89°. In some embodiments, bis-hydrochloride salt polymorph Form I is characterized by a PXRD pattern having one, two, or three peaks selected from those at diffraction angle 2θ±0.2° values of 5.89°, 7.77°, and 8.31°. In some embodiments, bis-hydrochloride salt polymorph Form I is characterized by peaks having I/Io ratios equal to or higher than 10% at diffraction angle 2θ±0.2° values of 5.89°, 7.77°, 8.31°, 11.80°, 16.68°, 23.22°, 23.69°, 26.89°, 27.51°, 28.29° and 29.53°.

In some embodiments, the crystalline Formula (I) bis-hydrochloride salt polymorph Form I is a trihydrate.

Figure 14:
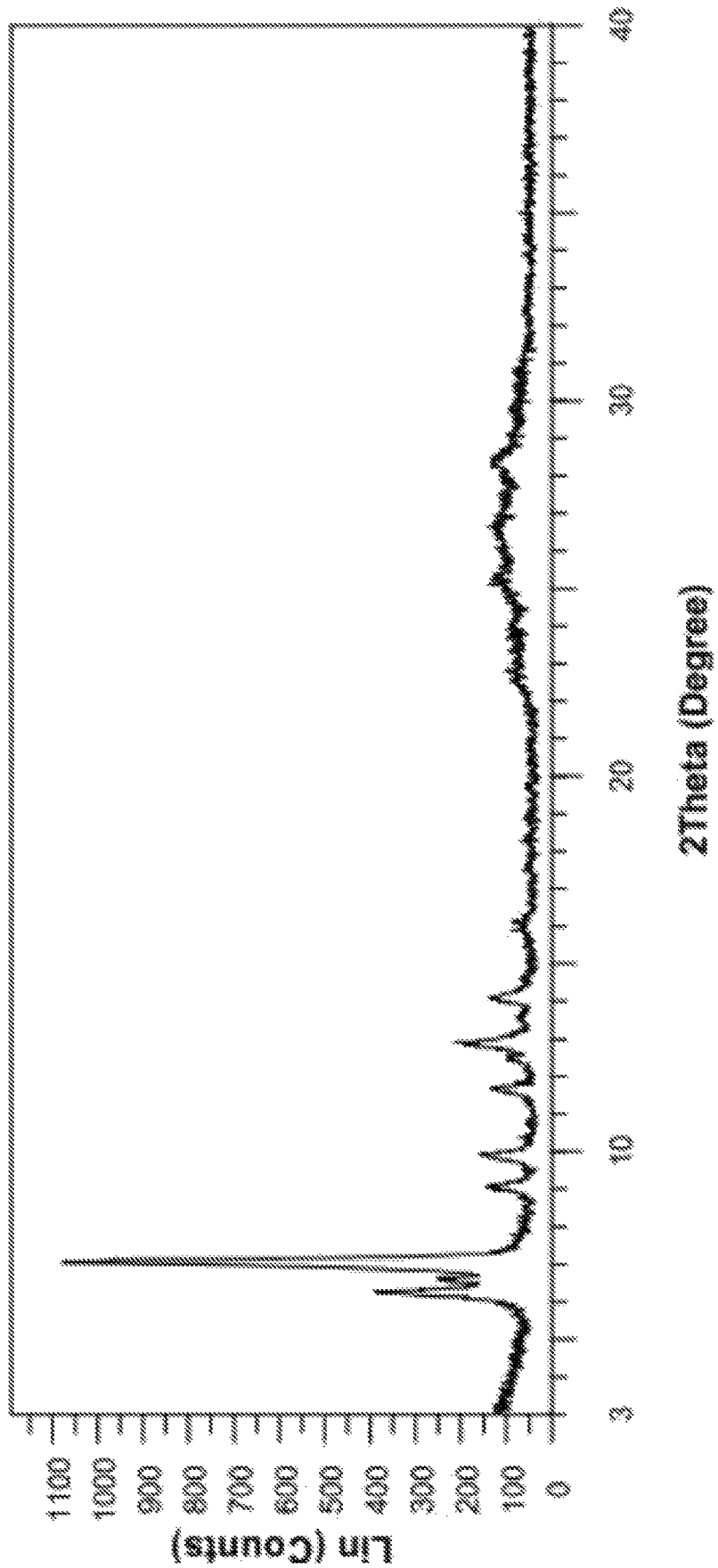
FIG. 14 shows a PXRD pattern for Formula (I) bis-hydrochloride salt crystalline polymorph Form II.

In some embodiments, the Formula (I) salt is bis-hydrochloride salt polymorph Form II characterized by a PXRD pattern in accordance with FIG. 14. In some such embodiments, bis-hydrochloride salt polymorph Form II is characterized by a PXRD pattern having one, two, three, four, five, six, seven, eight, or nine peaks, three or more peaks, or five or more peaks selected from those at diffraction angle 2θ±0.2° values of 6.19°, 6.55°, 7.00°, 9.01°, 9.85°, 11.64°, 12.86°, 14.05°, and 25.31°, when irradiated with a Cu-Kα light source. In some embodiments, bis-hydrochloride salt polymorph Form II is characterized by a PXRD pattern having one, two, three, four, or five peaks, or three or more peaks selected from those at diffraction angle 2θ±0.2° values of 6.19°, 6.55°, 7.00°, 9.01° and 12.86°. In some embodiments, bis-hydrochloride salt polymorph Form II is characterized by a PXRD pattern having one, two or three peaks selected from those at diffraction angle 2θ±0.2° values of 6.19°, 6.55°, and 7.00°. In some embodiments, bis-hydrochloride salt polymorph Form II is characterized by peaks having I/Io ratios equal to or higher than 10% at diffraction angle 2θ±0.2° values of 6.19°, 6.55°, 7.00°, 9.01°, 9.85°, 11.64°, 12.86°, 14.05° and 25.31°.

Figure 17:
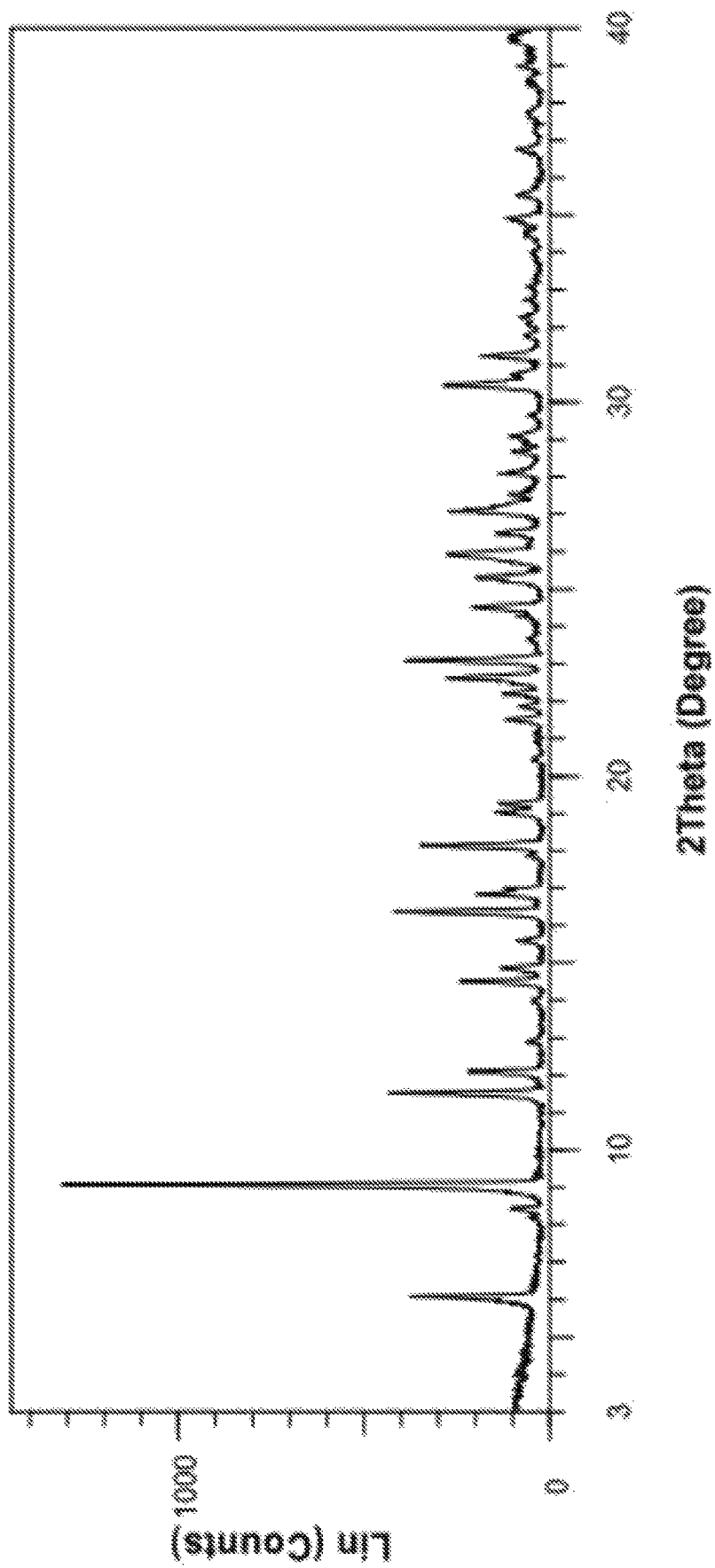
FIG. 17 shows a PXRD pattern for Formula (I) bis-hydrochloride salt crystalline polymorph Form III.

In some embodiments, the Formula (I) salt is bis-hydrochloride salt polymorph Form III characterized by a PXRD pattern in accordance with FIG. 17. In some embodiments, bis-hydrochloride salt polymorph Form III is characterized by a PXRD pattern having one, two, three, four, five, six, seven, eight, nine, or ten peaks, three or more peaks, or five or more peaks selected from those at diffraction angle 2θ±0.2° values of 6.01°, 9.00°, 11.47°, 12.05°, 14.48°, 16.33°, 16.83°, 18.13°, 19.01°, 19.26°, 22.63°, 23.10°, 24.51°±0.2°, 25.31°, 25.94°, 26.51°, 27.10°, 28.12°, 30.44° and 31.25°, when irradiated with a Cu-Kα light source. In some embodiments, bis-hydrochloride salt polymorph Form III is characterized by a PXRD pattern having one, two, three, four, five, six, seven, eight, nine, or ten peaks, three or more peaks, or five or more peaks selected from those at diffraction angle 2θ±0.2° values of 6.01°, 9.00°, 11.47°, 16.33°, 18.13°, 22.63°, 23.10°, 25.94°, 27.10° and 30.44°. In some such embodiments, bis-hydrochloride salt polymorph Form III is characterized by a PXRD pattern having one, two, three, four, five, six, seven, eight, nine, or ten peaks, three or more peaks, or five or more peaks selected from those at diffraction angle 2θ±0.2° values of 6.01°, 9.00°, 11.47°, 14.48°, 16.33°, 18.13°, 22.63°, 23.10°, 27.10°, and 30.47°. In some embodiments, bis-hydrochloride salt polymorph Form III is characterized by a PXRD pattern having one, two, three, four, or five peaks, or three or more peaks selected from those at diffraction angle 2θ±0.2° values of 6.01°, 9.00°, 11.47°, 16.33° and 23.10°. In some embodiments, bis-hydrochloride salt polymorph Form III is characterized by a PXRD pattern having one, two, or three peaks selected from those at diffraction angle 2θ±0.2° values of 9.00°, 11.47°, and 6.33°. In some embodiments, bis-hydrochloride salt polymorph Form III is characterized by peaks having I/Io ratios equal to or higher than 10% at diffraction angle 2θ±0.2° values of 6.01°, 9.00°, 11.47°, 12.05°, 14.48°, 16.33°, 16.83°, 18.13°, 19.01°, 19.26°, 22.63°, 23.10°, 24.51°, 25.31°, 25.94°, 26.51°, 27.10°, 28.12°, 30.47° and 31.25°

Figure 20:
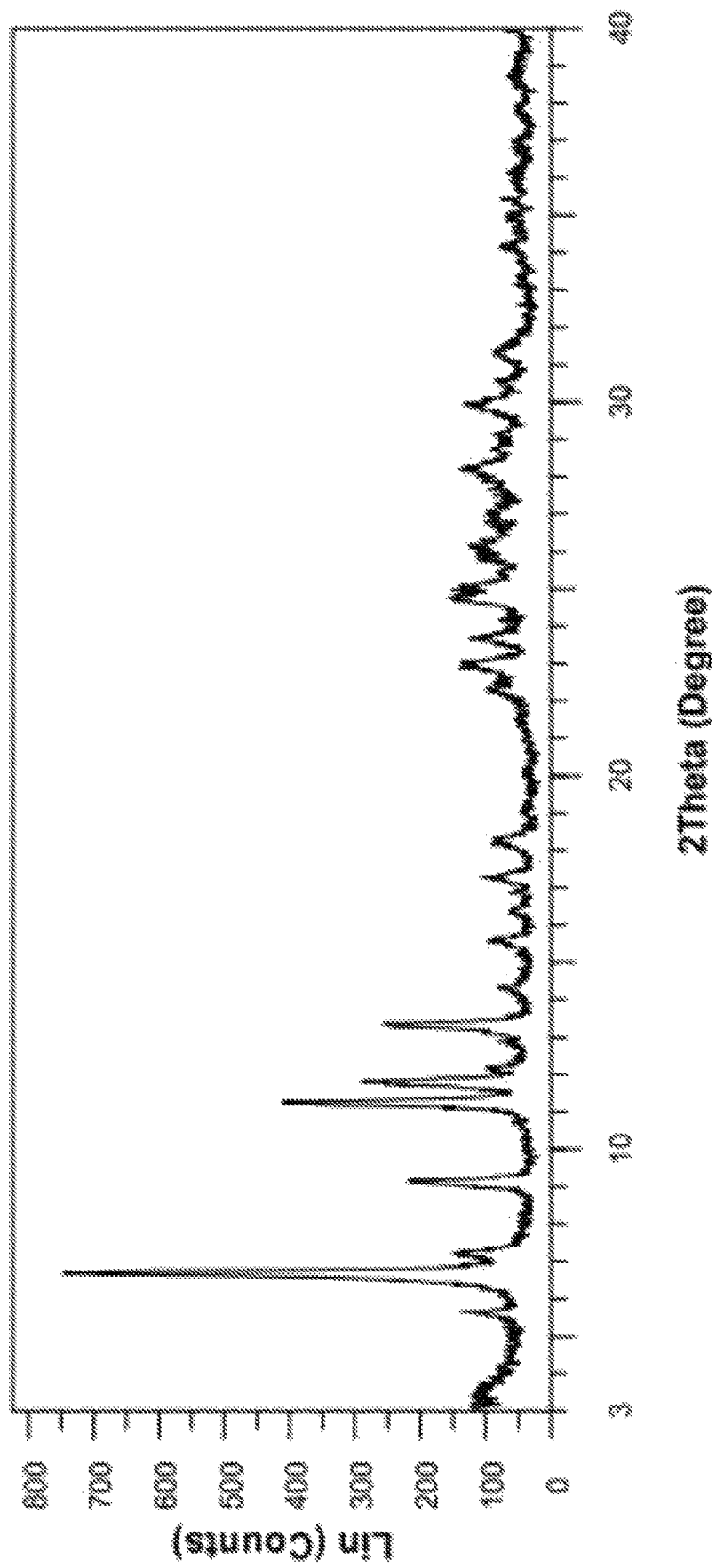
FIG. 20 shows a PXRD pattern for Formula (I) bis-hydrochloride salt crystalline polymorph Form IV.

In some embodiments, the Formula (I) salt is bis-hydrochloride salt polymorph Form IV characterized by a PXRD pattern in accordance with FIG. 20. In some such embodiments, bis-hydrochloride salt polymorph Form IV is characterized by a PXRD pattern having one, two, three, four, five, six, seven, eight, nine, or ten peaks, three or more peaks, or five or more peaks selected from those at diffraction angle 2θ±0.2° values of 5.56°, 6.64°, 7.15°, 9.07°, 11.22°, 11.76°, 12.12°, 13.30°, 14.28°, 15.57°, 17.26°, 18.25°, 22.26°, 22.95°, 23.69°, 24.77°, 25.06°, 25.88°, 28.20°, 29.92°, 31.33° and 34.17°, when irradiated with a Cu-Kα light source. In some such embodiments, bis-hydrochloride salt polymorph Form IV is characterized by a PXRD pattern having one, two, three, four, five, six, seven, eight, nine, or ten peaks, three or more peaks, or five or more peaks selected from those at diffraction angle 2θ±0.2° values of 6.64°, 7.15°, 9.07°, 11.22°, 11.76°, 13.30°, 22.95°, 23.69°, 24.77°, 25.06°, 28.20°, and 29.92°. In some such embodiments, bis-hydrochloride salt polymorph Form IV is characterized by a PXRD pattern having one, two, three, four, five, six, seven, eight, nine, or ten peaks, three or more peaks, or five or more peaks selected from those at diffraction angle 2θ±0.2° values of 6.64°, 7.15°, 9.07°, 11.22°, 11.76°, 13.30°, 22.95°, 23.69°, 24.77°, and 25.06°. In some embodiments, bis-hydrochloride salt polymorph Form IV is characterized by a PXRD pattern having one, two, three, four, or five peaks, or three or more peaks selected from those at diffraction angle 2θ±0.2° values of 6.64°, 9.07°, 11.22°, 11.76° and 13.30°. In some embodiments, bis-hydrochloride salt polymorph Form IV is characterized by a PXRD pattern having one, two, or three peaks selected from those at diffraction angle 2θ±0.2° values of 6.64°, 11.22°, and 11.76°. In some embodiments, bis-hydrochloride salt polymorph Form IV is characterized by peaks having I/Io ratios equal to or higher than 10% at diffraction angle 2θ±0.2° values of 5.56°, 6.64°, 7.15°, 9.07°, 11.22°, 11.76°, 12.12°, 13.30°, 14.28°, 15.57°, 17.26°, 18.2°, 22.3°, 22.9°, 23.7°, 24.8°, 25.1°, 25.9°, 28.2°, 29.9°, 31.3° and 34.2° (2θ±0.2°).

Figure 21:
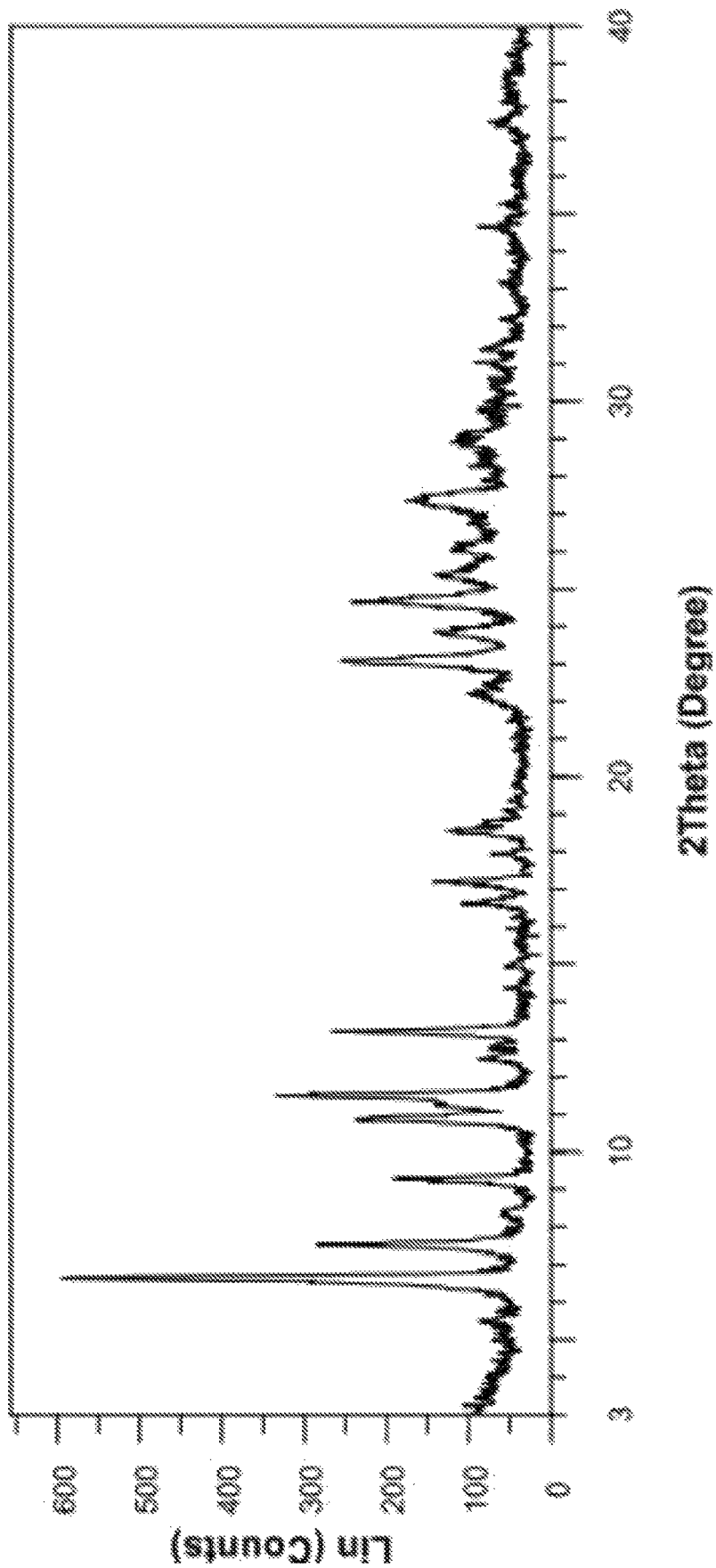
FIG. 21 shows a PXRD pattern for Formula (I) bis-hydrochloride salt crystalline polymorph Form V.

In some embodiments, the Formula (I) salt is bis-hydrochloride salt polymorph Form V characterized by a PXRD pattern in accordance with FIG. 21. In some such embodiments, bis-hydrochloride salt polymorph Form V is characterized by a PXRD pattern having one, two, three, four, five, six, seven, eight, nine, or ten peaks, three or more peaks, or five or more peaks selected from those at diffraction angle 2θ±0.2° values of 5.44°, 6.58°, 7.48°, 9.22°, 10.84°, 11.47°, 12.45°, 13.17°, 16.61°, 17.18°, 17.92°, 18.52°, 22.21°, 23.07°, 23.84°, 24.70°, 25.37°, 26.08°, 27.33°, 29.12°, 31.02°, 31.43°, 34.65° and 37.46°, when irradiated with a Cu-Kα light source. In some such embodiments, bis-hydrochloride salt polymorph Form V is characterized by a PXRD pattern having one, two, three, four, five, six, seven, eight, nine, or ten peaks, three or more peaks, or five or more peaks selected from those at diffraction angle 2θ±0.2° values of 6.58°, 7.48°, 9.22°, 10.84°, 11.47°, 13.17°, 16.61°, 17.18°, 18.52°, 22.21°, 23.07°, 23.84°, 24.70°, 25.37°, 26.08°, 27.33°, and 29.12°. In some such embodiments, bis-hydrochloride salt polymorph Form V is characterized by a PXRD pattern having one, two, three, four, five, six, seven, eight, nine, or ten peaks, three or more peaks, or five or more peaks selected from those at diffraction angle 2θ±0.2° values of 6.58°, 7.48°, 9.22°, 10.84°, 11.47°, 13.17°, 17.18°, 18.52°, 23.07°, 23.84°, 24.70°, 25.37° and 27.33°. In some such embodiments, bis-hydrochloride salt polymorph Form V is characterized by a PXRD pattern having one, two, three, four, five, six, seven, eight, nine, or ten peaks, three or more peaks, or five or more peaks selected from those at diffraction angle 2θ±0.2° values of 6.58°±0.2°, 7.48°±0.2°, 9.22°±0.2°, 10.84°±0.2°, 11.47°±0.2°, 13.17°±0.2°, 17.18°±0.2°, 23.07°±0.2°, 24.70°±0.2°, and 27.33°±0.2°. In some embodiments, bis-hydrochloride salt polymorph Form V is characterized by a PXRD pattern having one, two, three, four, or five peaks, or three or more peaks selected from those at diffraction angle 2θ±0.2° values of 6.58°, 7.48°, 11.47°, 13.17° and 23.07°. In some embodiments, bis-hydrochloride salt polymorph Form V is characterized by a PXRD pattern having one, two, or three peaks selected from those at diffraction angle 2θ±0.2° values of 6.58°, 7.48°, and 11.47°. In some embodiments, bis-hydrochloride salt polymorph Form II is characterized by peaks having I/Io ratios equal to or higher than 10% at diffraction angle 2θ±0.2° values of 5.44°, 6.58°, 7.48°, 9.22°, 10.84°, 11.47°, 12.45°, 13.17°, 16.61°, 17.18°, 17.92°, 18.52°, 22.21°, 23.07°, 23.84°, 24.70°, 25.37°, 26.08°, 27.33°, 29.12°, 31.02°, 31.43°, 34.65° and 37.46°.

Figure 22:
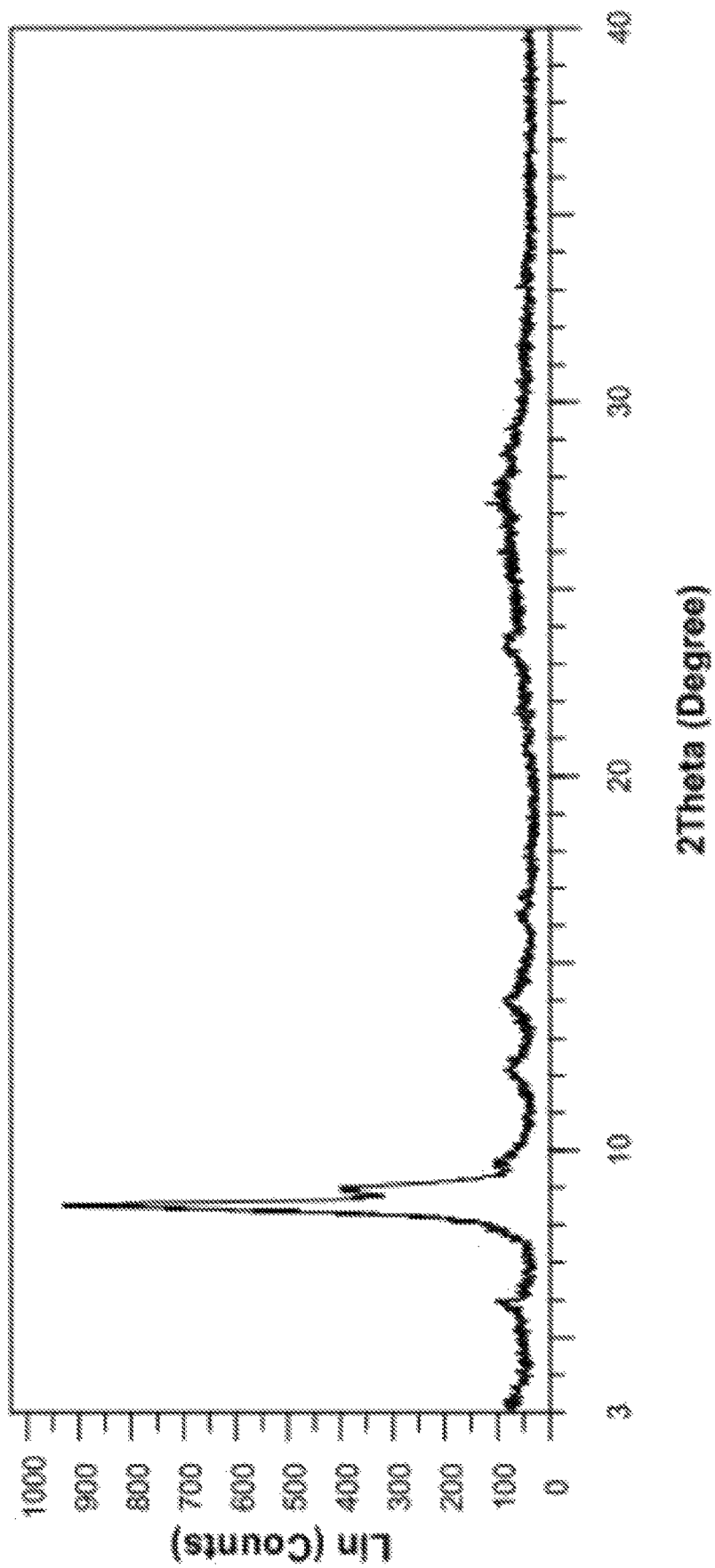
FIG. 22 shows a PXRD pattern for Formula (I) bis-hydrochloride salt crystalline polymorph Form VI.

In some embodiments, the Formula (I) salt is bis-hydrochloride salt polymorph Form VI characterized by a PXRD pattern in accordance with FIG. 22. In some such embodiments, bis-hydrochloride salt polymorph Form VI is characterized by a PXRD pattern having one, two, three, four, five, six, seven, or eight peaks, three or more peaks, or five or more peaks selected from those at diffraction angle 2θ±0.2° values of 5.86°, 8.47°, 8.90°, 12.10°, 14.00°, 16.30°, 16.71°, and 23.49°, when irradiated with a Cu-Kα light source. In some embodiments, bis-hydrochloride salt polymorph Form VI is characterized by a PXRD pattern having one, two, three, four, or five peaks, or three or more peaks selected from those at diffraction angle 2θ±0.2° values of 5.86°, 8.47°, 8.90°, 12.10°, and 23.49°. In some embodiments, bis-hydrochloride salt polymorph Form VI is characterized by a PXRD pattern having one, two or three peaks selected from those at diffraction angle 2θ±0.2° values of 5.86°, 8.47° and 8.90°. In some embodiments, bis-hydrochloride salt polymorph Form VI is characterized by peaks having I/Io ratios equal to or higher than 10% at diffraction angle 2θ±0.2° values of 8.5° and 8.9°.

Figure 4:
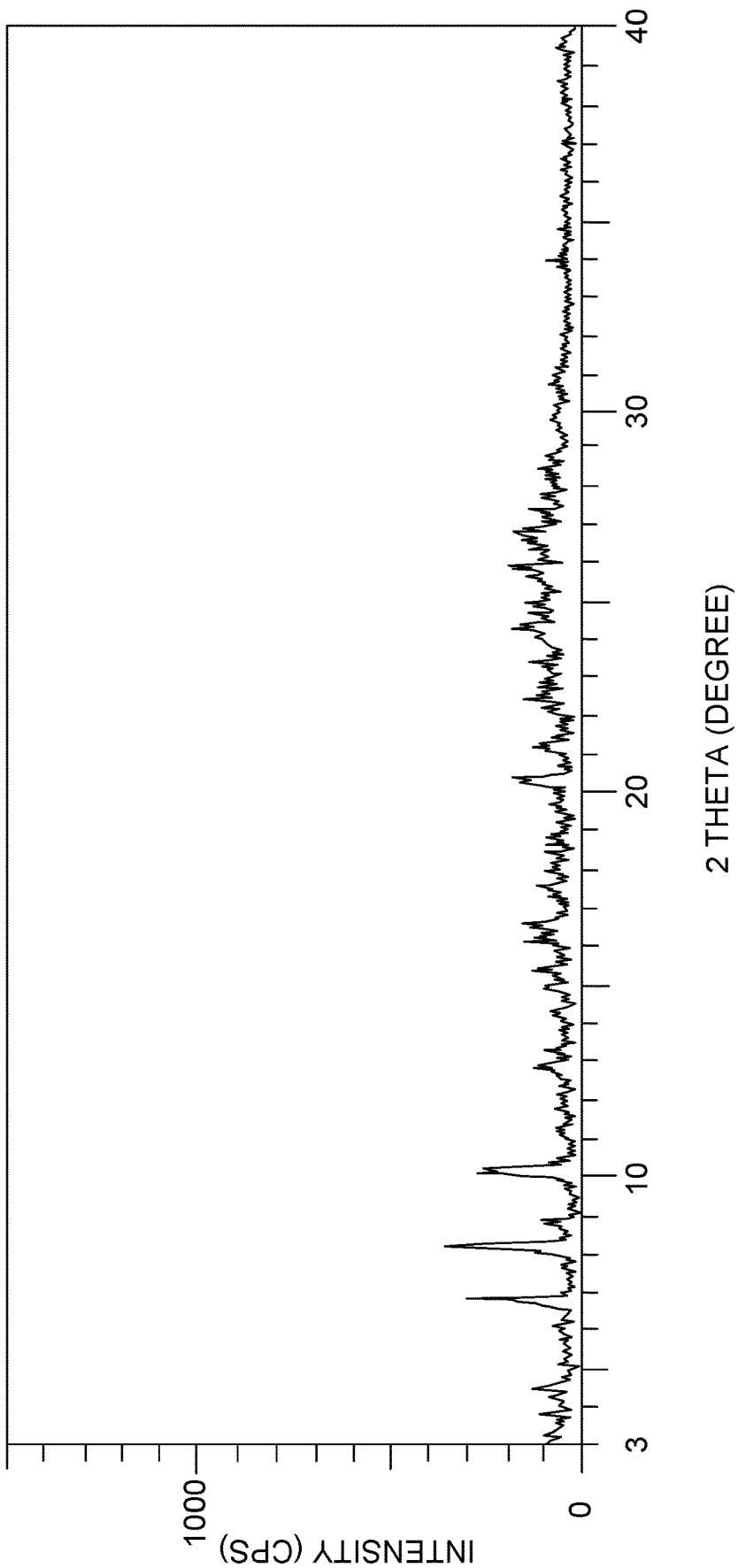
FIG. 4 shows a PXRD pattern for crystalline Formula (I) bis-hydrogensulfate salt.

In some embodiments, the Formula (I) salt is bis-hydrogensulfate salt characterized by a PXRD pattern in accordance with FIG. 4. In some such embodiments, Formula (I) bis-hydrogensulfate salt is characterized by a PXRD pattern having one, two, three, four, five, six, seven, or eight peaks, three or more peaks, or five or more peaks selected from those at diffraction angle 2θ±0.2° values of 5.7°, 7.4°, 7.9°, 9.4°, 11.5°, 13.7°, 15.0°, 15.9°, 16.9°, 17.7°, 18.5°, 18.9°, 20.3°, 20.9°, 21.6°, 22.4°, 22.9°, 23.3°, 24.0°, 24.4°, 24.6°, 25.3°, 25.9°, 26.5°, 27.3°, 28.7° and 33.7°, when irradiated with a Cu-Kα light source. In some such embodiments, Formula (I) bis-hydrogensulfate salt is characterized by a PXRD pattern having one, two, three, four, five, six, seven, or eight peaks, three or more peaks, or five or more peaks selected from those at diffraction angle 2θ±0.2° values of 5.7°, 7.4°, 7.9°, 11.5°, 13.7°, 15.0°, 15.9°, 18.5°, 18.9°, 20.3°, 20.9°, 21.6°, 22.4°, 22.9°, 23.3°, 24.0°, 24.4°, 24.6°, 25.3°, 25.9°, 26.5° and 27.3°. In some such embodiments, Formula (I) bis-hydrogensulfate salt is characterized by a PXRD pattern having one, two, three, four, five, six, seven, or eight peaks, three or more peaks, or five or more peaks selected from those at diffraction angle 2θ±0.2° values of 7.4°, 7.9°, 11.5°, 15.0°, 15.9°, 18.5°, 18.9°, 22.4°, 22.9°, 24.0°, 24.4°, 24.6°, 25.3° and 25.9°. In some such embodiments, Formula (I) bis-hydrogensulfate salt is characterized by a PXRD pattern having one, two, three, four, five, six, seven, or eight peaks, three or more peaks, or five or more peaks selected from those at diffraction angle 2θ±0.2° values of 7.4°, 7.9°, 15.0°, 15.9°, 18.5°, 22.4°, 24.0°, 24.4°, 25.3°, and 25.9°, when irradiated with a Cu-Kα light source. In some such embodiments, Formula (I) bis-hydrogensulfate salt is characterized by a PXRD pattern having one, two, three, four, or five peaks, or three or more peaks selected from those at diffraction angle 2θ±0.2° values of 7.9°, 15.0°, 15.9°, 18.5°, and 25.9°, when irradiated with a Cu-Kα light source. In some embodiments, bis-hydrogensulfate salt is characterized by peaks having I/Io ratios equal to or higher than 10% at diffraction angle 2θ±0.2° values of 5.7°, 7.4°, 7.9°, 9.4°, 11.5°, 13.7°, 15.0°, 15.9°, 16.9°, 17.7°, 18.5°, 18.9°, 20.3°, 20.9°, 21.6°, 22.4°, 22.9°, 23.3°, 24.0°, 24.4°, 24.6°, 25.3°, 25.9°, 26.5°, 27.3°, 28.7° and 33.7°.

Figure 26:
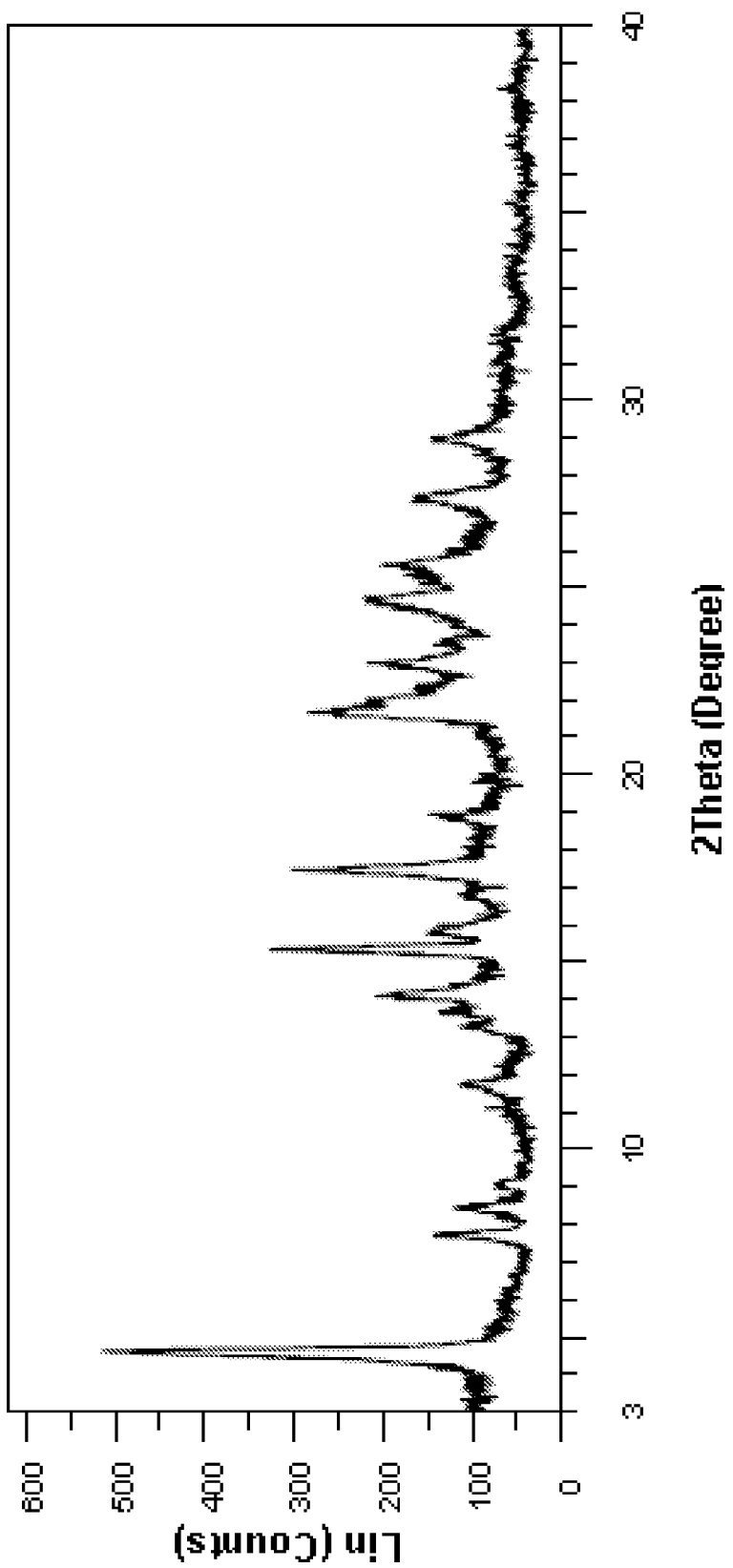
FIG. 26 shows a PXRD pattern for crystalline Formula (I) bis-p-toluenesulfonate salt Form A polymorph.

In some embodiments, the Formula (I) salt is bis-p-toluenesulfonate salt Form A polymorph characterized by a PXRD pattern in accordance with FIG. 26. In some such embodiments, Formula (I) bis-p-toluenesulfonate salt Form A polymorph is characterized by a PXRD pattern having one, two, three, four, five, six, seven, eight, nine, or ten peaks, three or more peaks, or five or more peaks selected from those at diffraction angle 2θ±0.2° values of 3.2°, 4.5°, 7.7°, 8.4°, 9.0°, 11.7°, 13.2°, 13.6°, 14.1°, 15.3°, 15.8°, 16.7°, 17.4°, 18.8°, 19.9°, 21.7°, 21.9°, 22.3°, 23.0°, 23.5°, 24.6°, 24.7°, 25.6°, 27.4° and 29.0° when irradiated with a Cu-Kα light source. In some such embodiments, Formula (I) bis-p-toluenesulfonate salt Form A polymorph is characterized by a PXRD pattern having one, two, three, four, five, six, seven, eight, nine or ten peaks, three or more peaks, or five or more peaks selected from those at diffraction angle 2θ±0.2° values of 3.2°, 4.5°, 7.7°, 8.4°, 11.7°, 13.2°, 13.6°, 14.1°, 15.3°, 15.8°, 17.4°, 18.8°, 21.7°, 21.9°, 22.3°, 23.0°, 23.5°, 24.6°, 24.7°, 25.6°, 27.4° and 29.0°. In some such embodiments, Formula (I) bis-p-toluenesulfonate salt Form A polymorph is characterized by a PXRD pattern having one, two, three, four, five, six, seven, eight, nine or ten peaks, three or more peaks, or five or more peaks selected from those at diffraction angle 2θ±0.2° values of 4.5°, 14.1°, 15.3°, 17.4°, 21.7°, 21.9°, 22.3°, 23.0°, 24.6°, 24.7°, 25.6° and 27.4°. In some such embodiments, Formula (I) bis-p-toluenesulfonate salt Form A polymorph is characterized by a PXRD pattern having one, two, three, four, five, six, seven, or eight peaks, three or more peaks, or five or more peaks selected from those at diffraction angle 2θ±0.2° values of 4.5°, 14.1°, 15.3°, 17.4°, 21.7°, 21.9°, 23.0°, 24.6°, 24.7°, and 25.6°. In some such embodiments, Formula (I) bis-p-toluenesulfonate salt Form A polymorph is characterized by a PXRD pattern having one, two, three, four, five, six, seven, or eight peaks, three or more peaks, or five or more peaks selected from those at diffraction angle 2θ±0.2° values of 4.5°, 15.3°, 17.4°, 21.7°, 21.9°, 23.0°, 24.6° and 24.7°. In some embodiments, Formula (I) bis-p-toluenesulfonate salt Form A polymorph is characterized by a PXRD pattern having one, two, three, four, or five peaks, or three or more peaks selected from those at diffraction angle 2θ±0.2° values of 4.5°, 15.3°, 17.4°, 21.7°, and 21.9°. In some embodiments, Formula (I) bis-p-toluenesulfonate salt Form A polymorph is characterized by a PXRD pattern having one, two, or three peaks selected from those at diffraction angle 2θ±0.2° values of 4.5°, 15.3° and 21.7°. In some embodiments, Formula (I) bis-p-toluenesulfonate salt Form A polymorph is characterized by peaks having I/Io ratios equal to or higher than 10% at diffraction angle 2θ±0.2° values of 3.2°, 4.5°, 7.7°, 8.4°, 9.0°, 11.7°, 13.2°, 13.6°, 14.1°, 15.3°, 15.8°, 16.7°, 17.4°, 18.8°, 19.9°, 21.7°, 21.9°, 22.3°, 23.0°, 23.5°, 24.6°, 24.7°, 25.6°, 27.4° and 29.0°.

Figure 27:
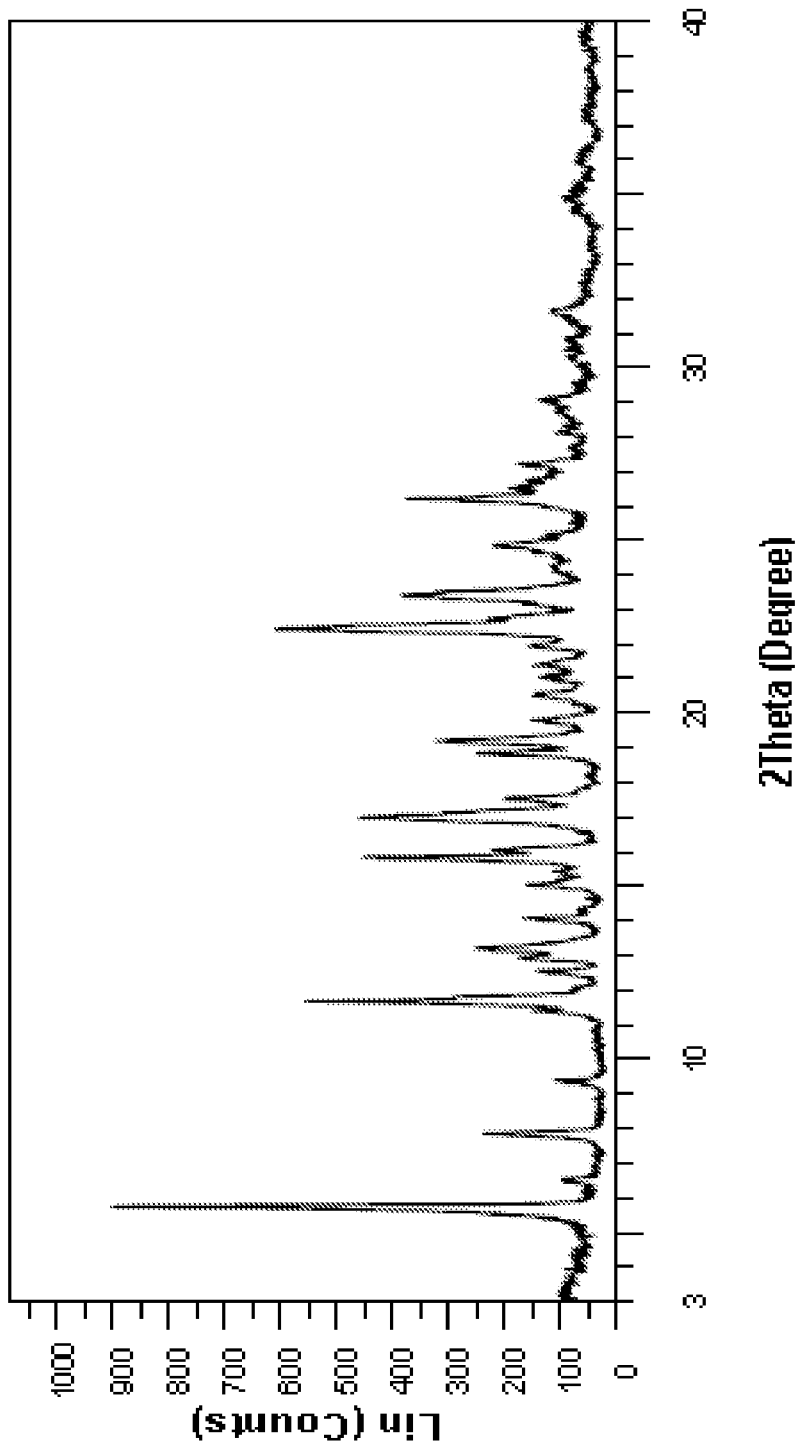
FIG. 27 shows a PXRD pattern for crystalline Formula (I) bis-p-toluenesulfonate salt Form B polymorph.

In some embodiments, the Formula (I) salt is bis-p-toluenesulfonate salt Form B polymorph characterized by a PXRD pattern in accordance with FIG. 27. In some such embodiments, Formula (I) bis-p-toluenesulfonate salt Form B polymorph is characterized by a PXRD pattern having one, two, three, four, five, six, seven, eight, nine or ten peaks, three or more peaks, or five or more peaks selected from those at diffraction angle 2θ±0.2° values of 5.7°, 7.8°, 9.3°, 11.4°, 11.6°, 12.5°, 12.9°, 13.2°, 14.0°, 15.0°, 15.8°, 16.0°, 17.0°, 17.5°, 18.8°, 19.2°, 19.8°, 20.5°, 21.0°, 21.4°, 21.9°, 22.4°, 22.8°, 23.4°, 24.2°, 24.9°, 26.2°, 27.2°, 28.1°, 29.1° and 31.6° when irradiated with a Cu-Kα light source. In some such embodiments, Formula (I) bis-p-toluenesulfonate salt Form B polymorph is characterized by a PXRD pattern having one, two, three, four, five, six, seven, eight, nine or ten peaks, three or more peaks, or five or more peaks selected from those at diffraction angle 2θ±0.2° values of 5.7°, 7.8°, 11.4°, 11.6°, 12.9°, 13.2°, 14.0°, 15.0°, 15.8°, 16.0°, 17.0°, 17.5°, 18.8°, 19.2°, 19.8°, 20.5°, 21.4°, 21.9°, 22.4°, 22.8°, 23.4°, 24.9°, 26.2°, 27.2° and 29.1°. In some such embodiments, Formula (I) bis-p-toluenesulfonate salt Form B polymorph is characterized by a PXRD pattern having one, two, three, four, five, six, seven, or eight peaks, three or more peaks, or five or more peaks selected from those at diffraction angle 2θ±0.2° values of 5.7°, 7.8°, 11.6°, 13.2°, 15.8°, 16.0°, 17.0°, 17.5°, 18.8°, 19.2°, 22.4°, 22.8°, 23.4°, 24.9° and 26.2°. In some such embodiments, Formula (I) bis-p-toluenesulfonate salt Form B polymorph is characterized by a PXRD pattern having one, two, three, four, five, six, seven, or eight peaks, three or more peaks, or five or more peaks selected from those at diffraction angle 2θ±0.2° values of 5.7°, 11.6°, 13.2°, 15.8°, 17.0°, 18.8°, 19.2°, 22.4°, 23.4°, and 26.2°. In some such embodiments, Formula (I) bis-p-toluenesulfonate salt Form B polymorph is characterized by a PXRD pattern having one, two, three, four, five, six, seven, or eight peaks, three or more peaks, or five or more peaks selected from those at diffraction angle 2θ±0.2° values of 5.7°, 11.6°, 15.8°, 17.0°, 19.2°, 22.4°, 23.4° and 26.2°. In some embodiments, Formula (I) bis-p-toluenesulfonate salt Form B polymorph is characterized by a PXRD pattern having one, two, three, four, or five peaks, or three or more peaks selected from those at diffraction angle 2θ±0.2° values of 5.7°, 11.6°, 15.8°, 17.0°, and 22.4°. In some embodiments, Formula (I) bis-p-toluenesulfonate salt Form B polymorph is characterized by a PXRD pattern having one, two, or three peaks selected from those at diffraction angle 2θ±0.2° values of 5.7°, 11.6° and 22.4°. In some embodiments, Formula (I) bis-p-toluenesulfonate salt Form B polymorph is characterized by peaks having I/Io ratios equal to or higher than 10% at diffraction angle 2θ±0.2° values of 5.7°, 7.8°, 9.3°, 11.4°, 11.6°, 12.5°, 12.9°, 13.2°, 14.0°, 15.0°, 15.8°, 16.0°, 17.0°, 17.5°, 18.8°, 19.2°, 19.8°, 20.5°, 21.0°, 21.4°, 21.9°, 22.4°, 22.8°, 23.4°, 24.2°, 24.9°, 26.2°, 27.2°, 28.1°, 29.1° and 31.6°.

Figure 28:
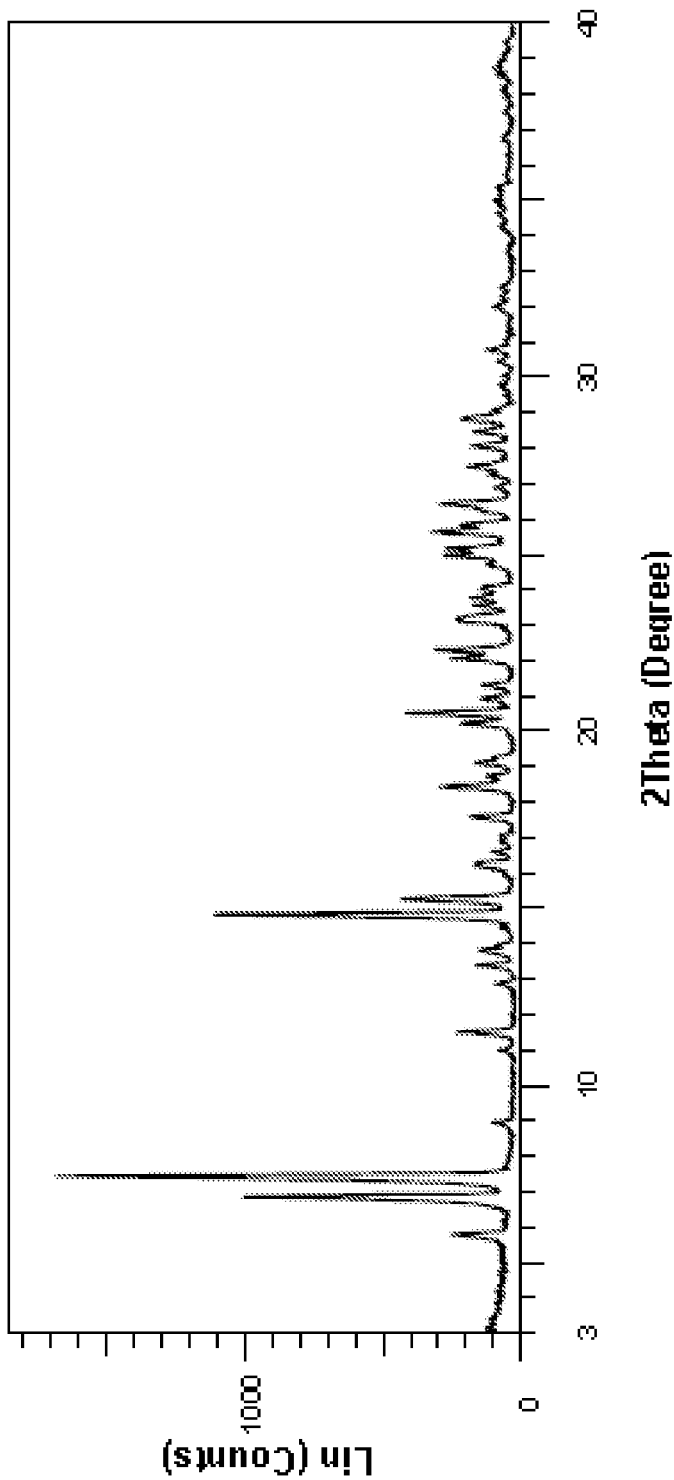
FIG. 28 shows a PXRD pattern for crystalline Formula (I) bis-ethanesulfonate salt.

In some embodiments, the Formula (I) salt is bis-p-ethanesulfonate salt characterized by a PXRD pattern in accordance with FIG. 28. In some such embodiments, Formula (I) bis-p-ethanesulfonate salt is characterized by a PXRD pattern having one, two, three, four, five, six, seven, eight, nine or ten peaks, three or more peaks, or five or more peaks selected from those at diffraction angle 2θ±0.2° values of 5.7°, 6.8°, 7.4°, 11.5°, 14.8°, 15.2°, 17.6°, 18.4°, 20.2°, 20.5°, 22.1°, 22.3°, 23.2°, 23.6°, 23.8°, 25.2°, 25.6°, 25.8°, 26.4°, 27.5°, 28.1° and 28.8°, when irradiated with a Cu-Kα light source. In some such embodiments, Formula (I) bis-p-ethanesulfonate salt is characterized by a PXRD pattern having one, two, three, four, five, six, seven, eight, nine or ten peaks, three or more peaks, or five or more peaks selected from those at diffraction angle 2θ±0.2° values of 6.8°, 7.4°, 14.8°, 15.2°, 18.4°, 20.5°, 22.3°, 25.2°, 25.6° and 26.4°. In some such embodiments, Formula (I) bis-p-ethanesulfonate salt is characterized by a PXRD pattern having one, two, three, four or five peaks, or three or more peaks selected from those at diffraction angle 2θ±0.2° values of 6.8°, 7.4°, 14.8°, 15.2°, and 20.5°. In some such embodiments, Formula (I) bis-p-ethanesulfonate salt is characterized by a PXRD pattern having one, two or three peaks selected from those at diffraction angle 2θ±0.2° values of 6.8°, 7.4° and 14.8°. In some embodiments, Formula (I) bis-p-ethanesulfonate salt is characterized by peaks having I/Io ratios equal to or higher than 10% at diffraction angle 2θ±0.2° values of 5.7°, 6.8°, 7.4°, 11.5°, 14.8°, 15.2°, 17.6°, 18.4°, 20.2°, 20.5°, 22.1°, 22.3°, 23.2°, 23.6°, 23.8°, 25.2°, 25.6°, 25.8°, 26.4°, 27.5°, 28.1° and 28.8°.

Figure 7:
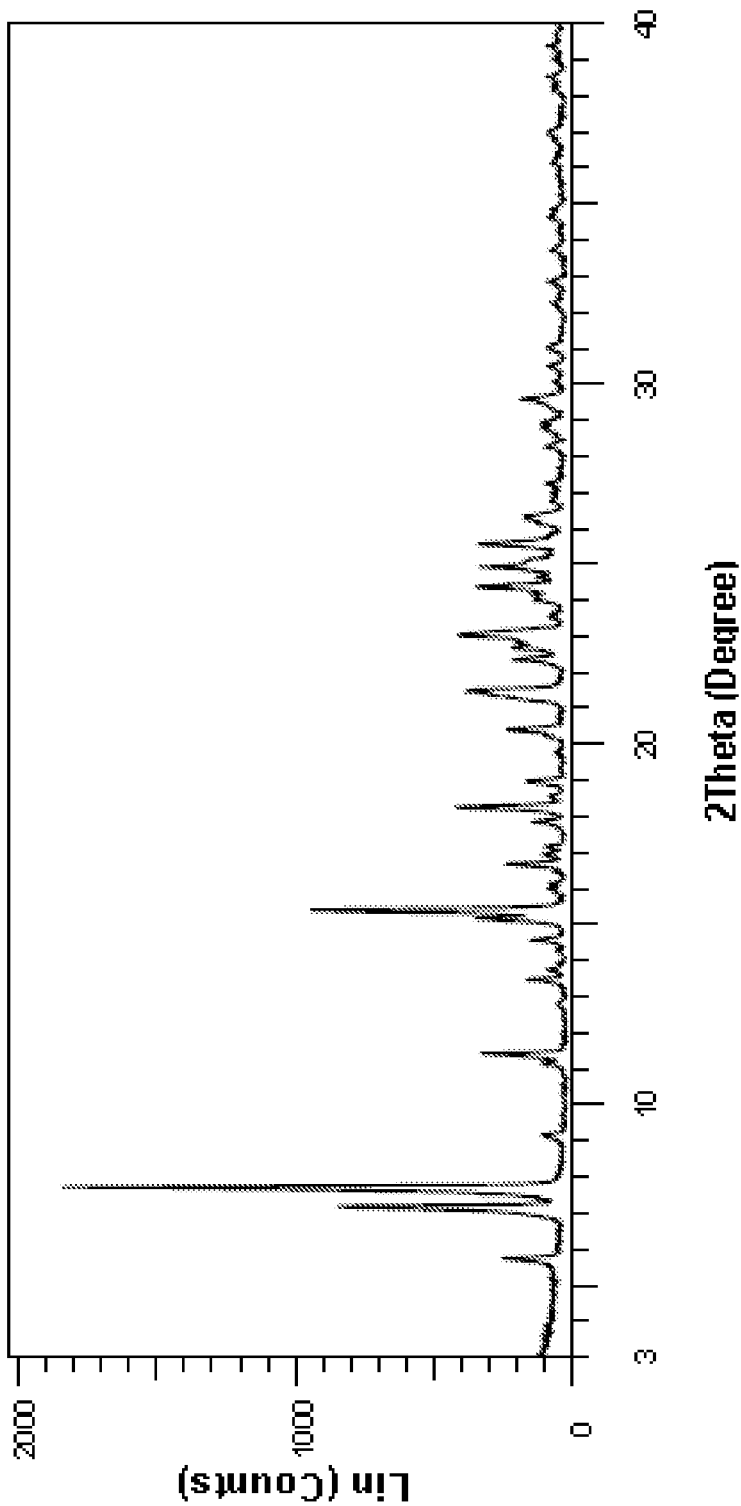
FIG. 7 shows a PXRD pattern for crystalline Formula (I) bis-methanesulfonate salt.

In some embodiments, the Formula (I) salt is bis-p-methanesulfonate salt characterized by a PXRD pattern in accordance with FIG. 7. In some such embodiments, Formula (I) bis-p-methanesulfonate salt is characterized by a PXRD pattern having one, two, three, four, five, six, seven, eight, nine or ten peaks, three or more peaks, or five or more peaks selected from those at diffraction angle 2θ±0.2° values of 5.6°, 7.1°, 7.6°, 11.4°, 15.1°, 15.4°, 16.6°, 18.2°, 20.4°, 21.5°, 22.3°, 22.7°, 23.1°, 24.4°, 24.9° and 25.6°, when irradiated with a Cu-Kα light source. In some such embodiments, Formula (I) bis-p-methanesulfonate salt is characterized by a PXRD pattern having one, two, three, four, five, six, seven, eight, nine or ten peaks, three or more peaks, or five or more peaks selected from those at diffraction angle 2θ±0.2° values of 7.1°, 7.6°, 11.4°, 15.1°, 15.4°, 18.2°, 21.5°, 23.1°, 24.4°, 24.9° and 25.6°. In some such embodiments, Formula (I) bis-p-methanesulfonate salt is characterized by a PXRD pattern having one, two, three, four, five, six, seven, eight, nine or ten peaks, three or more peaks, or five or more peaks selected from those at diffraction angle 2θ±0.2° values of 7.1°, 7.6°, 15.1°, 15.4°, 18.2°, 21.5°, 23.1°, 24.4°, 24.9°, and 25.6°. In some such embodiments, Formula (I) bis-p-methanesulfonate salt is characterized by a PXRD pattern having one, two, three, four, five, or six peaks, three or more peaks, or five or more peaks selected from those at diffraction angle 2θ±0.2° values of 7.1°, 7.6°, 15.4°, 18.2°, 21.5°, and 23.1°. In some such embodiments, Formula (I) bis-p-methanesulfonate salt is characterized by a PXRD pattern having one, two, three, four, or five peaks, or three or more peaks selected from those at diffraction angle 2θ±0.2° values of 7.1°, 7.6°, 15.4°, 18.2°, and 23.1. In some such embodiments, Formula (I) bis-p-methanesulfonate salt is characterized by a PXRD pattern having one, two, or three, peaks selected from those at diffraction angle 2θ±0.2° values of 7.1°, 7.6°, and 15.4°. In some embodiments, Formula (I) bis-p-methanesulfonate salt is characterized by peaks having I/Io ratios equal to or higher than 10% at diffraction angle 2θ±0.2° values of 5.6°, 7.1°, 7.6°, 11.4°, 15.1°, 15.4°, 16.6°, 18.2°, 20.4°, 21.5°, 22.3°, 22.7°, 23.1°, 24.4°, 24.9° and 25.6°.

Preparation of Crystalline Forms of the Compound of Formula (I) and Salts Thereof In some embodiments, crystalline acid salt forms of Formula (I) may be prepared by a process comprising the steps of: (a) combining an organic solvent and the free base of the compound of Formula (I) to form an admixture; (b) adding 2 to 3 equivalents of an acid per equivalent of Formula (I) to the admixture obtained in step (a) to form a slurry comprising solid crystalline Formula (I) salt; and (c) isolating the crystalline Formula (I) salt from the slurry. The salt may be optionally dried.

In some embodiments, the acid is selected from hydrochloric acid, sulfuric acid, p-toluenesulfonic acid, ethanesulfonic acid, methanesulfonic acid, benzenesulfonic acid, and mixtures thereof.

In some embodiments, the organic solvent is essentially anhydrous. Examples of the organic solvents include, for instance and without limitation, methanol, ethanol, tetrahydrofuran ("THF"), isopropyl alcohol ("IPA"), DMF, acetone, ethyl acetate, acetonitrile ("ACN"), methyl ethyl ketone, and combinations thereof. In some embodiments the solvent may further comprise water.

In some embodiments, the admixture of solvent and Formula (I) is a solution. In some embodiments, admixture of solvent and Formula (I) is a suspension or a slurry. In such embodiments, the minimum amount of solvent is the amount in which the free base of the compound of Formula (I), or a salt thereof, is soluble at a suitable temperature (such as, for instance, at reflux) or is the amount in which a suspension can be stirred at a desired temperature. The maximum amount of solvent is not narrowly limited and is the amount of solvent that results in a concentration of Formula (I), or a salt thereof, suitable for producing a practical yield and acceptable purity of crystalline product.

The equivalent ratio of acid to the compound of Formula (I) is about 2, about 2.1, about 2.2, about 2.3, about 2.4, about 2.5, about 2.6, about 2.7, about 2.8, about 2.9 or about 3.0, and ranges thereof, such as from about 2 to about 3, from about 2 to about 2.5, or from about 2.2 to about 2.5.

A crystalline form of a bis-hydrochloride salt of the compound of Formula (I) can be produced by a process comprising the following steps. Formula (I) free base is admixed with a solvent to form an admixture. The admixture may suitably be a slurry or a solution. In some aspects, the admixture may be heated. In some aspects, the admixture may be heated to reflux. From about 2 to about 3 equivalents of hydrochloric acid per equivalent of Formula (I) is added to the admixture to form a slurry comprising solid crystalline Formula (I) bis-hydrochloride. In some aspects, the slurry may be cooled, such as to less than about 25° C., to facilitate crystallization of Formula (I) bis-hydrochloride. The solid crystalline Formula (I) bis-hydrochloride may be isolated from the slurry by means known in the art including, for instance, filtration or centrifugation. Isolated crystalline Formula (I) bis-hydrochloride may optionally be washed to remove impurities. The crystals may then be dried by means known in the art including, for instance, vacuum oven drying or fluidized bed drying.

In some embodiments, the organic solvent is selected from methanol, ethanol and a mixture thereof. In such aspects, the dried crystalline Formula (I) bis-hydrochloride Form (I) is hydrated by exposure to air comprising water vapor. In some aspects, crystalline Formula (I) bis-hydrochloride polymorph Form I is a trihydrate.

In some particular embodiments, Formula (I) free base may optionally be admixed with an alcohol solvent to form a solution followed by filtration. In some aspects, the solvent is ethanol or methanol, or is methanol. The concentration of Formula (I) free base in solution is suitably from about 1 g/L to about 25 g/L, from about 5 g/L to about 20 g/L, or about 10 g/L. The temperature is selected to achieve a solution at the Formula (I) free base concentration, for instance, greater than 30° C., such as from about 35° C. to about 60° C. or from about 35° C. to about 50° C. Activated carbon may be optionally added to the admixture with stirring. The admixture is then filtered, optionally with a filtration aid such as Celite® (diatomaceous earth). The filtrate may then be concentrated, such as by evaporation, to form a Formula (I) free base residue. The residue is then suspended in ethanol. In some aspects, the ethanol is aqueous ethanol. In some aspects, the aqueous alcohol is from about 70% ethanol to about 90% ethanol, such as about 80% ethanol. The content of Formula (I) free base in the suspension is suitably from about 10 g/L to about 150 g/L, from about 25 g/L to about 75 g/L, or about 50 g/L. Hydrochloric acid is added to the suspension to form an admixture at an equivalent ratio of acid to Formula (I) free base as described elsewhere herein, such as from about 2 to about 3, from about 2 to about 2.5, or from about 2.2 to about 2.3. The admixture is heated with stirring, such as to reflux, and held for a time sufficient to essentially complete the conversion of Formula (I) free base to Formula (I) bis-hydrochloride. The admixture is then cooled to, such as to less than about 35° C., and the Formula (I) bis-hydrochloride Form I is isolated, such as by filtration. The Formula (I) bis-hydrochloride Form I is dried under vacuum at a suitable temperature, such as from about 40° C. to about 60° C. The dried solids may optionally be milled or ground. The dried solid is then exposed to air comprising water vapor to form hydrated Formula (I) bis-hydrochloride crystalline polymorph Form I. The humidification conditions are suitably, from about 30° C. to about 50° C. with exposure to air at from about 50% RH to about 95% RH, from about 60% RH to about 90% RH, or from about 70% RH to about 80% RH.

In some embodiments, the organic solvent is DMF and the dried crystalline Formula (I) bis-hydrochloride is polymorph Form V. In such embodiments, Formula (I) free base is combined with DMF to form a suspension having a Formula (I) content of from about 10 g/L to about 200 g/L, from about 25 g/L to about 150 g/L or from about 50 g/L to about 75 g/L. The suspension is heated to form a solution. In some aspects, the temperature is greater than 100° C., such as about 120° C., about 140° C., or reflux temperature. Hydrochloric acid is added to the solution at an equivalent ratio of acid to Formula (I) free base as described elsewhere herein to form a suspension comprising solid crystalline Formula (I) bis-hydrochloride Form V. In some aspects, the solution is cooled to less than 100° C., such as about 80° C., prior to acid addition. The suspension is then cooled and aged with stirring, such as at less than about 30° C. for at least an hour, and the Formula (I) bis-hydrochloride polymorph Form V is isolated, such as by filtration. The Formula (I) bis-hydrochloride Form V is dried under vacuum at a suitable temperature, such as from about 40° C. to about 60° C. The dried solids may optionally be milled or ground.

Various crystalline forms of Formula (I) bis-hydrochloride including crystalline Form II, crystalline Form III, crystalline Form IV, and crystalline Form VI can be produced from crystalline Form I.

Figure 25:
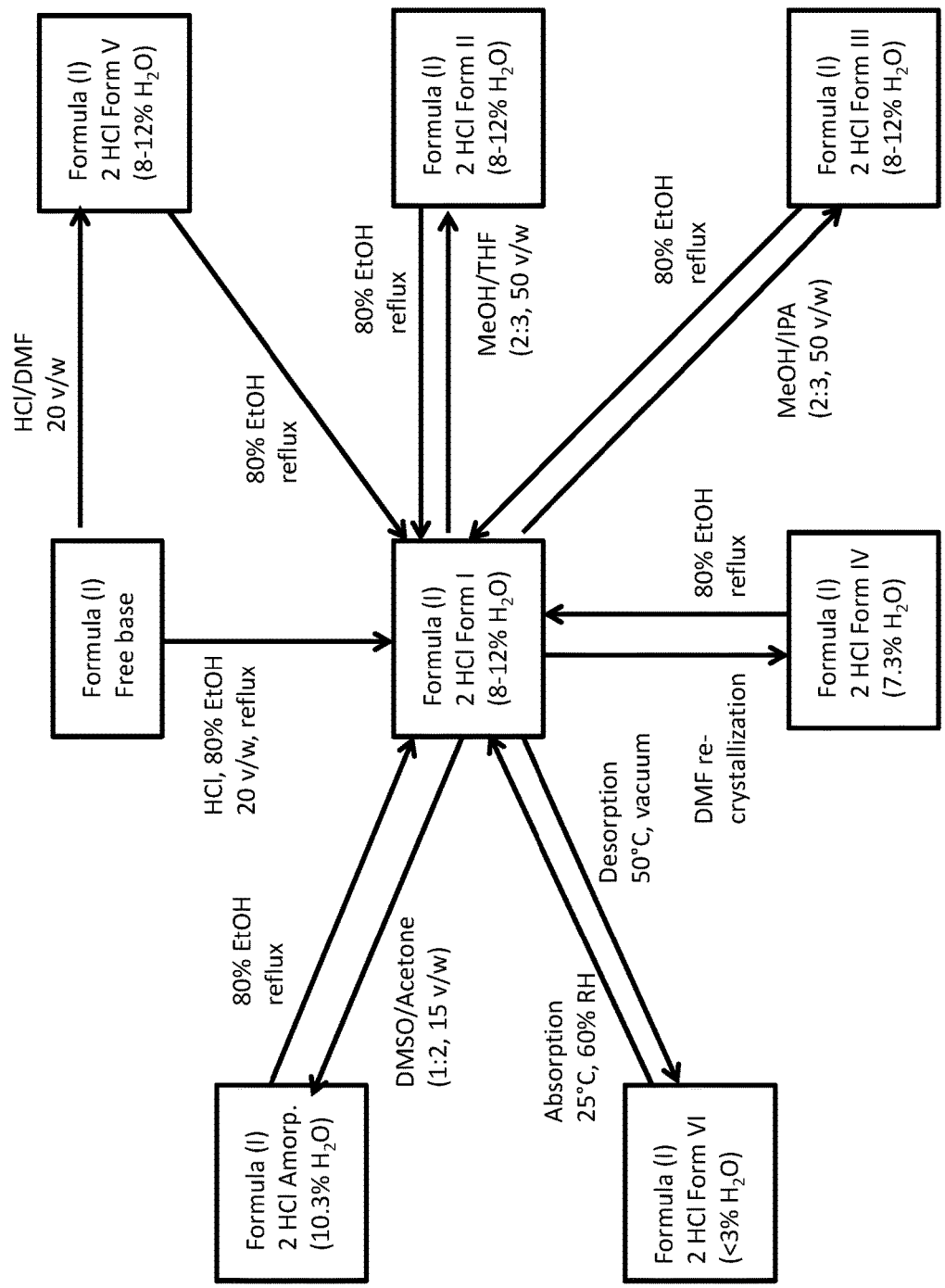
FIG. 25 shows the interconversion of Formula (I) bis-hydrochloride polymorph Form I to and from Forms II to VI, and to amorphous Formula (I) bis-hydrochloride as demonstrated in the present examples.

FIG. 25 illustrates and summarizes the interconversion between the polymorphs of the bis-hydrochloride salt of the compound of Formula (I). The crystalline Form II, Form III, and Form IV and the amorphous form can be prepared by recrystallization of the crystalline Form I. The crystalline Form V can be prepared from the free base of the compound of Formula (I). The crystalline Form VI can be converted to the crystalline Form I by water absorption (e.g., more than 60% of relative humidity). All other crystalline forms of Formula (I) can be converted to the crystalline Form I at the same conditions of reflux in about 80% ethanol.

In some embodiments, Formula (I) bis-hydrochloride polymorph Form II may be prepared from Form I. In some such embodiments, Form I Formula (I) bis-hydrochloride salt is combined with methanol and THF followed by heating, cooling and drying to generate Form II. The concentration of Form I in methanol/THF is suitably from about 5 g/L to about 100 g/L, from about 10 g/L to about 50 g/L, or from about 10 g/L to about 30 g/L. The volume ratio of methanol to THF is suitably from about 1.5:1 to about 0.25:1, from about 1:1 to about 0.5:1, or from about 0.75:1 to about 0.5:1. The temperature is suitably at least 60° C., or reflux. The admixture is then cooled and aged with stirring, such as at less than about 30° C. for at least an hour, and the Formula (I) bis-hydrochloride polymorph Form II is isolated, such as by filtration. The Form II polymorph is dried under vacuum at a suitable temperature, such as from about 40° C. to about 60° C. The dried solids may optionally be milled or ground. The dried solid is then exposed to air comprising water vapor to form hydrated Form II. The humidification conditions are suitably, from about 15° C. to about 50° C., or from about 15° C. to about 35° C., with exposure to air at from about 40% RH to about 90% RH, from about 40% RH to about 80% RH, or from about 50% RH to about 70% RH. Form I may be regenerated from Form II by heating in aqueous ethanol, isolation, drying, and humidification as describe elsewhere herein in connection with the preparation of Form I.

In some embodiments, Formula (I) bis-hydrochloride polymorph Form III may be prepared from Form I. In some such embodiments, Form I Formula (I) bis-hydrochloride salt is combined with methanol and IPA followed by heating, cooling and drying to generate Form II. The concentration of Form I in methanol/IPA is suitably from about 5 g/L to about 100 g/L, from about 10 g/L to about 50 g/L, or from about 10 g/L to about 30 g/L. The volume ratio of methanol to IPA is suitably from about 1.5:1 to about 0.25:1, from about 1:1 to about 0.5:1, or from about 0.75:1 to about 0.5:1. The temperature is suitably at least 60° C., or reflux. The admixture is then cooled and aged with stirring, such as at less than about 30° C. for at least an hour, and the Formula (I) bis-hydrochloride polymorph Form III is isolated, such as by filtration. The Form III polymorph is dried under vacuum at a suitable temperature, such as from about 40° C. to about 60° C. The dried solids may optionally be milled or ground. The dried solid is then exposed to air comprising water vapor to form hydrated Form III. The humidification conditions are suitably, from about 15° C. to about 50° C., or from about 15° C. to about 35° C., with exposure to air at from about 40% RH to about 90% RH, from about 40% RH to about 80% RH, or from about 50% RH to about 70% RH. Form I may be regenerated from Form III by heating in aqueous ethanol, isolation, drying, and humidification as describe elsewhere herein in connection with the preparation of Form I.

In some embodiments, Formula (I) bis-hydrochloride polymorph Form IV may be prepared from Form I. In some such embodiments, Form I Formula (I) bis-hydrochloride salt is combined with DMF followed by heating to form a solution, cooling and drying to generate Form IV. The concentration of Form I in DMF is suitably from about 25 g/L to about 250 g/L, from about 50 g/L to about 150 g/L, or from about 75 g/L to about 125 g/L. A solution is formed at a temperature of suitably at least 130° C., or reflux, to form a solution. The admixture is then cooled and aged with stirring, such as at less than about 30° C. for at least an hour. Seed crystals may be optionally added, such as during or after cooling. The Formula (I) bis-hydrochloride polymorph Form IV is isolated, such as by filtration. The Form IV polymorph is dried under vacuum at a suitable temperature, such as from about 40° C. to about 60° C. The dried solids may optionally be milled or ground. Form I may be regenerated from Form IV by heating in aqueous ethanol, isolation, drying, and humidification as describe elsewhere herein in connection with the preparation of Form I.

In some embodiments, Formula (I) bis-hydrochloride polymorph Form VI may be prepared from Form I. In some such embodiments, Form I Formula (I) bis-hydrochloride salt is dried under vacuum at a suitable temperature, such as from about 40° C. to about 60° C. The dried solids may optionally be milled or ground. In some aspects, Form I may be regenerated from Form VI by water hydration at humidification conditions suitably, from about 15° C. to about 35° C. with exposure to air at from about 40% RH to about 90% RH, from about 40% RH to about 80% RH, or from about 50% RH to about 70% RH. In some other aspects, Form I may be regenerated from Form VI by water hydration at humidification conditions suitably, from about 15° C. to about 30° C. with exposure to air at from about 10% RH to about 50% RH, or from about 10% RH to about 30% RH for a period of at least one day.

In some embodiments, amorphous Formula (I) bis-hydrochloride may be prepared crystalline Formula (I) bis-hydrochloride salt (e.g., Form I). The bis-hydrochloride salt is combined with DMSO at a concentration of from about 50 g/L to about 400 g/L, from about 100 g/L to about 300 g/L, or from about 150 g/L to about 250 g/L followed by heating with mixing to at least 100° C., at least 110° C. or at least 120° C. to form a solution. The solution is cooled to less than 35° C. followed by addition of an anti-solvent (e.g., acetone) to form a slurry of amorphous Formula (I) bis-hydrochloride salt. The volume ratio of acetone to DMSO is suitably at least 0.5:1, at least 1:1 or at least 2:1. The amorphous Formula (I) bis-hydrochloride salt is isolated, such as by filtration and dried under vacuum at a suitable temperature, such as from about 40° C. to about 60° C. The dried solids may optionally be milled or ground.

In some embodiments, crystalline Formula (I) bis-hydrogensulfate salt may be prepared from Formula (I) free base. In such embodiments, Formula (I) free base is combined with an alcohol solvent (e.g., methanol) to form an admixture at a suitable concentration of from about 10 g/L to about 150 g/L, from about 20 g/L to about 100 g/L, or from about 25 g/L to about 75 g/L. In some aspects, the methanol is aqueous methanol having a methanol content of from about 70% to about 90%, such as about 80%. Sulfuric acid is added to the admixture to form an admixture at an equivalent ratio of acid to Formula (I) free base as described elsewhere herein, such as from about 2 to about 3, from about 2 to about 2.5, or from about 2.2 to about 2.3. In some aspects, the reaction may be conducted at ambient temperature. The admixture is stirred and held for a time sufficient to essentially complete the conversion of Formula (I) free base to solid Formula (I) bis-hydrogensulfate salt in suspension. Formula (I) bis-hydrogensulfate salt is isolated, such as by filtration, and dried under vacuum at a suitable temperature, such as from about 40° C. to about 60° C. The dried solids may optionally be milled or ground.

In some embodiments, crystalline Formula (I) bis-p-toluenesulfonate salt Form A may be prepared from Formula (I) free base. In such embodiments, Formula (I) free base is combined with acetone to form an admixture at a suitable concentration of from about 10 g/L to about 150 g/L, from about 20 g/L to about 100 g/L, or from about 25 g/L to about 75 g/L. p-Toluenesulfonic acid is added to the admixture to form an admixture at an equivalent ratio of acid to Formula (I) free base as described elsewhere herein, such as from about 2 to about 3, from about 2 to about 2.5, or from about 2.2 to about 2.3. In some aspects, the reaction may be conducted at ambient temperature. The admixture is stirred and held for a time sufficient to essentially complete the conversion of Formula (I) free base to solid crystalline Formula (I) bis-p-toluenesulfonate salt Form A in suspension, the salt is isolated, such as by filtration, and dried under vacuum at a suitable temperature, such as from about 40° C. to about 60° C. The dried solids may optionally be milled or ground.

In some embodiments, crystalline Formula (I) bis-p-toluenesulfonate salt Form B may be prepared from Formula (I) free base. In such embodiments, Formula (I) free base is combined with ACN to form an admixture at a suitable concentration of from about 10 g/L to about 150 g/L, from about 20 g/L to about 100 g/L, or from about 25 g/L to about 75 g/L. p-toluenesulfonic acid is added to the admixture to form an admixture at an equivalent ratio of acid to Formula (I) free base as described elsewhere herein, such as from about 2 to about 3, from about 2 to about 2.5, or from about 2.2 to about 2.3. In some aspects, the reaction may be conducted at ambient temperature. The admixture is stirred and held for a time sufficient to essentially complete the conversion of Formula (I) free base to solid crystalline Formula (I) bis-p-toluenesulfonate salt Form B in suspension, the salt is isolated, such as by filtration, and dried under vacuum at a suitable temperature, such as from about 40° C. to about 60° C. The dried solids may optionally be milled or ground.

In some embodiments, crystalline Formula (I) bis-ethanesulfonate salt may be prepared from Formula (I) free base. In such embodiments, Formula (I) free base is combined with an alcohol solvent (e.g., ethanol) to form an admixture at a suitable concentration of from about 10 g/L to about 150 g/L, from about 20 g/L to about 100 g/L, or from about 25 g/L to about 75 g/L. Ethanesulfonic acid is added to the admixture to form an admixture at an equivalent ratio of acid to Formula (I) free base as described elsewhere herein, such as from about 2 to about 3, from about 2 to about 2.5, or from about 2.2 to about 2.3. In some aspects, the reaction may be conducted at a temperature of greater than about 70° C., or at reflux. The admixture is stirred and held at a temperature of less than about 35° C. for a time sufficient to essentially complete the conversion of Formula (I) free base to solid crystalline Formula (I) ethanesulfonate salt in suspension, the salt is isolated, such as by filtration, and dried under vacuum at a suitable temperature, such as from about 40° C. to about 60° C. The dried solids may optionally be milled or ground.

In some embodiments, crystalline Formula (I) bis-methanesulfonate salt may be prepared from Formula (I) free base. In such embodiments, Formula (I) free base is combined with an alcohol solvent (e.g., ethanol) to form an admixture at a suitable concentration of from about 10 g/L to about 150 g/L, from about 20 g/L to about 100 g/L, or from about 25 g/L to about 75 g/L. Methanesulfonic acid is added to the admixture to form an admixture at an equivalent ratio of acid to Formula (I) free base as described elsewhere herein, such as from about 2 to about 3, from about 2 to about 2.5, or from about 2.2 to about 2.3. In some aspects, the reaction may be conducted at a temperature of greater than about 70° C., or at reflux. The admixture is stirred and held at a temperature of less than about 35° C. for a time sufficient to essentially complete the conversion of Formula (I) free base to solid crystalline Formula (I) methanesulfonate salt in suspension, the salt is isolated, such as by filtration, and dried under vacuum at a suitable temperature, such as from about 40° C. to about 60° C. The dried solids may optionally be milled or ground.

Medical Use and Pharmaceutical Compositions

As disclosed in WO 2013/100632, the compound of Formula (I) has been shown to be useful for prevention or treatment of abnormal cell growth diseases caused by abnormal activation of a protein kinase.

In one embodiment the invention further provides a salt of the compound of Formula (I), a crystalline form of a salt of the compound of Formula (I), or a crystalline form of a free base of the compound of Formula (I) as described herein for use in the prevention or treatment of abnormal cell growth diseases by inhibiting the activity of the protein kinase.

In a further embodiment the invention provides a method for the prevention or treatment of abnormal cell growth diseases comprising administering to a patient in need thereof a therapeutically effective amount of a salt of the compound of Formula (I) or a crystalline form of a salt of the compound of Formula (I) as described herein.

In a further embodiment the protein kinase is selected from ALK, AMPK, Aurora A, Aurora B, Aurora C, Ax1, Blk, Bmx, BTK, CaMK, CDK2/cyclinE, CDK5/p25, CHK1, CK2, A-Raf, B-Raf, C-Raf, DDR1, DDR2, DMPK, EGFR1, Her2, Her4, EphA1, EphB1, FAK, FGFR2, FGFR3, FGFR4, Flt-1, Flt-3, Flt-4, Fms (CSF-1), Fyn, GSK3beta, HIPK1, IKKbeta, IGFR-1R, IR, Itk, JAK2, JAK3, KDR, Kit, Lck, Lyn, MAPK1, MAPKAP-K2, MEK1, Met, MKK6, MLCK, NEK2, p70S6K, PAK2, PDGFR alpha, PDGFR beta, PDK1, Pim-1, PKA, PKBalpha, PKCalpha, Plk1, Ret, ROCK-I, Rsk1, SAPK2a, SGK, Src, Syk, Tie-2, Tec, Trk and ZAP-70.

In a further embodiment the abnormal cell growth disease to be prevented or treated is selected from gastric cancer, lung cancer, liver cancer, colorectal cancer, small intestine cancer, pancreatic cancer, brain cancer, bone cancer, melanoma, breast cancer, sclerosing adenosis, uterine cancer, cervical cancer, head and neck cancer, esophagus cancer, thyroid cancer, parathyroid cancer, renal cancer, sarcoma, prostate cancer, urethral cancer, bladder cancer, blood cancer, lymphoma, fibroadenoma, inflammation, diabetes, obesity, psoriasis, rheumatoid arthritis, hemangioma, acute and chronic kidney disease, coronary restenosis, autoimmune diseases, asthma, neurode-generative diseases, acute infection and ocular diseases caused by angiogenesis.

In this embodiment, the salt of the compound of Formula (I) or the crystalline form of the salt of the compound of Formula (I) may be used for the preparation of a pharmaceutical composition for preventing or treating the abnormal cell growth diseases caused by abnormal activation of a protein kinase. The pharmaceutical composition may be used to prevent or treat the same diseases as described for the salt or crystalline forms of the salt hereinbefore.

Accordingly, the present invention provides a pharmaceutical composition containing a salt of the compound of Formula (I), preferably in crystalline form, or a crystalline form of a free base of the compound of Formula (I) and at least one pharmaceutically acceptable carrier or diluent. The pharmaceutical composition may be used for the prevention or treatment of the abnormal cell growth disease caused by abnormal activation of a protein kinase.

The administration dose of the salt of the compound of Formula (I), preferably in crystalline form or a pharmaceutical composition containing the same may vary depending on the subject to be treated, severity of illness or health state of the subject, administration rate, and physician's decision, but it may be conventionally administered to a human subject having a body weight of, for instance, 70 kg, via an oral or parenteral administration route in an amount of from 10 mg to 2,000 mg as a free base based on the compound of Formula (I), preferably in an amount of 50 mg to 1,000 mg, 1 to 4 times daily or on an on/off schedule. In some cases, it may be more appropriate to administer a lower dosage than that mentioned above, a higher dosage than the above may be administered if it does not cause harmful side effects, and in the case when a significantly larger dosage is to be administered, the administration may be performed daily by several divided doses with a lesser dosage per administration.

The pharmaceutical composition according to the present invention may be prepared in various formulations for oral administration according to the conventional methods, such as, tablets, pills, powders, capsules, syrups, emulsions, microemulsions, or for parenteral administration.

The pharmaceutical composition may contain any conventional non-toxic, pharmaceutically acceptable excipients including carriers, diluents, adjuvants, and vehicles.

When the pharmaceutical composition according to the present invention is prepared as a formulation for oral administration, the carrier to be used may include, for instance and without limitation, cellulose, calcium silicate, corn starch, lactose, sucrose, dextrose, calcium phosphate, stearic acid, magnesium stearate, calcium stearate, gelatin, talc, surfactant, suspending agents, emulsifying agents, diluents, and combinations thereof. Additionally, when the pharmaceutical composition is prepared as a formulation for oral administration, the diluents to be used may include, for instance and without limitation, lactose, mannitol, saccharide, microcrystalline cellulose, cellulose derivative, corn starch, and combinations thereof. Formulations for oral administration may also include, for instance and without limitation, polymers (for instance hydrophilic polymers such as polyvinylpyrrolidone), antioxidants, preservatives, wetting agents, lubricating agents, glidants, processing aids, granulating agents, dispersing agents, colorants, flavoring agents, Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed and optionally are formulated so as to provide slow or controlled release of the active ingredient therefrom.

When the pharmaceutical composition according to the present invention is prepared as a formulation for injections, the carrier to be used may include, for instance and without limitation, water, saline, an aqueous glucose solution, an aqueous sugar-like solution, alcohols, glycols (e.g., polyethylene glycol 400), ethers, oils, fatty acids, fatty acid esters, glycerides, surfactants, suspending agents, emulsifying agents, and combinations thereof.

When the binding target is located in the brain, certain embodiments of the invention provide for forms of the compound of Formula (I) capable of traversing the blood-brain barrier. Certain neurodegenerative diseases are associated with an increase in permeability of the blood-brain barrier, such that the compound of Formula (I) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the compound of Formula (I) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers®, Guildford.

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting the compound of Formula (I) across the blood-brain barrier include, but are not limited to, encapsulating the compound of Formula (I) in liposomes that are coupled to antibody binding fragments that bind to receptors on the vascular endothelium of the blood-brain barrier (see, e.g., U.S. Patent Application Publication No. 2002/0025313), and coating the compound of Formula (I) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting the compound of Formula (I) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating the compound of Formula (I) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the pharmaceutical compositions can be administered continuously by infusion into the fluid reservoirs of the CNS, although bolus injection may be acceptable. The pharmaceutical compositions can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the pharmaceutical compositions can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Hereinafter, the present invention will be described in more detail with reference to the following Examples. However, these Examples are for illustrative purposes only, and the invention is not intended to be limited by these Examples.

Analysis Apparatus and Method of PXRD

PXRD analyses of samples were performed in the range from 3° 2θ to 40° 2θ using a D8 Advance (Bruker ASX, Germany) analyzer. When the amount of a given sample was less than 100 mg, about 5 mg to 10 mg of the sample was gently compressed on a glass slide which was fitted into a sample holder. When the amount of a given sample was greater than 100 mg, about 100 mg of the sample was gently compressed in a plastic sample holder so that the sample surface became flat and positioned immediately on top of the sample holder level.

The measurement was performed as follows. Anode material (Kα): Cu Kα (1.54056 Å). Scan range: 3° to 40°. Generator settings: 100 mA, 40.0 kV. Scan speed: 1 sec/step. Diver slit: 0.3°. Anti-scatter slit: 0.3°. Temperature: 20° C. Step size: 0.02° 2θ. Rotation: use. Goniometer radius: 435 mm.

Analysis Apparatus and Method of Differential Scanning Calorimetry (DSC)

Differential scanning calorimeter (DSC) analysis was performed in as STA-1000 (Scinco, Korea) at 30° C. to 350° C. A sample in an amount of 5 mg to 10 mg was weighed and added into an aluminum DSC fan, and the fan was sealed with a perforated aluminum lid in a non-sealing manner. Then, the sample was heated at a scan speed of 10° C./min from 30° C. to 350° C., and the heat flow reaction generated was monitored in a DSC.

Analysis Apparatus and Method of Dynamic Vapor Sorption (DVS)

Dynamic vapor sorption (DVS) analysis was performed in a DVS advantage (Surface measurement system, United Kingdom) analyzer at 25° C. with a relative humidity of 0% to 90%. A sample in an amount of 10 mg was placed into a wire-mesh vapor sorption balance pan and then attached to a DVS advantage dynamic vapor sorption balance via surface measurement systems. The sample was subjected to a ramping profile from 0% to 90% relative humidity at 10% increments, maintaining the sample at each step until a stable weight had been achieved (99.5% step completion). Upon completion of the sorption cycle, the sample was dried using the same process while maintaining a relative humidity of 0%. The changes in the sample weight during the adsorption/desorption cycle (repeated 3 times) were recorded and the hygroscopicity of the sample was measured. DVS isotherm diagrams are presented in FIGS. 1, 3, 6, 10, 13, 16 and 19 where Target PP (%) refers to relative humidity, "SORP" refers to adsorption and "DESORP" refers to desorption.

EXAMPLES: PREPARATION OF CRYSTALLINE FORMS OF SALTS OF A COMPOUND OF FORMULA (I)

Example 1: Salt Screening of Formula (I)

Various salt forms of Formula (I) were prepared from Formula (I) free base and characterized by water solubility, PXRD, DSC, DVS and hygroscopicity.

Example 1A: Evaluation of pKa Values of Formula (I) Bis-Hydrochloride Salt

Formula (I) bis-hydrochloride salt was prepared as described below. pKa values were measured with the GLpKa method and were determined to be 3.86 (pKa1), 4.73 (pKa2), and 10.30 (pKa3). Based on these pKa values, Formula (I) is believed to be weakly basic compound.

Example 1B: Preparation and Evaluation of Formula (I) Acid Salts

For each Example 1B salt, a mixture of 40 mL (20 v/w) of a suitable solvent and 2 g Formula (I) free base was formed with agitation at room temperature. The indicated acid (2.2 eq.) was added to the mixture and salt formation was monitored by visual check. The resulting solid bis-acid salt was stirred for 24 hr at room temperature then filtered, and washed with a suitable solvent.

Formula (I) bis-hydrochloride salt was prepared and characterized by PXRD, DSC and DVS.

Figure 2:
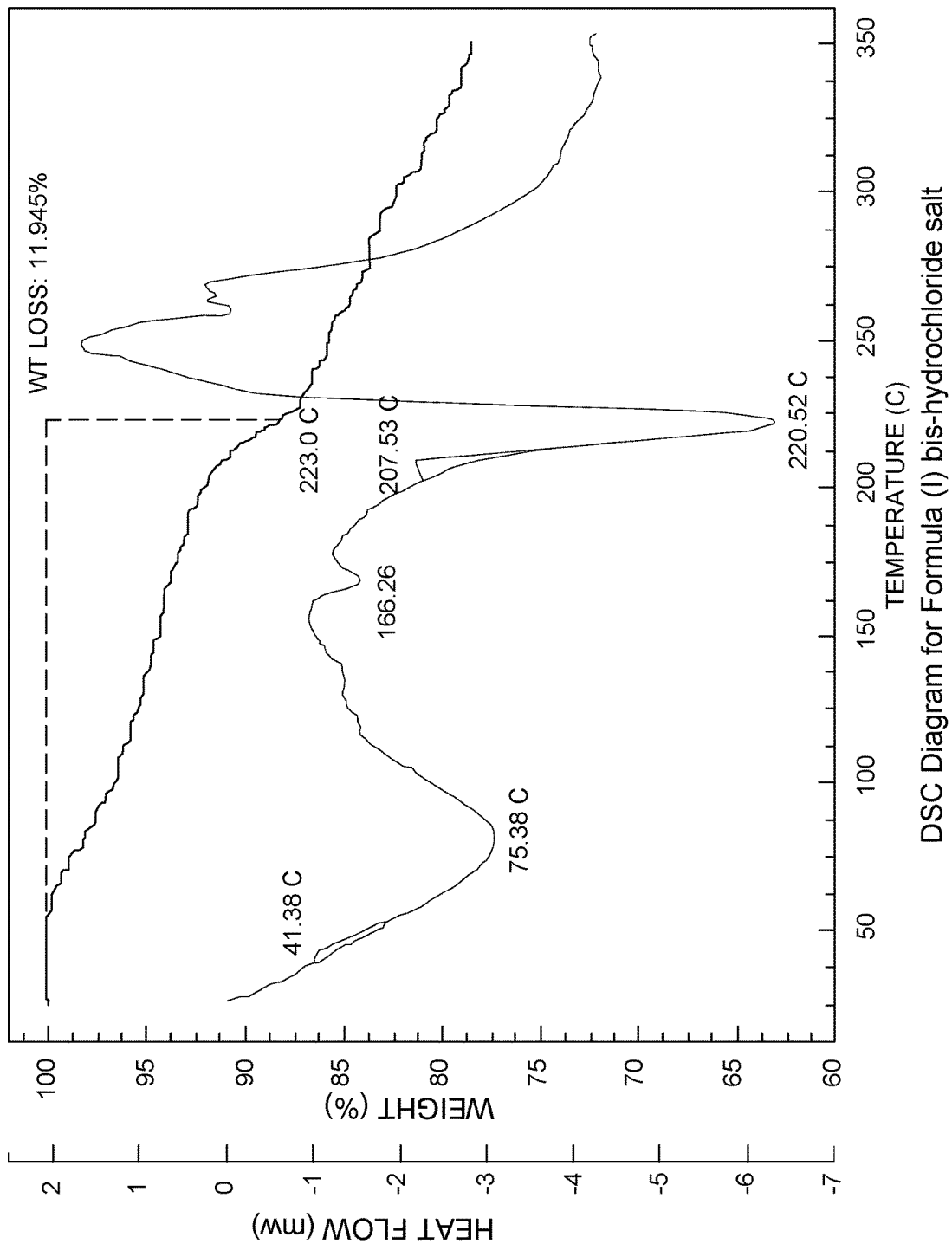
FIG. 2 shows a differential scanning calorimetry ("DSC") diagram for crystalline Formula (I) bis-hydrochloride salt.
Figure 3:
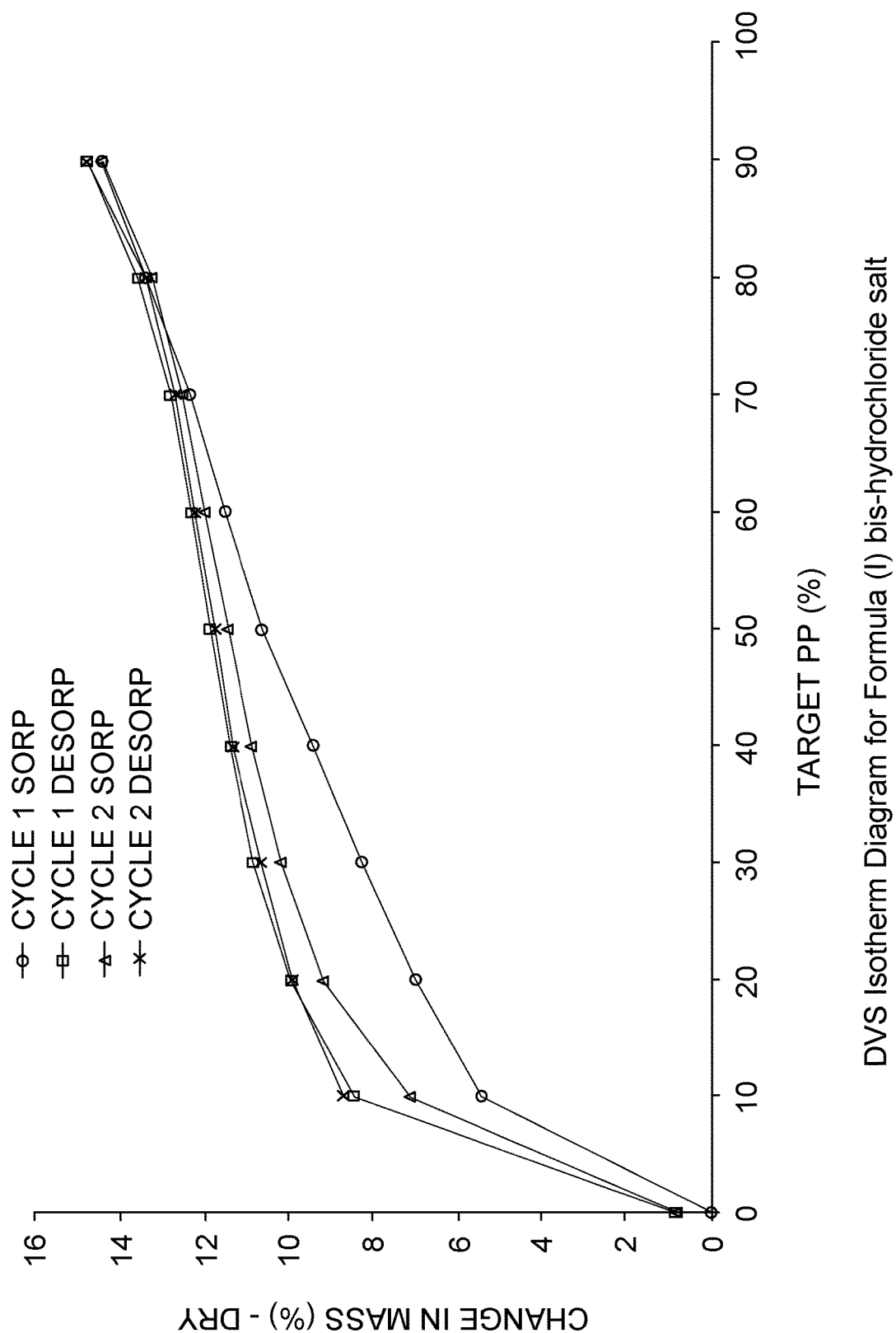
FIG. 3 shows a dynamic vapor sorption ("DVS") diagram for crystalline Formula (I) bis-hydrochloride salt.
Figure 34:
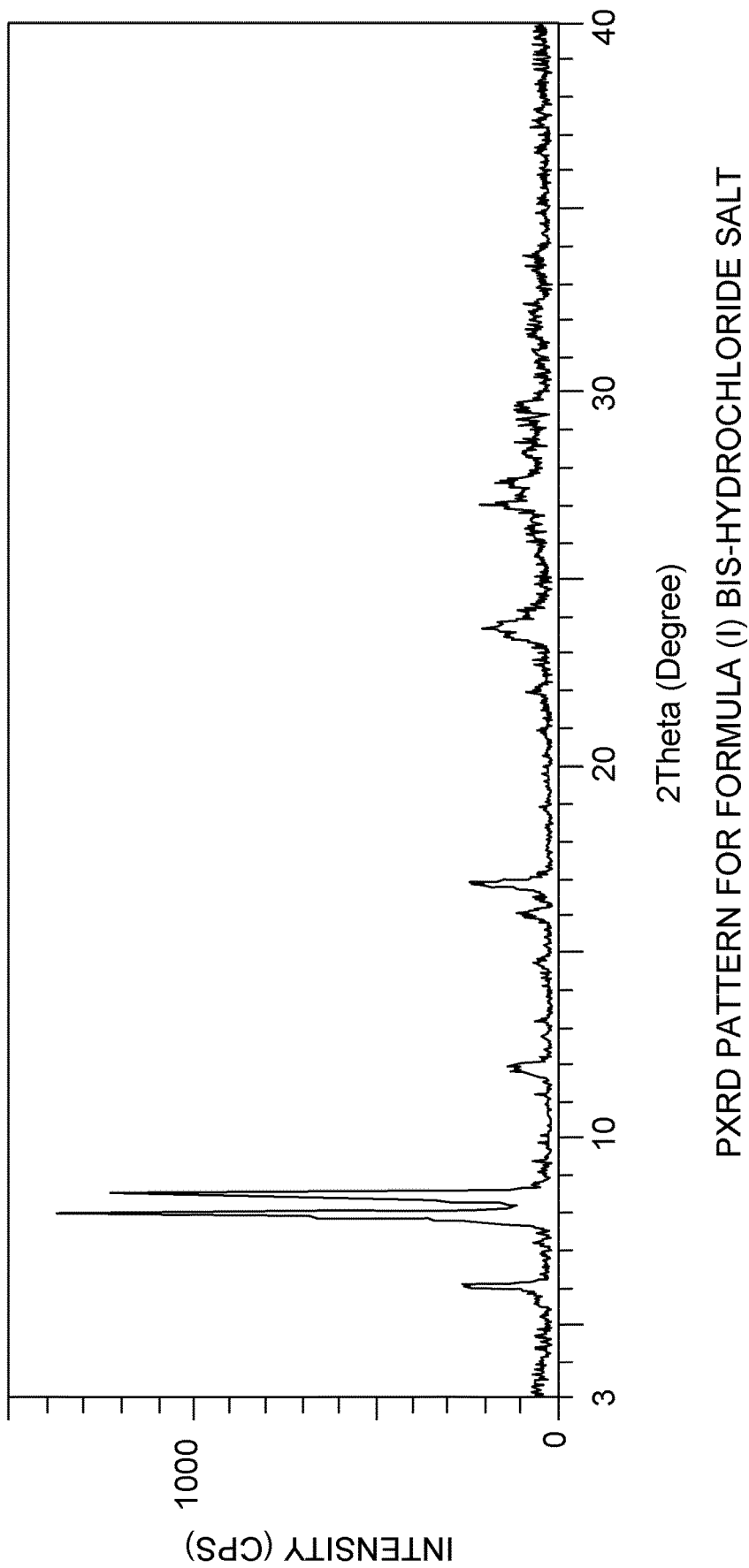
FIG. 34 shows a PXRD pattern for crystalline Formula (I) bis-hydrochloride salt.

The bis-hydrochloride salt PXRD results are indicated in FIG. 34 and Table 1, the DSC results are indicated in FIG. 2, and the DVS results are indicated in FIG. 3. In Table 1, diffraction angles are reported in degrees 2θ, d Values are reported in Angstroms and Intensity is reported in counts per second.

TABLE 1

| 2θ (±0.2) | d Value (Å) | Intensity | I/I$_o$ (%) |
|---|---|---|---|
| 5.99 | 14.75 | 250 | 18.1 |
| 7.14 | 12.37 | 55 | 4 |
| 7.92 | 11.15 | 1380 | 100 |
| 8.47 | 10.43 | 1235 | 89.5 |
| 11.88 | 7.44 | 130 | 9.4 |
| 13.15 | 6.73 | 50 | 3.6 |
| 16.04 | 5.52 | 110 | 8 |
| 16.84 | 5.26 | 235 | 17 |
| 22.00 | 4.04 | 80 | 5.8 |
| 23.69 | 3.75 | 205 | 14.9 |
| 27.01 | 3.30 | 210 | 15.2 |
| 27.65 | 3.22 | 170 | 12.3 |
| 29.75 | 3.00 | 90 | 6.5 |

2θ: diffraction angle; d: distance between crystal faces; I/I$_o$(%): relative intensity (I indicates the intensity of each peak; I$_o$ indicates the intensity of the highest peak)

The hygroscopicity of the Formula (I) bis-hydrochloride salt was measured at 25° C. and 75% RH, and the water content was determined to increase from 6.2% to 11.7%.

Formula (I) bis-hydrogensulfate salt was prepared and characterized by PXRD, DSC and DVS.

Figure 5:
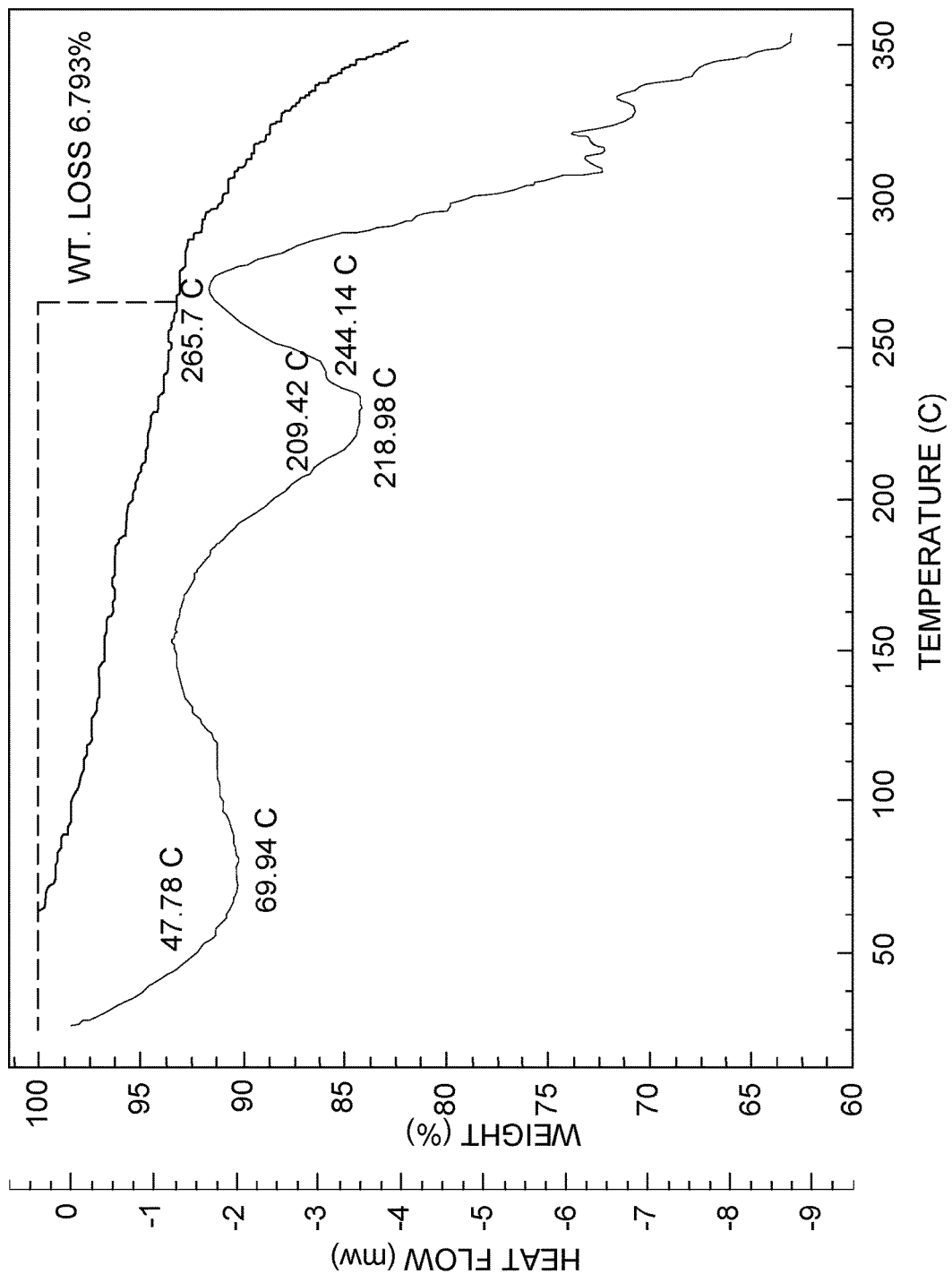
FIG. 5 shows a DSC diagram for crystalline Formula (I) bis-hydrogensulfate salt.
Figure 6:
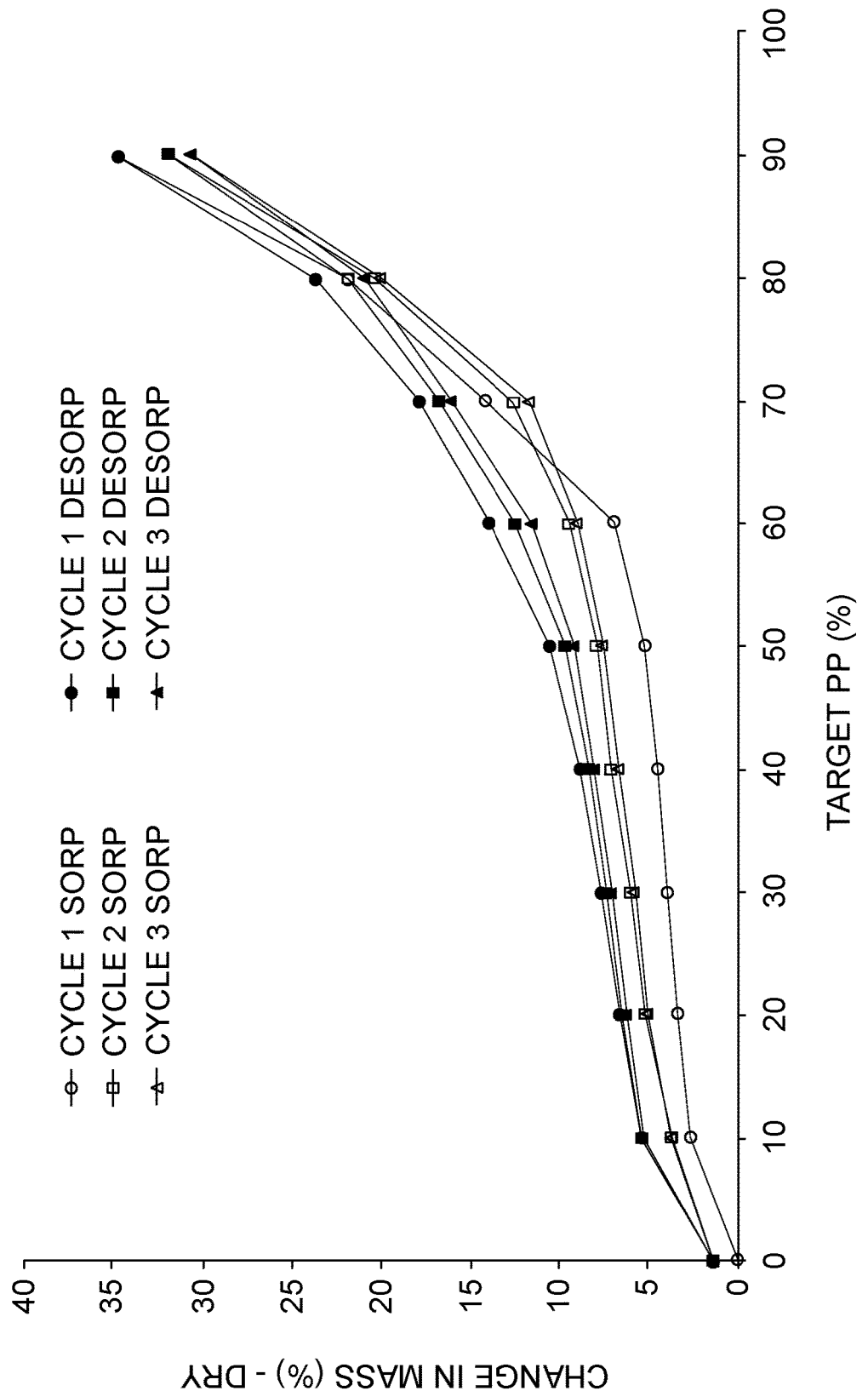
FIG. 6 shows a DVS diagram for crystalline Formula (I) bis-hydrogensulfate salt.

The bis-hydrogensulfate salt PXRD results are indicated in FIG. 4 and Table 2, the DSC results are indicated in FIG. 5, and the DVS results are indicated in FIG. 6.

TABLE 2

| 2θ (±0.2) | d Value (Å) | Intensity | I/I$_o$ (%) |
|---|---|---|---|
| 4.41 | 20.01 | 125 | 35.2 |
| 6.70 | 13.18 | 295 | 83.1 |
| 8.12 | 10.87 | 355 | 100 |
| 8.73 | 10.12 | 115 | 32.4 |
| 10.11 | 8.74 | 255 | 71.8 |
| 12.84 | 6.89 | 85 | 23.9 |
| 14.89 | 5.95 | 105 | 29.6 |
| 15.34 | 5.77 | 125 | 35.2 |
| 16.21 | 5.46 | 115 | 32.4 |

TABLE 2-continued

| 2θ (±0.2) | d Value (Å) | Intensity | I/I₀ (%) |
|---|---|---|---|
| 16.56 | 5.35 | 155 | 43.7 |
| 18.85 | 4.70 | 95 | 26.8 |
| 20.32 | 4.37 | 155 | 43.7 |
| 21.22 | 4.18 | 125 | 35.2 |
| 22.51 | 3.95 | 115 | 32.4 |

The hygroscopicity of the Formula (I) bis-hydrogensulfate salt was measured at 25° C. and 75% RH, and the water content was determined to increase from 2.6% to 17.1%.

Formula (I) bis-methanesulfonic acid salt was prepared and characterized by PXRD, DSC and DVS.

The bis-methanesulfonic acid salt PXRD results are indicated in FIG. 7 and in Table 3.

TABLE 3

| 2θ (±0.2) | d Value (Å) | Intensity | I/I₀ (%) |
|---|---|---|---|
| 5.91 | 14.95 | 120 | 50 |
| 7.34 | 12.04 | 90 | 37.5 |
| 7.86 | 11.23 | 240 | 100 |
| 11.68 | 7.57 | 70 | 29.2 |
| 13.72 | 6.45 | 65 | 27.1 |
| 15.64 | 5.66 | 125 | 52.1 |

Formula (I) bis-benzenesulfonic acid salt was prepared and characterized by PXRD, DSC and DVS.

Figure 8:
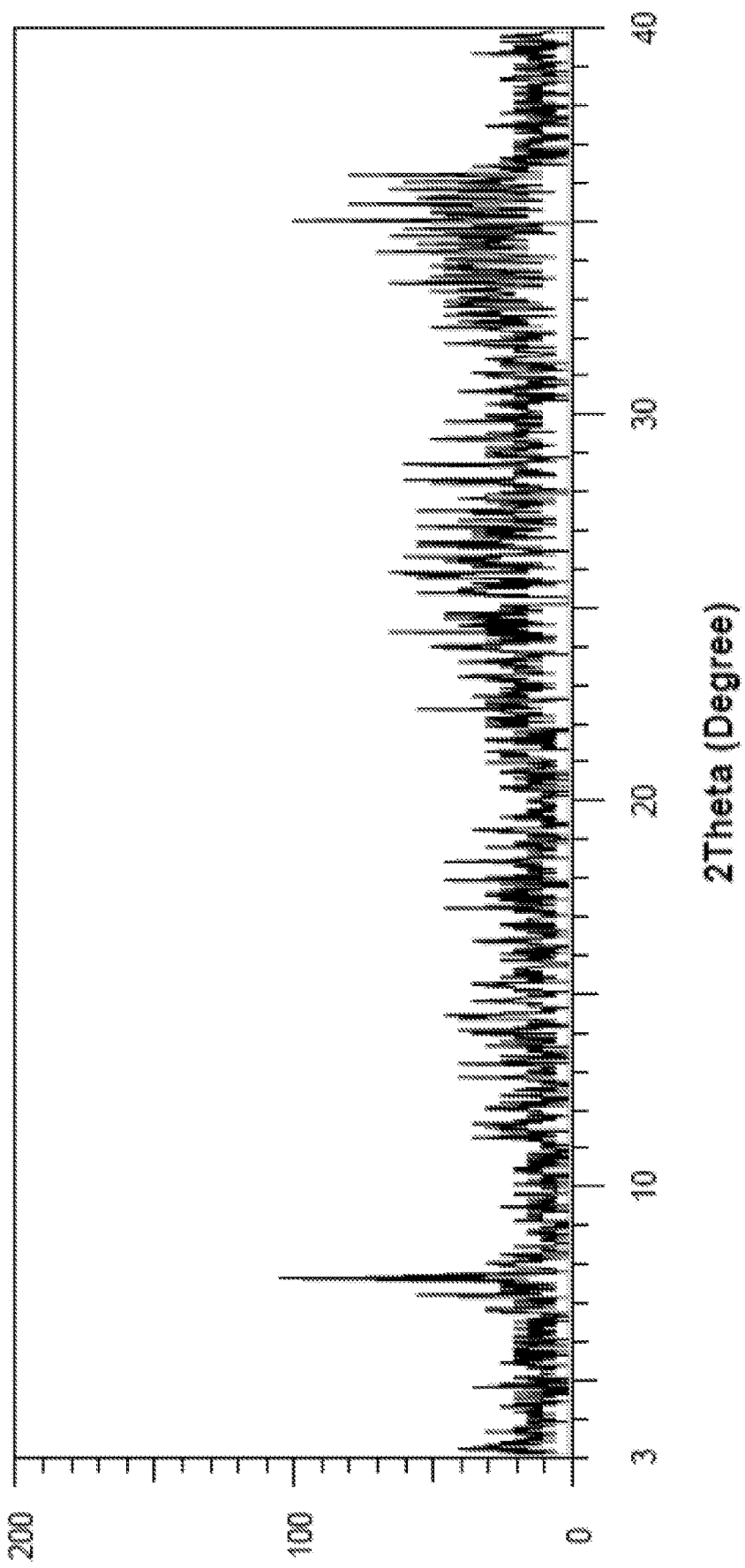
FIG. 8 shows a PXRD pattern for crystalline Formula (I) bis-benzenesulfonate salt.

The bis-benzenesulfonic acid salt PXRD results are indicated in FIG. 8. Characteristic peaks in degrees 2θ±0.2 are noted at 7.17 and 7.58.

Formula (I) bis-hydrobromide salt was prepared and characterized by PXRD, DSC and DVS.

Figure 9:
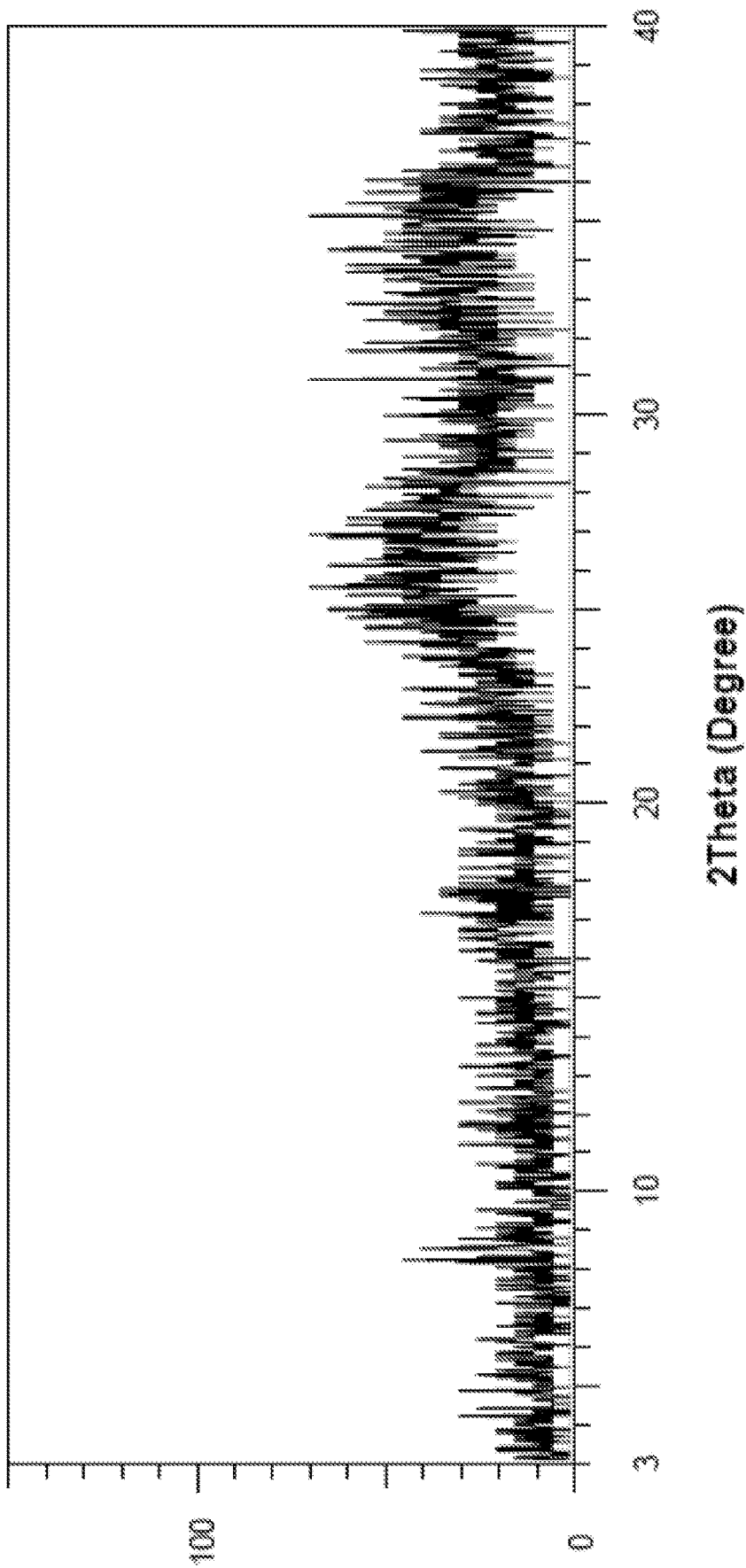
FIG. 9 shows a PXRD pattern for Formula (I) bis-hydrobromide salt.

The bis-hydrobromide salt PXRD results are indicated in FIG. 9 which indicate that the salt is amorphous.

The water content, solubility in water (mg/mL), appearance, salt yield (%) and PXRD results for each of the salts of Example 1B are summarized in Table 4 where "MsOH" refers to methane sulfonic acid; "BsOH" refers to benzenesulfonic acid; "OW" refers to off-white; "W" refers to white; "Cryst" refers to crystalline; and "Amorph" refers to amorphous. Solubility was measured by HPLC according to KP, USP and EP general chapters. In summary the salts were generally practically insoluble in water, very slightly soluble in pH 1.6 buffer, and practically insoluble in buffers having a pH in excess of 3.

TABLE 4

| Acid | HCl | H₂SO₄ | MsOH | BsOH | HBr |
|---|---|---|---|---|---|
| Appearance | OW | W | OW | OW | OW |
| Yield (%) | 95 | 89 | 56 | 25 | 60 |
| PXRD | Cryst | Cryst | Cryst | Cryst | Amorph |
| H₂O Solubility (mg/mL) | 0.12 | 0.16 | 0.05 | 0.03 | 0.05 |
| Water Content (%) | 6.2 | 2.6 | 2.1 | 0.9 | 2.9 |

Example 2: Physicochemical Properties of Crystalline Formula (I) Bis-Hydrochloride Polymorph Form I Formula (I) bis-hydrochloride salt polymorph Form I was prepared by the method of Example 3.

Physicochemical properties of the Formula (I) bis-hydrochloride salt Form I were measured including appearance, hygroscopicity, pH of an aqueous solution, melting point/ thermal analysis, dissociation constant, partition coefficient and form (i.e., crystalline or amorphous).

Appearance was evaluated according to the test detailed in The Korean Pharmacopoeia, 10th Edition. The appearance was determined to be a pale brown or off-white powder.

Solubility was measured by HPLC according to KP, USP and EP general chapters. Formula (I) bis-hydrochloride salt was very slightly soluble in pH 1.2 and pH 2.0 buffer, and practically insoluble in buffer over pH 3.0 and water. Formula (I) bis-hydrochloride salt was freely soluble in dimethylsulfoxide ("DMSO"), sparingly soluble in methanol, very slightly soluble in ethanol, practically in soluble in dichloromethane, ACN, ethyl acetate, n-hexane, and ethyl ether. The results of solubility were same between HPLC test and observation test. The results of the solubility by HPLC test and observation test are shown in Table 5.

TABLE 5

| | Solubility | | |
|---|---|---|---|
| Solvent | mL/g | mg/mL | Observation |
| Water | 654940 | $1.5 \times 10^{-3}$ | Practically insoluble |
| pH 1.2 buffer | 3811 | 0.3 | Very slightly soluble |
| pH 2.0 buffer | 1688 | 0.6 | Very slightly soluble |
| pH 3.0 buffer | 42855 | $0.2 \times 10^{-1}$ | Practically insoluble |
| pH 4.0 buffer | 331069 | $0.3 \times 10^{-2}$ | Practically insoluble |
| pH 5.0 buffer | 10759731 | $0.9 \times 10^{-4}$ | Practically insoluble |
| pH 6.0 buffer | 9770999 | $0.1 \times 10^{-3}$ | Practically insoluble |
| pH 6.8 buffer | 11528283 | $0.9 \times 10^{-4}$ | Practically insoluble |
| pH 7.0 buffer | 16139597 | $0.6 \times 10^{-4}$ | Practically insoluble |
| pH 8.0 buffer | 21884199 | $0.5 \times 10^{-4}$ | Practically insoluble |
| Methanol | 58 | 17.4 | Sparingly soluble |
| Ethanol | 1316 | 0.8 | Very slightly soluble |
| Dichloromethane | 366289 | $2.7 \times 10^{-3}$ | Practically insoluble |
| Ethyl acetate | 356535 | $2.8 \times 10^{-3}$ | Practically insoluble |
| DMSO | 8 | 130.7 | Freely soluble |
| ACN | 113431 | $0.8 \times 10^{-2}$ | Practically insoluble |
| Ethyl ether | 522061 | $1.9 \times 10^{-3}$ | Practically insoluble |
| n-Hexane | 22316479 | $0.4 \times 10^{-4}$ | Practically insoluble |

Figure 10:
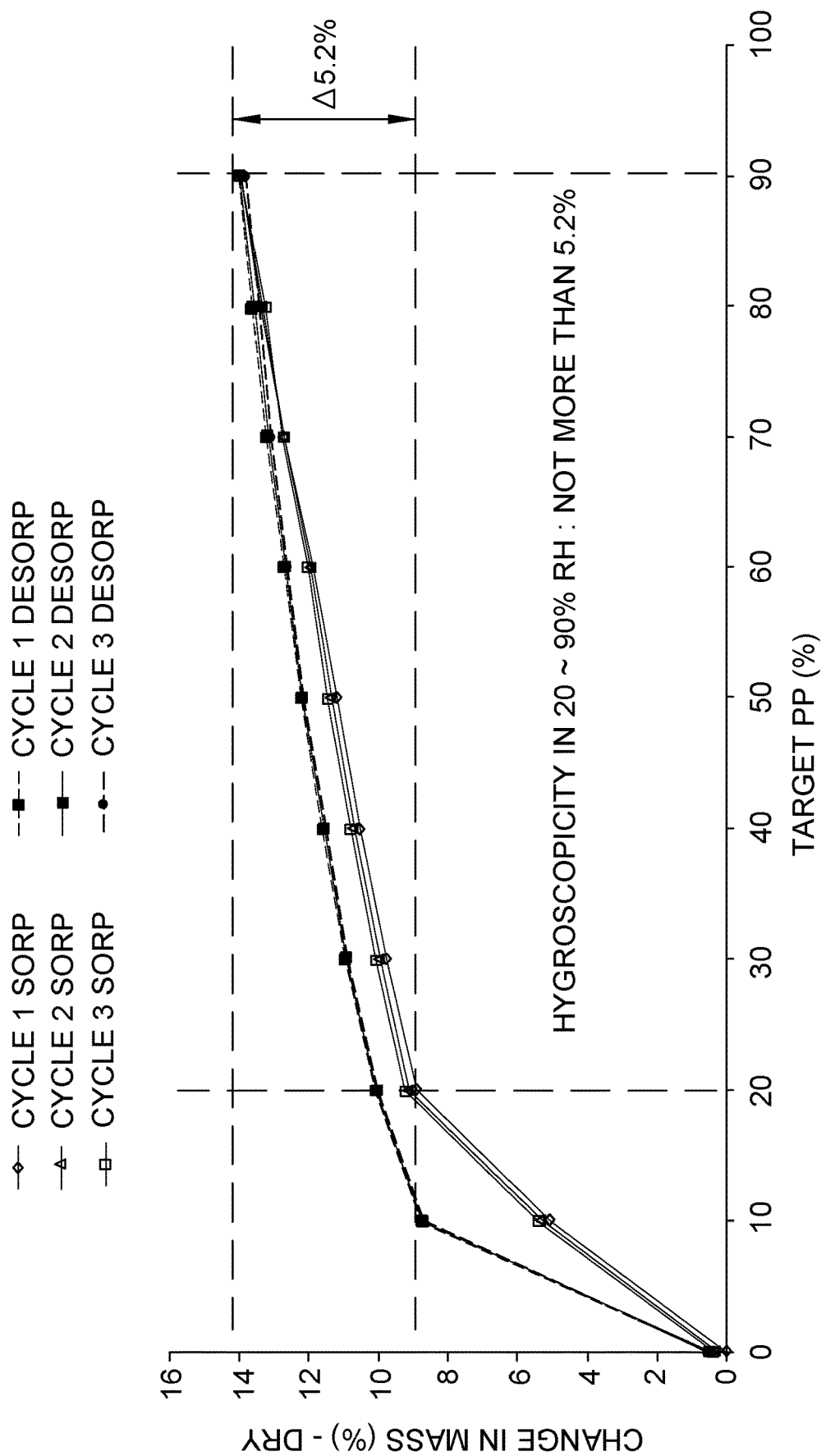
FIG. 10 shows a DVS diagram for Formula (I) bis-hydrochloride salt crystalline polymorph Form I.

Hygroscopicity was measured by DVS where the DVS curve for Formula (I) bis-hydrochloride was recorded in a DVS Advantage I analyzer (SMS, United Kingdom). The DVS was operated over 3 cycles for measurement of the surface adsorption effects of water, from 0% RH to 90% RH at 25°. FIG. 10 shows the moisture uptake behavior of Formula (I) bis-hydrochloride Form I.

The DVS result indicates a change of water content (%), by water absorption and desorption at 0% RH-90% RH. Water absorption occurred rapidly (about 9.4% from 0% RH to 20% RH) and then the water absorption increased to 14.1% from 20% RH to 90% RH. Water desorption slowly occurred to about 5.2% from 90% RH to 10% RH, and then the water desorption rapidly decreased to about 8.9% from 10% RH to ~0% RH. The water content results were reproducible results during the absorption-desorption process. It was confirmed the water absorption is about 14.1% from 0% RH to 90% RH. The DVS chart of Formula (I) bis-hydrochloride is shown in FIG. 10.

Aqueous solution pH was measured by preparing 0.01%, 0.1% and 1% aqueous solutions of Formula (I) bis-hydrochloride and then shaking the solution for 30 minutes at room temperature followed by filtration. The pH of the filtered aqueous solution was measured with a S2K713 Pocket pH meter (ISFETCOM, Japan) according to the method of the Korean Pharmacopoeia.

The pH for an aqueous solution of Formula (I) bis-hydrochloride (conc.=1%) was about 1.8 at room temperature. The pH decreased with concentration. The pH of a 0.1 mg/mL (0.01%) solution was 3.9; the pH of a 1 mg/mL (0.1%) solution was 2.6; and the pH of a 10 mg/mL (1%) solution was 1.8.

Melting point and thermal analysis was measured by DSC where the DSC thermogram of Formula (I) bis-hydrochloride was recorded in a STA S-1000 DSC (Scinco, Korea), operating at a rate of 10° C./min. The DSC curve was obtained in a standard aluminum cup, from 30° C. to 350° C.

Figure 11:
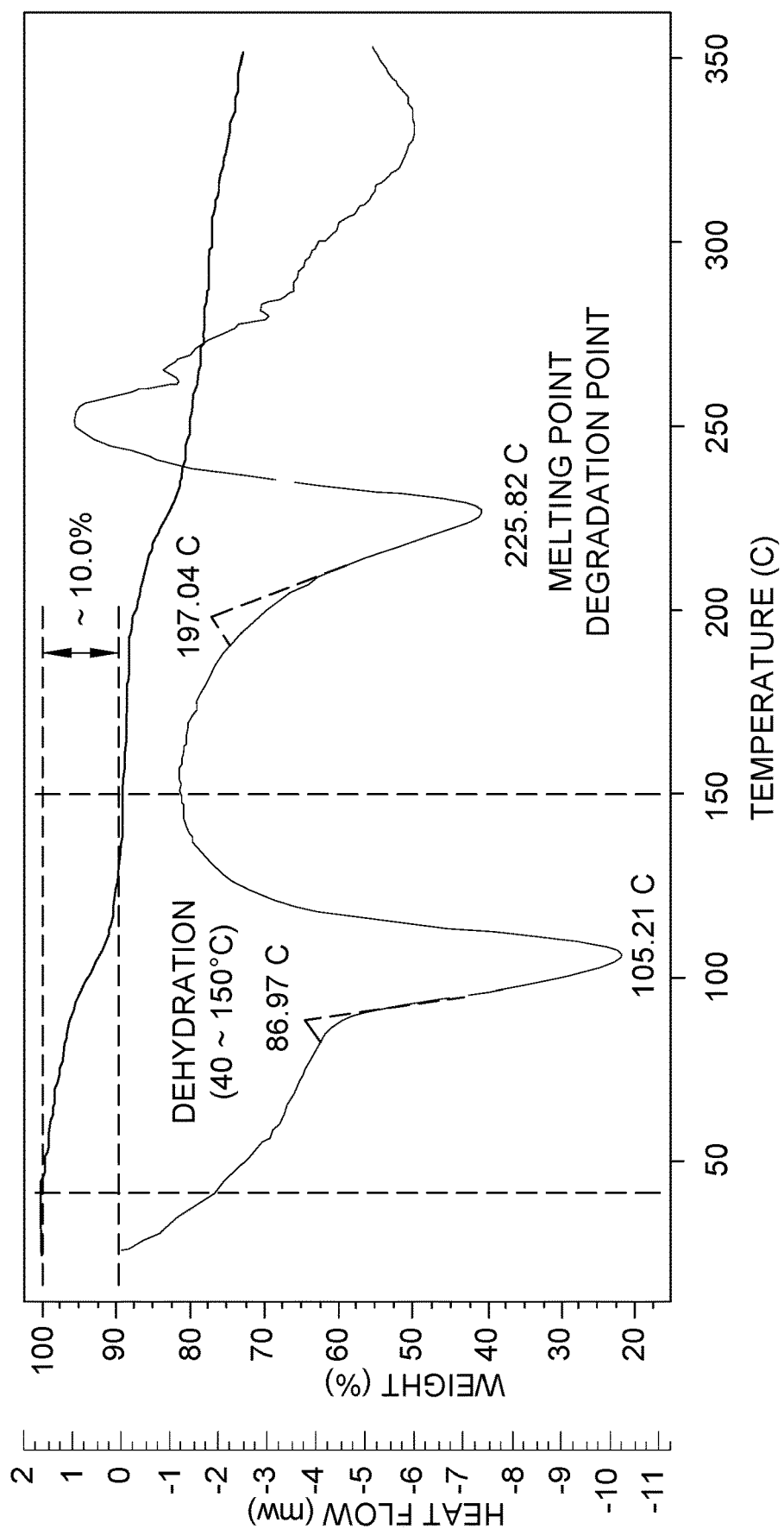
FIG. 11 shows a DSC diagram for Formula (I) bis-hydrochloride salt crystalline polymorph Form I.

DSC thermogram results indicate that the melting (degradation) point of Formula (I) bis-hydrochloride is 197° C. to 225° C. The weight loss and broad endothermic peak caused by volatile material was observed at 40° C. to 150° C., the other endothermic peak caused by melting and decomposition was observed at 197° C. (onset) to 225° C. (maximum). Formula (I) bis-hydrochloride decomposed at 230° C. to 233° C. by visual observation. The DSC plot is shown in FIG. 11.

Crystalline Formula (I) bis-hydrochloride polymorph Form I is believed to be a trihydrate. As indicated in FIG. 11, a weight loss in TGA/DSC testing of about 10% was observed between 40° C. and 150° C. that is due to water loss. The initial amount of water was confirmed by Karl-Fisher titration. It is believed that the amount of water lost in TGA/DSC testing generally corresponds to the theoretical amount of 8.92% water in the trihydrate. This conclusion was reached even though the water content in Formula (I) bis-hydrochloride salt production batches was higher (such as about 9 to 13% water) than the theoretical value (8.92%). Without being bound to any particular theory, it is believed that water content in excess of about 8.92% arises from excess moisture likely deriving from the moisturizing step used to obtain a trihydrate. One example of such a process is as follows: (i) filtration of Formula (I) bis-hydrochloride salt (as a trihydrate) precipitated in a final crystallization step; (ii) drying the filtered wet cake to remove residual organic solvents at elevated temperature (it is believed that a portion of water corresponding to the trihydrate is removed in this step); and (iii) restoration to a trihydrate through a moisturizing step. It is believed that, despite the water content in excess of about 8.92%, the bis-hydrochloride polymorph Form I in production batches remains as a trihydrate.

Analysis by DVS, as shown in FIG. 10, indicated that the water content of Formula (I) bis-hydrochloride trihydrate polymorph Form I changed from about 9% to about 14% from 20% to 90% relative humidity, and from about 14% to about 9% from 90% to 20% relative humidity. Without being bound to any particular theory, it is believed that water content in excess of about 8.92% (up to about 5% excess water, for a total water content of about 14%) resulted from water adsorption onto the trihydrate and not from the formation of a tetrahydrate by crystallization (a tetrahydrate would have a theoretical water content of about 11.6%) because the PXRD spectra of the trihydrate sample did not change even with up to about 5% additional water content.

The dissociation, pKa, was measured with a T3 (Sirius Analytical Instrument Ltd., UK). About 1 mg of Formula (I) bis-hydrochloride was transferred to a GLpKa beaker, dissolved with 43% to 53% MDM solution (ISA Water/MeOH/ACN/p-Dioxane=40/20/20/20, Sirius), adjusted to pH 1.8 with 0.5 N HCl, and titrated up to pH 12.2 with 0.5 N KOH. The pKa as an aqueous solution was calculated by extrapolation.

The dissociation constants (pKa) of Formula (I) bis-hydrochloride were determined to be 3.86 (pKa1), 4.73 (pKa2), and 10.30 (pKa3) as an aqueous solution. The dissociation constant data is indicated in Table 6.

TABLE 6

| | Dissociation constant (pKa) | | | |
|---|---|---|---|---|
| Test | 43% MDM solution | 43% MDM solution | 43% MDM solution | Aqueous |
| pKa | 3.85, 4.71, 10.37 | 3.88, 4.70, 10.36 | 3.84, 4.69, 10.38 | 3.86, 4.73, 10.3 |

The partition coefficient, Log P, was measured with a T3 (Sirius Analytical Instrument Ltd., UK). About 1 mg of Formula (I) bis-hydrochloride was added to a 15 mL GLpKa beaker, dissolved with octanol/150 mM KCl, adjusted to pH 1.8 with 0.5 N HCl, and titrated up to pH 12.2 with 0.5 N KOH. The partition coefficient of the octanol-water system was determined by correcting the difference between titration curves of the blank from the titration curve, by inserting the value of the dissociation constant measured previously.

The distribution coefficient (Log D) of Formula (I) bis-hydrochloride was determined to be 5.24 at pH 7.4 and the distributed ratio of Formula (I) bis-hydrochloride in an octanol phase to water phase was determined to be about 200,000 to 1. Formula (I) bis-hydrochloride is present in a neutral state at pH 11 or higher, Log P is 4.33, and the distributed ratio of Formula (I) bis-hydrochloride in the octanol phase to water phase is about 20,000 to 1. The distribution coefficient results of Formula (I) bis-hydrochloride are shown in Table 7.

TABLE 7

| LogD in octanol and water | |
|---|---|
| pH | LogD |
| 1 | 0.02 |
| 1.2 | 0.05 |
| 2 | 0.77 |
| 3 | 2.64 |
| 4 | 4.26 |
| 5 | 5.06 |
| 6 | 5.22 |
| 6.5 | 5.24 |
| 7 | 5.24 |
| 7.4 | 5.24 |
| 8 | 5.24 |
| 9 | 5.23 |
| 10 | 5.11 |
| 11 | 4.71 |
| 12 | 4.40 |
| — | — |

The solid form (crystalline or amorphous) was determined by PXRD recorded in a D8 ADVANCE made by BRUKER AXS in Germany, operating at 25° C. and at 40.0 KV and 100 mA, using Cu Kα (1.54056 Å) line and rotation.

As shown in the FIG. 1, Formula (I) bis-hydrochloride has a crystalline form. The diffraction pattern peak data is indicated in Table 8.

TABLE 8

| 2θ (±0.1°) | d value (Å) | I/I$_o$ (%) |
|---|---|---|
| 5.87 | 15.03 | 26.6 |
| 7.71 | 11.46 | 93.3 |
| 8.24 | 10.72 | 100 |
| 11.74 | 7.53 | 14.8 |

TABLE 8-continued

| 2θ (±0.1°) | d value (Å) | I/I$_o$ (%) |
|---|---|---|
| 15.74 | 5.63 | 7.4 |
| 16.59 | 5.34 | 19.9 |
| 26.75 | 3.33 | 13.1 |
| — | — | — |

Example 3: Preparation of a Crystalline Form (Form I) of a Dihydrochloride Salt of a Compound of Formula (I)

A crude dihydrochloride salt of a compound of Formula (I) (98.3% purity) was prepared from a Formula (I) free base prepared according to the method disclosed in WO 2013/100632 referenced herein or a similar method thereof, as referenced herein. 200 g of the compound of Formula (I) and 10 L of methanol were charged into a reactor of 20 L, followed by activated carbon (20 g). The reaction mixture was heated to 40 to 45° C. then stirred for 2 hrs. The reaction mixture was cooled to ~30° C., filtered through a Celite pad, and washed with 1 L of methanol. The filtrate was concentrated in vacuo. The residue was suspended in 4.0 L of an 80% aqueous ethanol solution and then a concentrated HCl solution was added. The mixture was stirred for 2 hours at reflux and then cooled to 30° C. to form a precipitate. The precipitate was filtered for 4 hours and then washed with 2.0 L of ethanol. The filtered solids were dried in a vacuum oven at 50° C. for 24 hours. The dried solids were ground and stored in a humidity chamber (40° C., 75% RH) overnight. Yield: 198 g (99.0%); Moisture: 12%; and HCl content by ion chromatography IC: 13.0% (theoretical value 13.0% as 2 HCl).

Analysis of Characteristics

Figure 12:
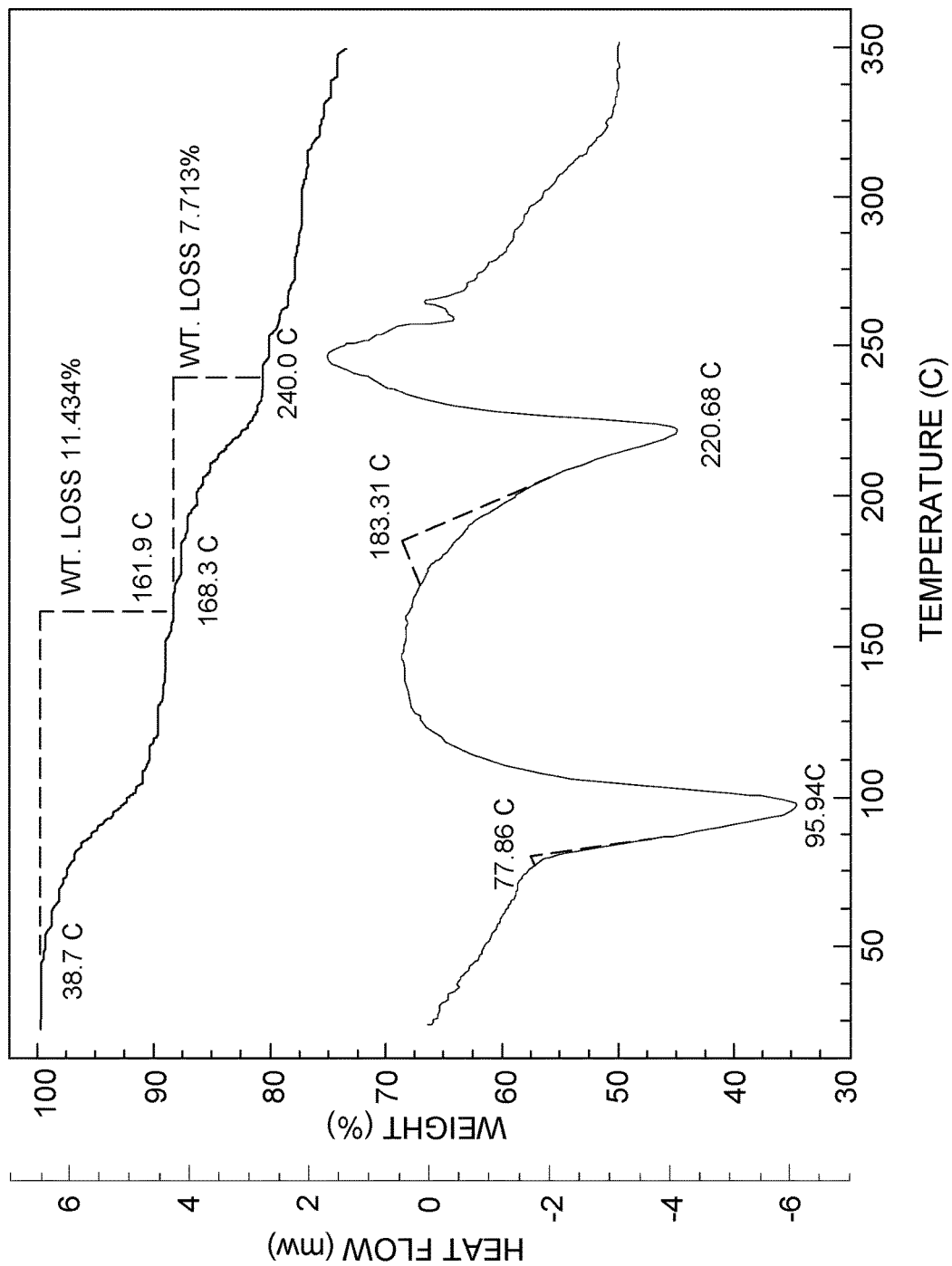
FIG. 12 shows a DSC diagram for Formula (I) bis-hydrochloride salt crystalline polymorph Form I.
Figure 13:
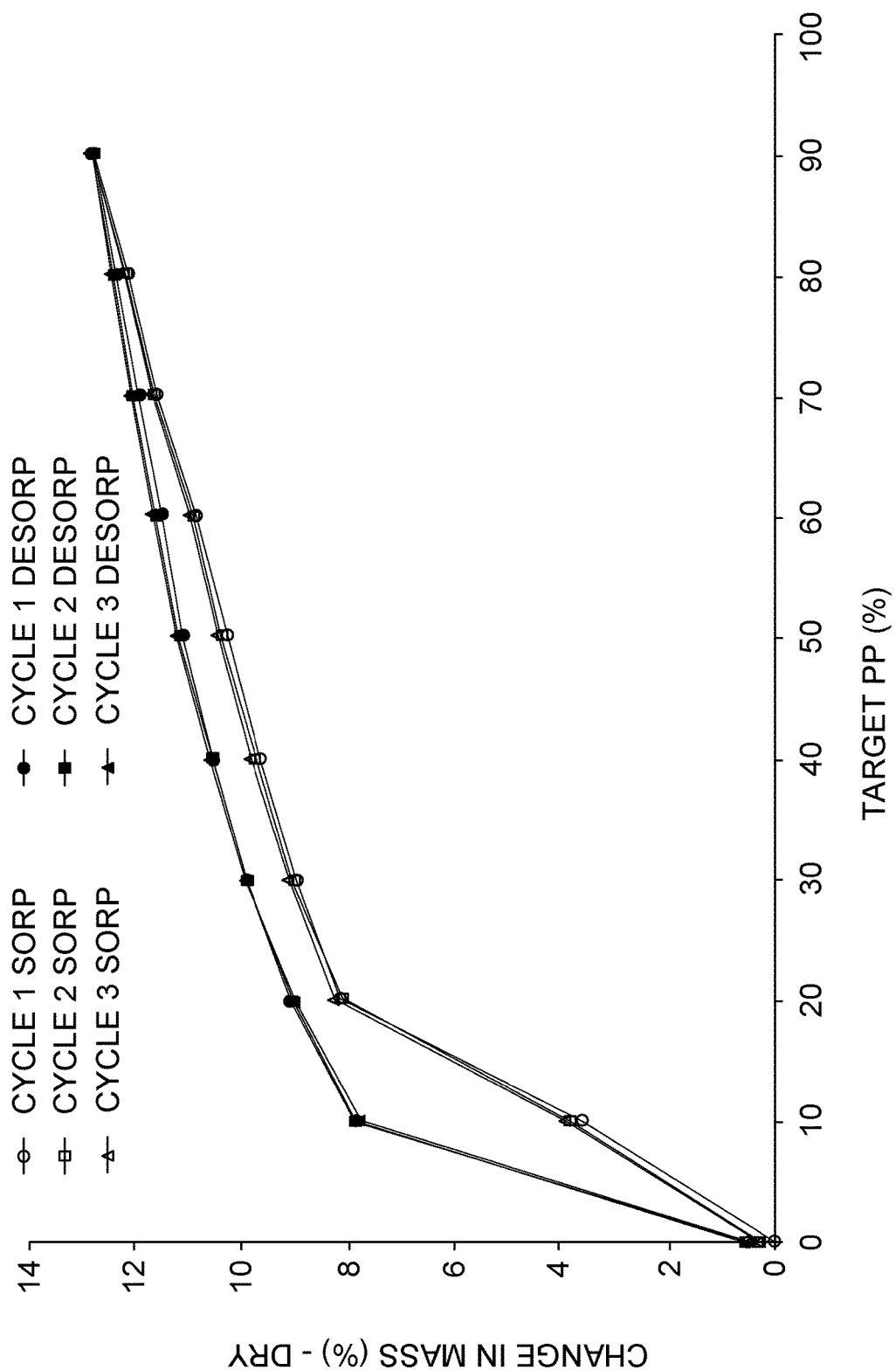
FIG. 13 shows a DVS diagram for Formula (I) bis-hydrochloride salt crystalline polymorph Form I.

The results of PXRD analysis of the crystalline form prepared in Example 3 are shown in FIG. 35, the DSC results are shown in FIG. 12, and the DVS results are shown in FIG. 13.

Form I was characterized by a melting point with an onset temperature (DSC) of about 221° C. (FIG. 12).

The peaks having a relative intensity (I/Io) of 3% or higher in the PXRD spectrum of the above crystalline form are shown in Table 9 below. For peaks having I/Io ratios equal to or higher than 10%, the diffraction angles were 5.89°, 7.77°, 8.31°, 11.80°, 16.68°, 23.22°, 23.69°, 26.89°, 27.51°, 28.29° and 29.53° (2θ±0.2°).

TABLE 9

| 2θ (±0.2) | d Value (Å) | Intensity | I/I$_o$ (%) |
|---|---|---|---|
| 5.89 | 15.00 | 375 | 33.1 |
| 7.77 | 11.37 | 1029 | 90.9 |
| 8.31 | 10.63 | 1132 | 100 |
| 9.76 | 9.05 | 56 | 4.9 |
| 11.80 | 7.50 | 171 | 15.1 |
| 12.92 | 6.85 | 50 | 4.4 |
| 14.13 | 6.26 | 42 | 3.7 |
| 14.50 | 6.11 | 58 | 5.1 |
| 15.86 | 5.58 | 105 | 9.3 |
| 16.68 | 5.31 | 233 | 20.6 |
| 17.02 | 5.21 | 76 | 6.7 |
| 17.71 | 5.00 | 43 | 3.8 |
| 18.73 | 4.73 | 49 | 4.3 |
| 19.60 | 4.53 | 46 | 4.1 |
| 21.82 | 4.07 | 74 | 6.5 |
| 22.68 | 3.92 | 61 | 5.4 |
| 23.22 | 3.83 | 135 | 11.9 |
| 23.69 | 3.75 | 176 | 15.5 |

TABLE 9-continued

| 2θ (±0.2) | d Value (Å) | Intensity | I/I$_o$ (%) |
|---|---|---|---|
| 26.06 | 3.42 | 79 | 7 |
| 26.89 | 3.31 | 238 | 21 |
| 27.51 | 3.24 | 170 | 15 |
| 28.29 | 3.15 | 127 | 11.2 |
| 29.53 | 3.02 | 134 | 11.8 |
| 30.81 | 2.90 | 72 | 6.4 |
| 32.09 | 2.79 | 88 | 7.8 |
| 33.63 | 2.66 | 86 | 7.6 |
| 39.73 | 2.27 | 62 | 5.5 |
| — | — | — | — |

Example 4: Preparation of a Crystalline Form (Form II) of a Dihydrochloride of a Compound of Formula (I)

25 g of the crystalline form (Form I) of the dihydrochloride salt of the compound of Formula (I) prepared in Example 3 was charged into a reactor, then 500 mL of methanol and 750 mL of THF were added. The resulting suspension was heated to reflux for 18 hours. The reaction mixture was cooled to 20 to 25° C. Generated precipitates were filtered and then washed with 125 mL of THF. Filtered solids were dried in a vacuum oven at 50° C. for 21 hours. The resulting solids were ground and stored in a humidity chamber (25° C., 60% RH) for 21 hours. Yield: 17.8 g (71.0%); Moisture: 13.9%; and HCl content by IC: 13.2% (theoretical value 13.0% as 2 HCl).

Analysis of Characteristics

Figure 15:
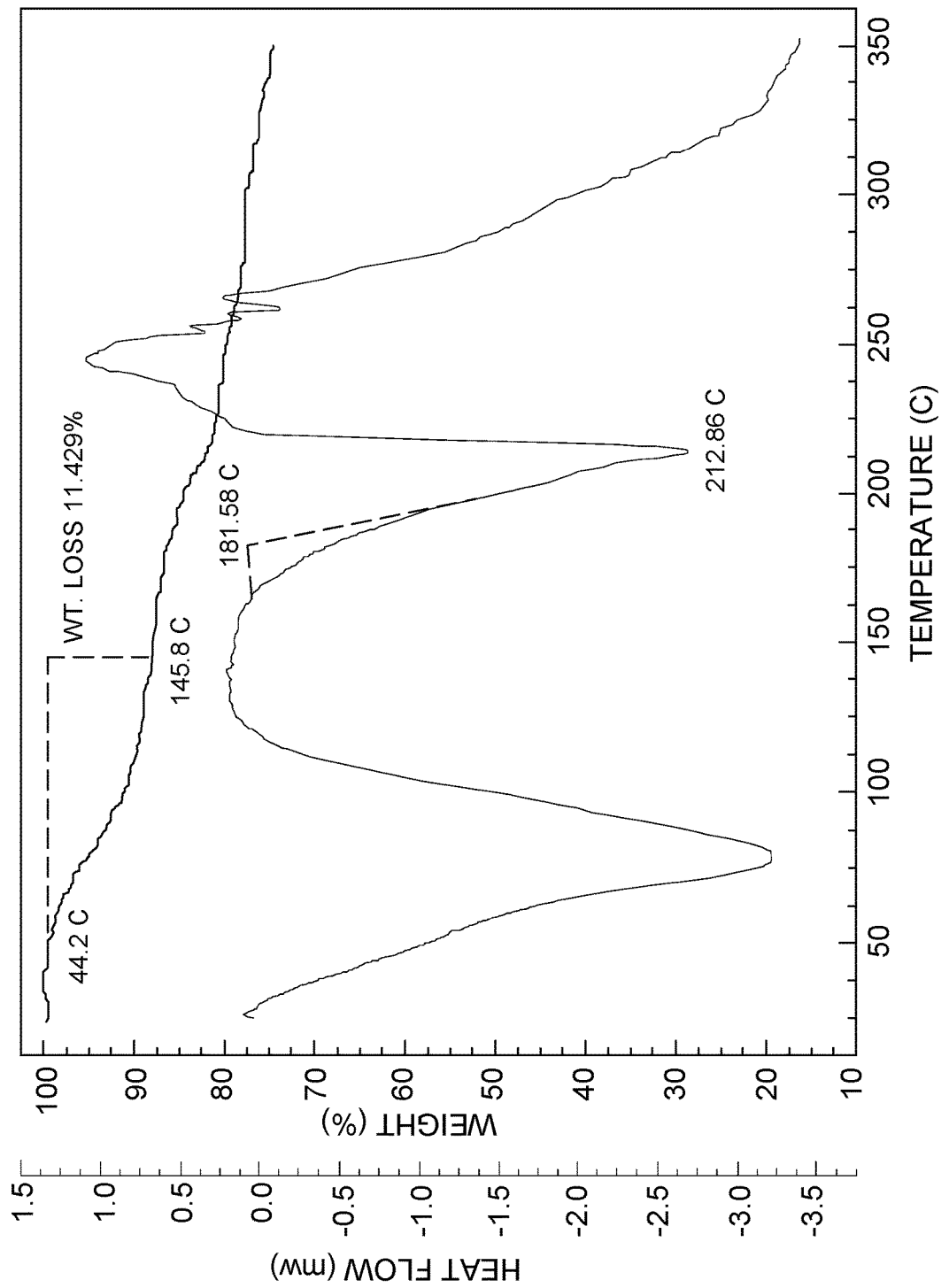
FIG. 15 shows a DSC diagram for Formula (I) bis-hydrochloride salt crystalline polymorph Form II.
Figure 16:
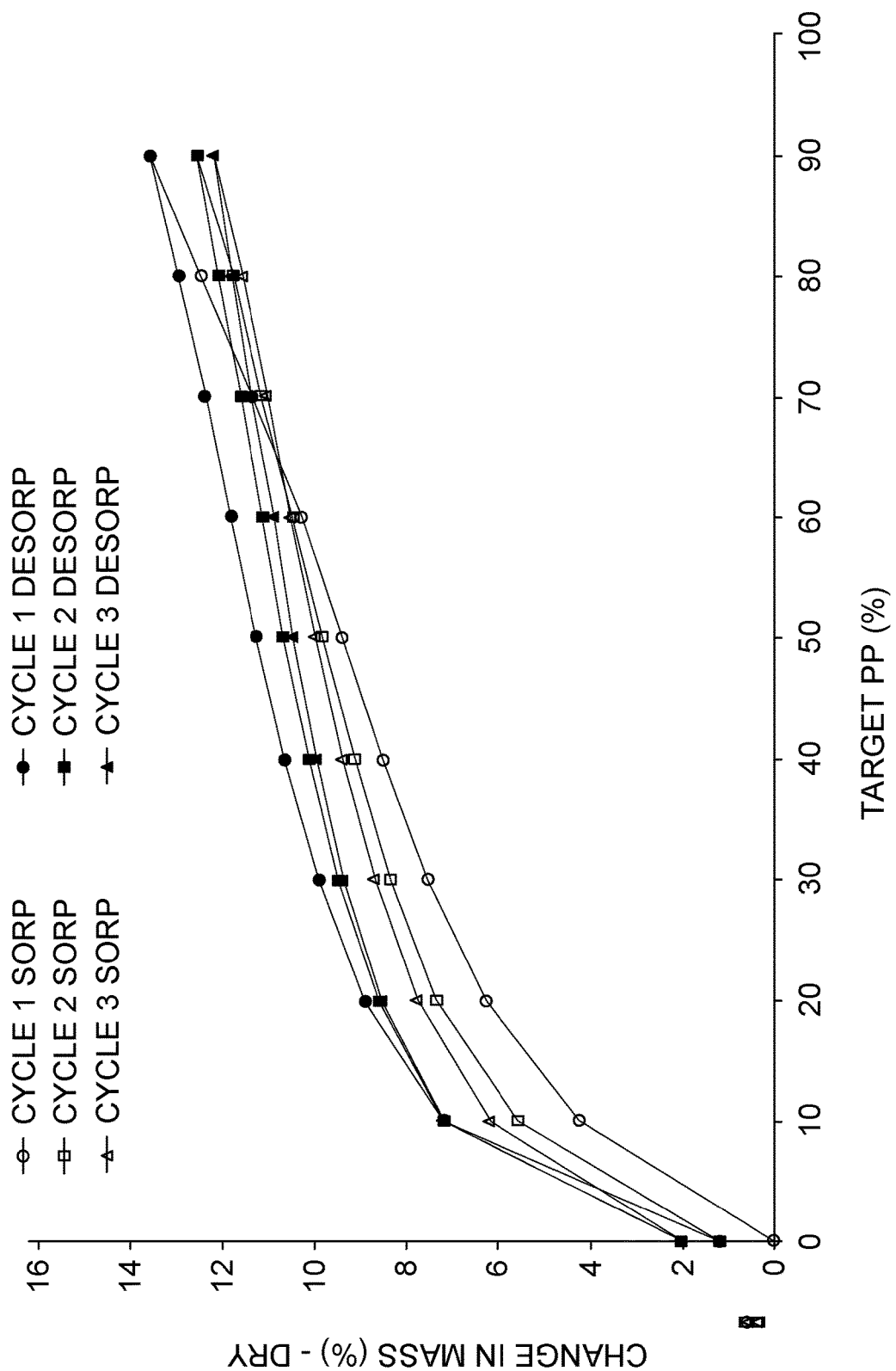
FIG. 16 shows a DVS diagram for Formula (I) bis-hydrochloride salt crystalline polymorph Form II.

The results of PXRD analysis of the crystalline form prepared in Example 4 are shown in FIG. 14, the DSC results are shown in FIG. 15, and the DVS results are shown in FIG. 16.

The peaks having a relative intensity (I/Io) of 3% or higher in the PXRD spectrum of the above crystalline form are shown in Table 10 below. For peaks having a I/Io ratio equal to or higher than 10%, the diffraction angles were 6.19°, 6.55°, 7.00°, 9.01°, 9.85°, 11.64°, 12.86°, 14.05° and 25.31° (2θ±0.20).

Form II was characterized by a melting point with an onset temperature (DSC) of about 213° C. (FIG. 15).

TABLE 10

| 2θ (±0.2) | d Value (Å) | Intensity | I/I$_o$ (%) |
|---|---|---|---|
| 6.19 | 14.26 | 387 | 35.7 |
| 6.55 | 13.49 | 247 | 22.8 |
| 7.00 | 12.62 | 1083 | 100 |
| 9.01 | 9.81 | 140 | 12.9 |
| 9.85 | 8.97 | 139 | 12.8 |
| 11.64 | 7.60 | 125 | 11.5 |
| 12.86 | 6.88 | 208 | 19.2 |
| 14.05 | 6.30 | 131 | 12.1 |
| 25.31 | 3.52 | 123 | 11.4 |
| — | — | — | — |

Example 5: Preparation of a Crystalline Form (Form III) of a Dihydrochloride of a Compound of Formula (I)

25 g of the crystalline form (Form I) of the dihydrochloride of the compound of Formula (I) prepared in Example 3 was charged into a reactor, then 500 mL of methanol and 750 mL of IPA were added. The resulting suspension was heated to reflux for 18 hours. The reaction mixture was cooled to 20 to 25° C. Generated precipitates were filtered and then washed with 125 mL of IPA. Filtered solids were dried in a vacuum oven at 50° C. for 21 hours. The resulting solids were ground and stored in a humidity chamber (25° C., 60% RH) for 21 hours. Yield: 18.4 g (74.0%); Moisture: 0.4%; ID: and HCl content by 13.2% (theoretical value 13.0% as 2 HCl; and residual solvent: 2% of methanol.

Analysis of Characteristics

Figure 18:
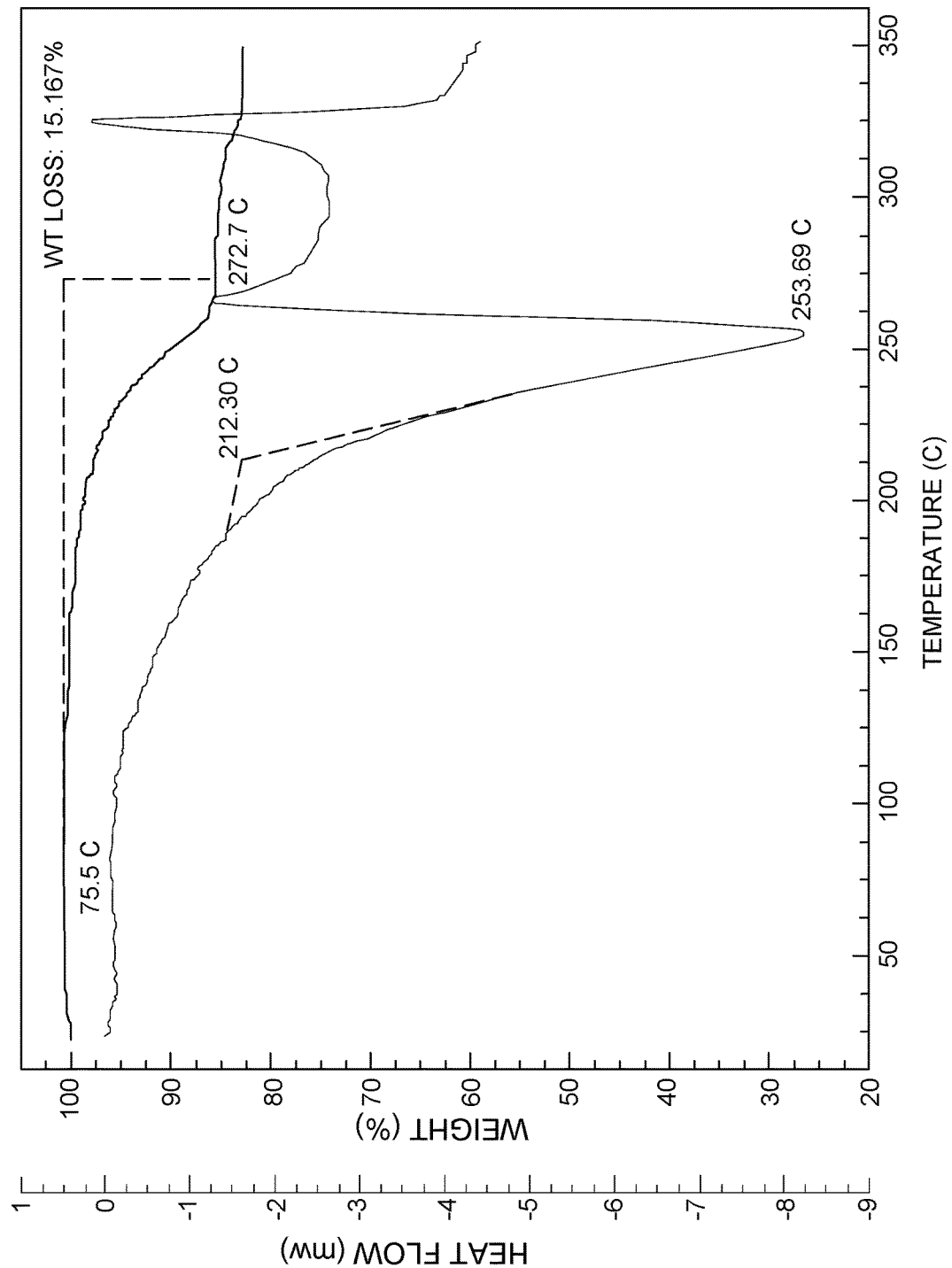
FIG. 18 shows a DSC diagram for Formula (I) bis-hydrochloride salt crystalline polymorph Form III.
Figure 19:
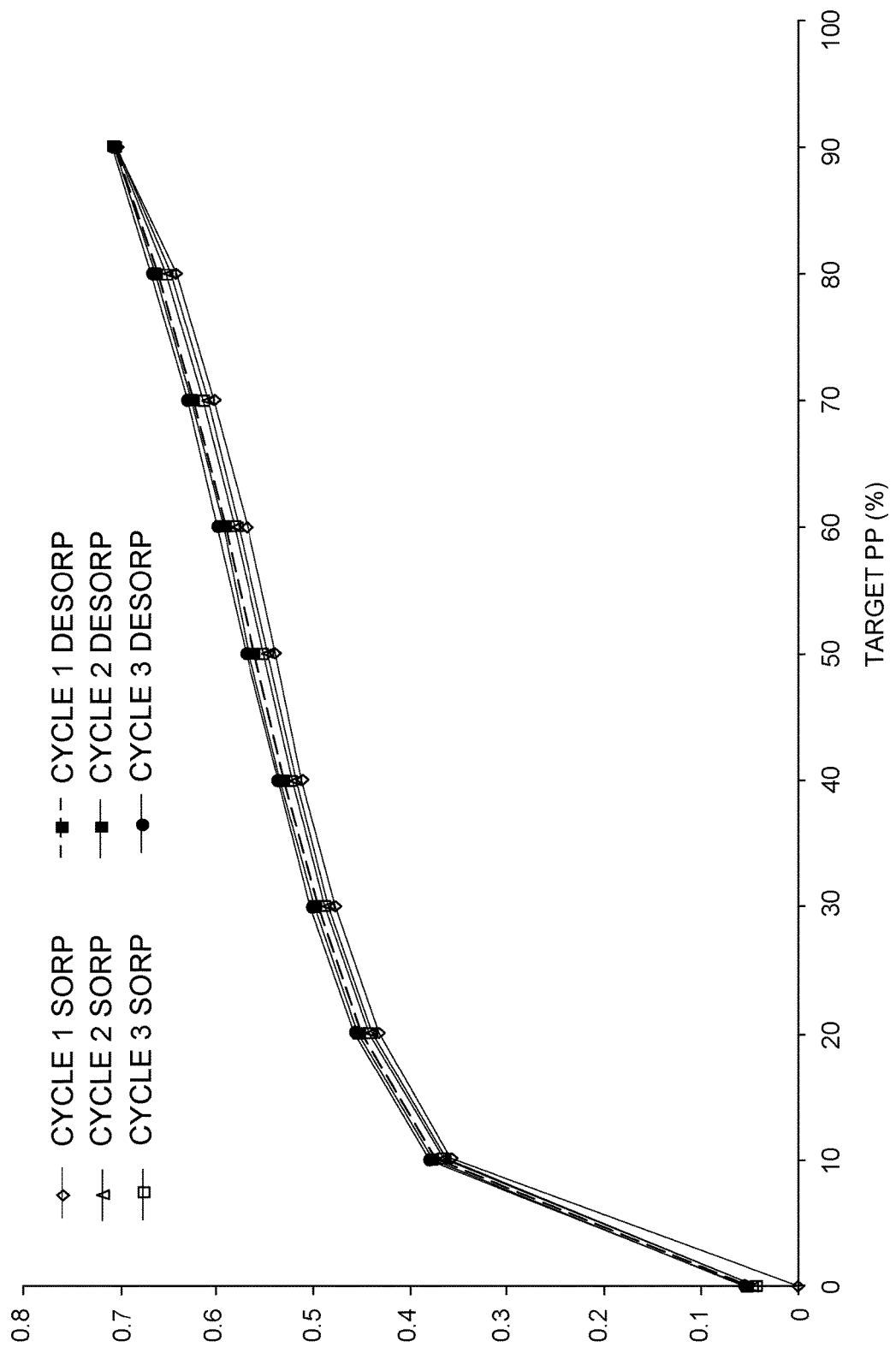
FIG. 19 shows a DVS diagram for Formula (I) bis-hydrochloride salt crystalline polymorph Form III.

The results of PXRD analysis of the crystalline form prepared in Example 5 are shown in FIG. 17, the DSC results are shown in FIG. 18, and the DVS results are shown in FIG. 19.

Form II was characterized by a melting point with an onset temperature (DSC) of about 254° C. (FIG. 18).

The peaks having a relative intensity (I/Io) of 3% or higher in the PXRD spectrum of the above crystalline form are shown in Table 11 below. For peaks having a I/Io ratio equal to or higher than 10%, the diffraction angles were 6.01°, 9.00°, 11.47°, 12.05°, 14.48°, 16.33°, 16.83°, 18.13°, 19.01°, 19.26°, 22.63°, 23.10°, 24.51°, 25.31°, 25.94°, 26.51°, 27.10°, 28.12°, 30.47° and 31.25° (2θ±0.2°).

TABLE 11

| 2θ (±0.2) | d Value (Å) | Intensity | I/I$_o$ (%) |
|---|---|---|---|
| 6.01 | 14.69 | 373 | 28.9 |
| 8.36 | 10.57 | 99 | 7.7 |
| 9.0 | 9.82 | 1290 | 100 |
| 11.47 | 7.71 | 431 | 33.4 |
| 12.05 | 7.34 | 214 | 16.6 |
| 12.86 | 6.88 | 54 | 4.2 |
| 13.94 | 6.35 | 41 | 3.2 |
| 14.48 | 6.11 | 236 | 18.3 |
| 14.82 | 5.97 | 126 | 9.8 |
| 15.58 | 5.68 | 83 | 6.4 |
| 16.33 | 5.42 | 416 | 32.2 |
| 16.83 | 5.26 | 192 | 14.9 |
| 18.13 | 4.89 | 342 | 26.5 |
| 19.01 | 4.66 | 144 | 11.2 |
| 19.26 | 4.60 | 131 | 10.2 |
| 20.44 | 4.34 | 40 | 3.1 |
| 21.50 | 4.13 | 114 | 8.8 |
| 21.86 | 4.06 | 75 | 5.8 |
| 22.20 | 4.00 | 122 | 9.5 |
| 22.63 | 3.93 | 272 | 21.1 |
| 23.10 | 3.85 | 382 | 29.6 |
| 23.67 | 3.76 | 53 | 4.1 |
| 24.51 | 3.63 | 202 | 15.7 |
| 25.31 | 3.52 | 189 | 14.7 |
| 25.94 | 3.44 | 271 | 21 |
| 26.51 | 3.36 | 139 | 10.8 |
| 27.10 | 3.29 | 267 | 20.7 |
| 27.53 | 3.24 | 104 | 8.1 |
| 28.12 | 3.17 | 132 | 10.2 |
| 28.67 | 3.11 | 96 | 7.4 |
| 29.11 | 3.07 | 103 | 8 |
| 29.65 | 3.01 | 52 | 4 |
| 30.47 | 2.93 | 281 | 21.8 |
| 30.76 | 2.90 | 96 | 7.4 |
| 31.25 | 2.86 | 181 | 14 |
| 31.81 | 2.81 | 63 | 4.9 |
| 32.29 | 2.77 | 74 | 5.7 |
| 32.80 | 2.73 | 66 | 5.1 |
| 33.09 | 2.71 | 46 | 3.6 |
| 34.51 | 2.60 | 62 | 4.8 |
| 34.93 | 2.57 | 114 | 8.8 |
| 35.58 | 2.52 | 83 | 6.4 |
| 36.78 | 2.44 | 84 | 6.5 |
| 37.73 | 2.38 | 52 | 4 |
| 38.66 | 2.33 | 54 | 4.2 |
| 39.03 | 2.31 | 81 | 6.3 |
| 39.78 | 2.26 | 107 | 8.3 |
| — | — | — | — |

Example 6: Preparation of a Crystalline Form (Form IV) of a Dihydrochloride of a Compound of Formula (I) Å

5 g of the crystalline form (Form I) of the dihydrochloride of the compound of Formula (I) prepared in Example 3 was charged into a reactor, then 50 mL of DMF was added. The mixture was heated to reflux for 1 hour. The reaction mixture was cooled to 20 to 25° C. The seeding compound was added at 20 to 25° C. The resulting solids were stirred for 24 hours at 20 to 25° C., filtered and then washed with 50 mL of n-Heptane. The filtered solids were dried in a vacuum oven at 50° C. for 21 hours. Yield: 0.72 g (14.4%); Residual Solvent: 2.1% DMF.

Analysis of Characteristics

The result of PXRD analysis of the crystalline form prepared in Example 6 is shown in FIG. 20.

The peaks having a relative intensity (I/Io) of 3% or higher in the PXRD spectrum of the above crystalline form are shown in Table 12 below. For peaks having a I/Io ratio equal to or higher than 10%, the diffraction angles were 5.56°, 6.64°, 7.15°, 9.07°, 11.22°, 11.76°, 12.12°, 13.30°, 14.28°, 15.57°, 17.26°, 18.2°, 22.3°, 22.9°, 23.7°, 24.8°, 25.1°, 25.9°, 28.2°, 29.9°, 31.3° and 34.2° (2θ±0.2°).

TABLE 12

| 2θ (±0.2) | d Value (Å) | Intensity | I/I$_o$ (%) |
|---|---|---|---|
| 5.56 | 15.87 | 111 | 14.8 |
| 6.64 | 13.31 | 749 | 100 |
| 7.15 | 12.35 | 147 | 19.6 |
| 9.07 | 9.74 | 216 | 28.8 |
| 11.22 | 7.88 | 411 | 54.9 |
| 11.76 | 7.52 | 287 | 38.3 |
| 12.12 | 7.30 | 94 | 12.6 |
| 13.30 | 6.65 | 254 | 33.9 |
| 14.28 | 6.20 | 78 | 10.4 |
| 15.57 | 5.69 | 92 | 12.3 |
| 16.36 | 5.41 | 59 | 7.9 |
| 17.26 | 5.13 | 102 | 13.6 |
| 18.25 | 4.86 | 82 | 10.9 |
| 22.28 | 3.99 | 94 | 12.6 |
| 22.95 | 3.87 | 131 | 17.5 |
| 23.69 | 3.75 | 119 | 15.9 |
| 24.77 | 3.59 | 154 | 20.6 |
| 25.06 | 3.55 | 136 | 18.2 |
| 25.88 | 3.44 | 104 | 13.9 |
| 28.20 | 3.16 | 135 | 18 |
| 29.92 | 2.98 | 112 | 15 |
| 31.33 | 2.85 | 85 | 11.3 |
| 34.17 | 2.62 | 76 | 10.1 |
| — | — | — | — |

Example 7: Preparation of a Crystalline Form (Form V) of a Dihydrochloride of a Compound of Formula (I)

20 g of a free base of the compound of Formula (I) (99.7% purity, <0.1% H2O) was charged into a reactor, then 300 mL of DMF was added. The mixture was heated to 140° C. The reaction mixture was cooled to 80° C., and then 8 mL of conc. HCl was added. The resulting solid was stirred for 2.5 hrs at 20 to 25° C., filtered and then washed with 50 mL of n-Heptane. The filtered solids were dried in a vacuum oven at 50° C. for 21 hrs. Yield: 26 g (110%); residual solvent: 12.4% of DMF.

Analysis of Characteristics

The results of PXRD analysis of the crystalline form prepared in Example 7 are shown in FIG. 21.

The peaks having a relative intensity (I/Io) of 3% or higher in the PXRD spectrum of the above crystalline form are shown in Table 13 below. For peaks having a I/Io ratio equal to or higher than 10%, the diffraction angles were 5.44°, 6.58°, 7.48°, 9.22°, 10.84°, 11.47°, 12.45°, 13.17°, 16.61°, 17.18°, 17.92°, 18.52°, 22.21°, 23.07°, 23.84°, 24.70°, 25.37°, 26.08°, 27.33°, 29.12°, 31.02°, 31.43°, 34.65° and 37.46° (2θ±0.2°).

TABLE 13

| 2θ (±0.2) | d Value (Å) | Intensity | I/I$_o$ (%) |
|---|---|---|---|
| 5.44 | 16.23 | 84 | 14.1 |
| 6.58 | 13.43 | 597 | 100 |
| 7.48 | 11.82 | 284 | 47.6 |
| 8.29 | 10.65 | 57 | 9.5 |
| 9.22 | 9.58 | 190 | 31.8 |
| 10.84 | 8.15 | 236 | 39.5 |
| 11.47 | 7.71 | 333 | 55.8 |
| 12.45 | 7.10 | 85 | 14.2 |
| 13.17 | 6.72 | 265 | 44.4 |
| 14.95 | 5.92 | 47 | 7.9 |
| 16.61 | 5.33 | 106 | 17.8 |
| 17.18 | 5.16 | 141 | 23.6 |
| 17.92 | 4.95 | 70 | 11.7 |
| 18.52 | 4.79 | 124 | 20.8 |
| 22.21 | 4.00 | 99 | 16.6 |
| 23.07 | 3.85 | 254 | 42.5 |
| 23.84 | 3.73 | 140 | 23.5 |
| 24.70 | 3.60 | 225 | 37.7 |
| 25.37 | 3.51 | 140 | 23.5 |
| 26.08 | 3.41 | 118 | 19.8 |
| 27.33 | 3.26 | 175 | 29.3 |
| 29.12 | 3.06 | 111 | 18.6 |
| 31.02 | 2.88 | 69 | 11.6 |
| 31.43 | 2.84 | 80 | 13.4 |
| 32.22 | 2.78 | 69 | 9.9 |
| 34.65 | 2.59 | 66 | 11.1 |
| 37.46 | 2.40 | 65 | 10.9 |
| — | — | — | — |

Example 8: Preparation of a Crystalline Form (Form VI) of a Dihydrochloride of a Compound of Formula (I)

20 g of the crystalline form (Form I) of the dihydrochloride of the compound of Formula (I) prepared in Example 1 was dried in a vacuum oven at 50° C. for 24 hours. Yield: 17.4 g (87.0%); moisture: 0.7%.

Analysis of Characteristics

Figure 23:
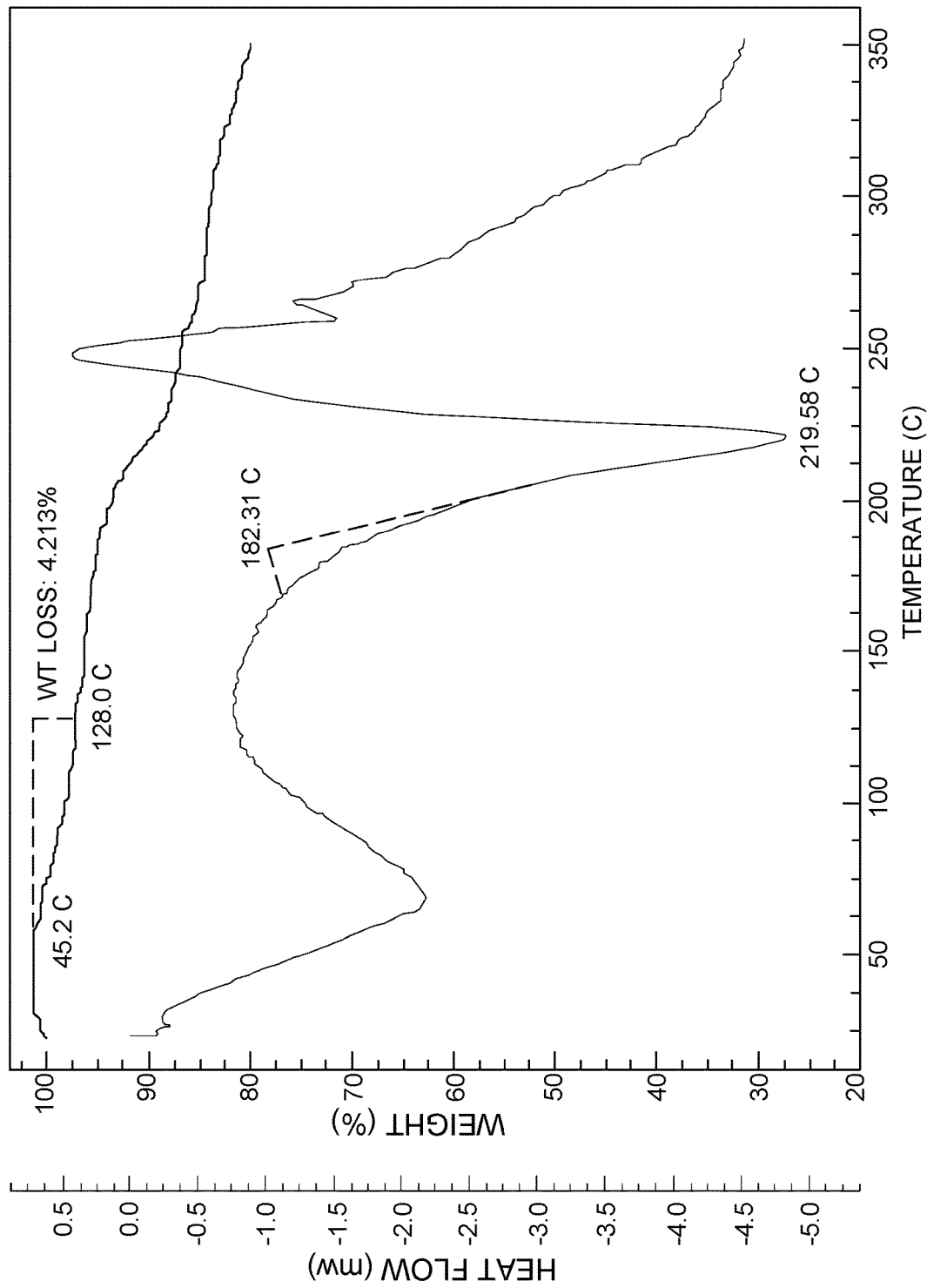
FIG. 23 shows a DSC diagram for Formula (I) bis-hydrochloride salt crystalline polymorph Form VI.

The results of PXRD analysis of the crystalline form prepared in Example 8 are shown in FIG. 22 and the DSC results are shown in FIG. 23.

Form VI was characterized by a melting point with an onset temperature (DSC) of about 220° C. (FIG. 23).

The peaks having a relative intensity (I/Io) of 3% or higher in the PXRD spectrum of the above crystalline form are shown in Table 14 below. For peaks having a I/Io ratio equal to or higher than 10%, the diffraction angles were 8.5° and 8.9° (2θ±0.2°).

TABLE 14

| 2θ (±0.2) | d Value (Å) | Intensity | I/I$_o$ (%) |
|---|---|---|---|
| 5.86 | 15.06 | 92 | 9.8 |
| 8.47 | 10.43 | 936 | 100 |
| 8.90 | 9.93 | 397 | 42.4 |
| 12.10 | 7.31 | 83 | 8.9 |
| 14.00 | 6.34 | 77 | 8.2 |
| 16.30 | 5.43 | 59 | 6.3 |
| 16.71 | 5.30 | 56 | 6 |
| 23.49 | 3.78 | 78 | 8.3 |

Figure 24:
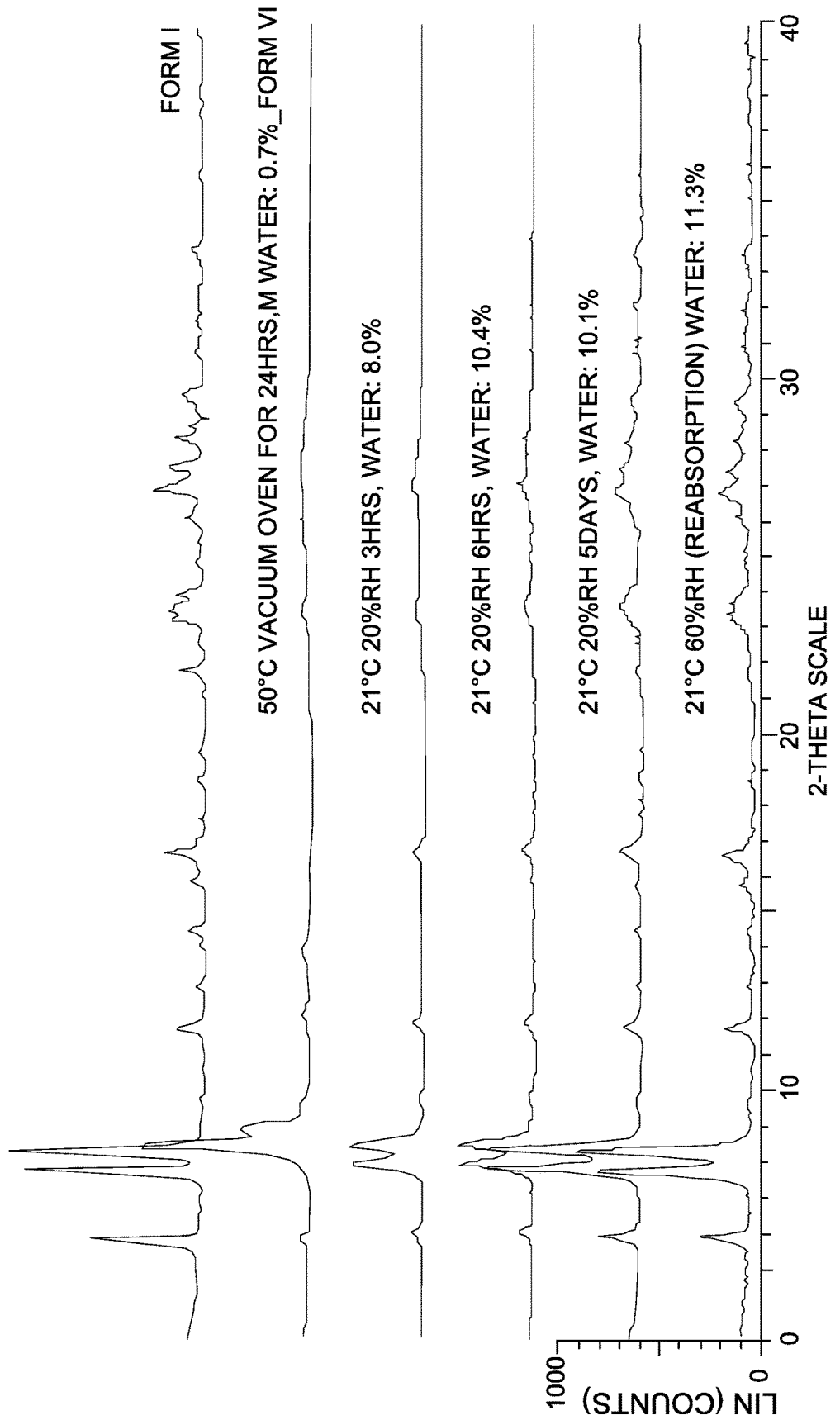
FIG. 24 shows a PXRD pattern for Formula (I) bis-hydrochloride salt crystalline polymorph Forms I and VI.

Example 9: Preparation of Formula (I) Bis-Hydrochloride Polymorph Form I from Form VI Crystalline Form VI was converted to Form I by two methods. In a first method, Form VI was exposed to a relative humidity of 60% at 25° C. In a second method, Form VI was exposed to a relative humidity of 20% at 21° C. The PXRD results for the conversion of Form VI to Form I are indicated in FIG. 24. Depicted are: (i) Form I; (ii) Form VI prepared by drying Form I at 50° C. in a vacuum oven for 24 hours; (iii) Form VI after exposure at 21° C. and 20% RH for 3 hours resulting in a water content of 8.0%; (iv) Form VI after exposure at 21° C. and 20% RH for 6 hours resulting in a water content of 10.4%; (v) Form VI after exposure at 21° C. and 20% RH for 5 days resulting in a water content of 10.1%; and (vi) Form VI after exposure at 25° C. and 60% RH resulting in a water content of 11.3%.

Example 10: Summary of Formula (I) Bis-Hydrochloride Polymorph Interconversion

FIG. 25 summarizes the interconversion of Formula (I) bis-hydrochloride polymorph Form I to and from Forms II to VI, and to amorphous Formula (I) bis-hydrochloride as described in the present examples.

Example 11: Preparation of a Crystalline Form of a Bi-Hydrogensulfate Salt of a Compound of Formula (I)

500 mg of a free base of the compound of Formula (I) was charged into a reactor, then 10 mL of 80% methanol (MeOH) was added. To the suspension mixture, sulfuric acid (2.2 eq) was added. The resulting solid was stirred for 12 hrs at 20 to 25° C. The resulting solid was filtered and then washed with 10 mL of 80% MeOH. The filtered solids were dried in a vacuum oven at 50° C. for 18 hrs. 648 mg of the title compound was obtained (yield: 92%).

Analysis of Characteristics

The results of PXRD analysis of the crystalline form prepared in Example 11 are shown in FIG. 4.

The peaks having a relative intensity (I/Io) of 3% or higher in the PXRD spectrum of the above crystalline form are shown in Table 15 below. For peaks having a I/Io ratio equal to or higher than 10%, the diffraction angles were 5.7°, 7.4°, 7.9°, 9.4°, 11.5°, 13.7°, 15.0°, 15.9°, 16.9°, 17.7°, 18.5°, 18.9°, 20.3°, 20.9°, 21.6°, 22.4°, 22.9°, 23.3°, 24.0°, 24.4°, 24.6°, 25.3°, 25.9°, 26.5°, 27.3°, 28.7° and 33.7° (2θ±0.2°).

TABLE 15

| 2θ (±0.2) | d Value (Å) | I/I$_o$ (%) |
|---|---|---|
| 5.7 | 15.4 | 23.1 |
| 7.4 | 11.9 | 35.6 |
| 7.9 | 11.1 | 100 |
| 9.4 | 9.4 | 11.8 |
| 11.5 | 7.7 | 35.3 |
| 12.6 | 7.0 | 8.9 |
| 13.7 | 6.5 | 23.7 |
| 15.0 | 5.9 | 58.9 |
| 15.9 | 5.6 | 93.1 |
| 16.9 | 5.2 | 19 |
| 17.7 | 5.0 | 16.8 |
| 18.5 | 4.8 | 41.3 |
| 18.9 | 4.7 | 32.4 |
| 20.3 | 4.4 | 22.8 |
| 20.9 | 4.3 | 24.9 |
| 21.6 | 4.1 | 23.2 |
| 22.4 | 4.0 | 41.3 |
| 22.9 | 3.9 | 33.6 |
| 23.3 | 3.8 | 26.3 |

TABLE 15-continued

| 2θ (±0.2) | d Value (Å) | I/I$_o$ (%) |
|---|---|---|
| 24.0 | 3.7 | 41.1 |
| 24.4 | 3.6 | 34.7 |
| 24.6 | 3.6 | 35 |
| 25.3 | 3.5 | 34.4 |
| 25.9 | 3.4 | 71.7 |
| 26.5 | 3.4 | 27.7 |
| 27.3 | 3.3 | 21.7 |
| 28.7 | 3.1 | 16.7 |
| 32.6 | 2.7 | 9.5 |
| 33.7 | 2.7 | 10.1 |
| — | — | — |

Example 12: Preparation of a Crystalline Form (Form A) of a Di(p-Toluenesulfonate) of a Compound of Formula (I)

Step 1: Preparation of an Amorphous Form of the Di(p-Toluenesulfonate) of a Compound of Formula (I)

0.5 g of a free base of the compound of Formula (I) was charged into a reactor, then 10 mL of acetone (AC) was added. To the suspension mixture, p-toluenesulfonic acid monohydrate (2.2 eq) was added. The resulting solid was stirred for 24 hrs at 20 to 25° C. and then filtered and then washed with 2.5 mL of AC. Filtered solids were dried in an oven at 50° C. for 18 hrs. Yield: 0.3 g (35%)

Step 2: Preparation of the Crystalline Form (Form A) of a Di(p-Toluenesulfonate) of a Compound of Formula 2

15 g of the amorphous form of the compound of Formula (I) was charged into a reactor, then 300 mL of ethyl acetate (EA) was added. The suspension mixture was stirred for 24 hrs at reflux, filtered, and then washed with 75 mL of EA. Filtered solids were dried in a vacuum oven at 50° C. for 18 hrs. Yield: 11 g (73%)

Analysis of Characteristics

The results of PXRD analysis of the crystalline form prepared in Example 12 are shown in FIG. 26.

The peaks having a relative intensity (I/Io) of 3% or higher in the PXRD spectrum of the above crystalline form are shown in Table 16 below. For peaks having a I/Io ratio equal to or higher than 10%, the diffraction angles were 3.2°, 4.5°, 7.7°, 8.4°, 9.0°, 11.7°, 13.2°, 13.6°, 14.1°, 15.3°, 15.8°, 16.7°, 17.4°, 18.8°, 19.9°, 21.7°, 21.9°, 22.3°, 23.0°, 23.5°, 24.6°, 24.7°, 25.6°, 27.4° and 29.0° (2θ±0.2°).

TABLE 16

| 2θ (±0.2) | d Value (Å) | I/I$_o$ (%) |
|---|---|---|
| 3.2 | 27.5 | 20 |
| 4.5 | 19.5 | 100 |
| 7.7 | 11.5 | 27.3 |
| 8.4 | 10.5 | 23.1 |
| 9.0 | 9.8 | 13.4 |
| 11.7 | 7.6 | 21.5 |
| 13.2 | 6.7 | 21.7 |
| 13.6 | 6.5 | 26.2 |
| 14.1 | 6.3 | 39.9 |
| 15.3 | 5.8 | 63 |
| 15.8 | 5.6 | 26.6 |
| 16.7 | 5.3 | 19.2 |
| 17.4 | 5.1 | 58.5 |
| 18.8 | 4.7 | 26.2 |
| 19.9 | 4.5 | 16.1 |
| 21.7 | 4.1 | 54.8 |
| 21.9 | 4.0 | 42.1 |
| 22.3 | 4.0 | 31 |
| 23.0 | 3.9 | 41.9 |
| 23.5 | 3.8 | 24.4 |
| 24.6 | 3.6 | 40.5 |
| 24.7 | 3.6 | 41.9 |
| 25.6 | 3.5 | 39 |
| 27.4 | 3.3 | 30.2 |
| 29.0 | 3.1 | 26.2 |
| — | — | — |

Example 13: Preparation of a Crystalline Form (Form B) of a Di(p-Toluenesulfonate) of a Compound of Formula (I)

3 g of a free base of the compound of Formula (I) was charged into a reactor, then 50 mL of ACN was added. To the suspension mixture, p-toluenesulfonic acid monohydrate (2.2 eq) in ACN (10 mL) was added. The resulting solid was stirred for 24 hrs at 20 to 25° C., filtered, and then washed with 50 mL of ACN. Filtered solids were dried in an oven at 50° C. for 18 hrs. Yield: 4.92 g (95%).

Analysis of Characteristics

The results of PXRD analysis of the crystalline form prepared in Example 13 are shown in FIG. 27.

The peaks having a relative intensity (I/Io) of 3% or higher in the PXRD spectrum of the above crystalline form are shown in Table 17 below. For peaks having a I/Io ratio equal to or higher than 10%, the diffraction angles were 5.7°, 7.8°, 9.3°, 11.4°, 11.6°, 12.5°, 12.9°, 13.2°, 14.0°, 15.0°, 15.8°, 16.0°, 17.0°, 17.5°, 18.8°, 19.2°, 19.8°, 20.5°, 21.0°, 21.4°, 21.9°, 22.4°, 22.8°, 23.4°, 24.2°, 24.9°, 26.2°, 27.2°, 28.1°, 29.1° and 31.6° (2θ±0.2°).

TABLE 17

| 2θ (±0.2) | d Value (Å) | I/I$_o$ (%) |
|---|---|---|
| 5.7 | 15.6 | 100 |
| 6.4 | 13.8 | 9.9 |
| 7.8 | 11.3 | 25.8 |
| 9.3 | 9.5 | 11.6 |
| 11.4 | 7.8 | 16.2 |
| 11.6 | 7.6 | 61.3 |
| 12.5 | 7.1 | 14.5 |
| 12.9 | 6.8 | 18.8 |
| 13.2 | 6.7 | 27.7 |
| 14.0 | 6.3 | 18.1 |
| 14.3 | 6.2 | 7 |
| 15.0 | 5.9 | 17.3 |
| 15.8 | 5.6 | 47.2 |
| 16.0 | 5.5 | 24.2 |
| 17.0 | 5.2 | 50.8 |
| 17.5 | 5.1 | 21.6 |
| 18.8 | 4.7 | 27.5 |
| 19.2 | 4.6 | 35.4 |
| 19.8 | 4.5 | 16.3 |
| 20.5 | 4.3 | 16 |
| 21.0 | 4.2 | 14.5 |
| 21.4 | 4.1 | 16 |
| 21.9 | 4.0 | 17 |
| 22.4 | 4.0 | 67.4 |
| 22.8 | 3.9 | 21.5 |
| 23.4 | 3.8 | 42.4 |
| 24.2 | 3.7 | 11.2 |
| 24.9 | 3.6 | 23.8 |
| 26.2 | 3.4 | 41.5 |
| 27.2 | 3.3 | 19 |
| 28.1 | 3.2 | 11.6 |
| 29.1 | 3.1 | 15 |
| 30.3 | 2.9 | 8.6 |
| 30.8 | 2.9 | 9.4 |
| 31.6 | 2.8 | 12.3 |
| 34.6 | 2.6 | 8 |

Example 14: Preparation of a Crystalline Form of a Diethanesulfonate of a Compound of Formula (I)

Step 1: Preparation of Crude Diethanesulfonate of a Compound of Formula (I)

10 g of a free base of the compound of Formula (I) was charged into a reactor, then 200 mL of ethanol (EtOH) was added. To the suspension mixture, ethanesulfonic acid (2.2 eq) was added. The resulting solid was stirred for 12 hrs at reflux then stirred for 2 hrs at 20 to 25° C. The resulting solid was filtered and then washed with 50 mL of EtOH. Filtered solids were dried in an oven at 50° C. for 18 hrs. Yield: 12 g (80%).

Step 2: Preparation of the Crystalline Form of the Diethanesulfonate of a Compound of Formula (I)

12 g of the crude diethanesulfonate of the compound of Formula (I) was charged into a reactor, then 240 mL of EtOH was added. The resulting solid was stirred for 12 hrs at reflux then stirred for 2 hrs at 20 to 25° C. The resulting solid was filtered and then washed with 60 mL of EtOH. Filtered solids were dried in an oven at 50° C. for 18 hrs. Yield: 11 g (92%).

Analysis of Characteristics

The results of PXRD analysis of the crystalline form prepared in Example 14 are shown in FIG. 28.

The peaks having a relative intensity (I/Io) of 3% or higher in the PXRD spectrum of the above crystalline form are shown in Table 18 below. For peaks having a I/Io ratio equal to or higher than 10%, the diffraction angles were 5.7°, 6.8°, 7.4°, 11.5°, 14.8°, 15.2°, 17.6°, 18.4°, 20.2°, 20.5°, 22.1°, 22.3°, 23.2°, 23.6°, 23.8°, 25.2°, 25.6°, 25.8°, 26.4°, 27.5°, 28.1° and 28.8° (2θ±0.2°).

TABLE 18

| 2θ (±0.2) | d Value (Å) | I/I$_o$ (%) |
|---|---|---|
| 5.7 | 15.4 | 14.5 |
| 6.8 | 13.0 | 59.4 |
| 7.4 | 12.0 | 100 |
| 8.9 | 9.9 | 5.8 |
| 10.9 | 8.1 | 4.3 |
| 11.5 | 7.7 | 13.7 |
| 12.8 | 6.9 | 5.1 |
| 13.4 | 6.6 | 9.1 |
| 13.8 | 6.4 | 8.6 |
| 14.8 | 6.0 | 66 |
| 15.2 | 5.8 | 25.4 |
| 16.2 | 5.5 | 9.4 |
| 16.6 | 5.3 | 5.9 |
| 16.9 | 5.2 | 4 |
| 17.6 | 5.0 | 10.5 |
| 18.4 | 4.8 | 17.1 |
| 18.7 | 4.7 | 6.8 |
| 19.1 | 4.6 | 9.3 |
| 20.2 | 4.4 | 12.5 |
| 20.5 | 4.3 | 24.3 |
| 20.9 | 4.2 | 8.3 |
| 21.3 | 4.2 | 8.1 |
| 22.1 | 4.0 | 14.8 |
| 22.3 | 4.0 | 18.1 |
| 23.2 | 3.8 | 13.5 |
| 23.6 | 3.8 | 10 |
| 23.8 | 3.7 | 10.5 |
| 24.0 | 3.7 | 8.3 |
| 24.7 | 3.6 | 6.9 |
| 25.2 | 3.5 | 15.8 |
| 25.6 | 3.5 | 18.9 |
| 25.8 | 3.4 | 12.5 |
| 26.4 | 3.4 | 17.2 |
| 26.9 | 3.3 | 5.2 |
| 27.3 | 3.3 | 6.7 |
| 27.5 | 3.2 | 11.3 |
| 28.1 | 3.2 | 10.3 |
| 28.5 | 3.1 | 9.8 |
| 28.8 | 3.1 | 12.4 |

TABLE 18-continued

| 2θ (±0.2) | d Value (Å) | I/I$_o$ (%) |
|---|---|---|
| 29.8 | 3.0 | 4.1 |
| 30.5 | 2.9 | 4.5 |
| 30.8 | 2.9 | 7.2 |
| 32.0 | 2.8 | 5.5 |
| 32.6 | 2.7 | 3.9 |
| 34.3 | 2.6 | 4.1 |
| 34.6 | 2.6 | 4.3 |
| 35.0 | 2.6 | 5.1 |
| 35.4 | 2.5 | 4.8 |
| 36.8 | 2.4 | 3.5 |
| 37.5 | 2.4 | 3.3 |
| 38.2 | 2.4 | 3.7 |
| 38.6 | 2.3 | 3.9 |
| 38.8 | 2.3 | 5.6 |
| 39.5 | 2.3 | 3.1 |

Example 15: Preparation of a Crystalline Form of a Dimethanesulfonate of a Compound of Formula (I)

Step 1: Preparation of Crude Dimethanesulfonate of a Compound of Formula (I)

3 g of a free base of the compound of Formula (I) was charged into a reactor, then 60 mL of EtOH was added. To the suspension mixture, methanesulfonic acid (2.2 eq.) was added. The resulting solid was stirred for 18 hrs at reflux then stirred for 2 hrs at 20 to 25° C. The resulting solid was filtered and then washed with 15 mL of EtOH. Filtered solids were dried in an oven at 80° C. for 18 hrs. Yield: 4.25 g (101%).

Step 2: Preparation of the Crystalline Form of the Dimethanesulfonate of a Compound of Formula (I)

3.6 g of crude dimethanesulfonate of the compound of Formula (I) was charged into a reactor, then 72 mL of EtOH was added. To the suspension mixture, methanesulfonic acid (2.0 eq.) was added. The resulting solid was stirred for 18 hrs at reflux then stirred for 2 hrs at 20 to 25° C. The resulting solid was filtered and then washed with 18 mL of EtOH. Filtered solids were dried in an oven at 80° C. for 18 hrs. Yield: 3.68 g (102%).

Analysis of Characteristics

The results of PXRD analysis of the crystalline form prepared in Example 15 are shown in FIG. 7.

The peaks having a relative intensity (I/Io) of 3% or higher in the PXRD spectrum of the above crystalline form are shown in Table 19 below. For peaks having a I/Io ratio equal to or higher than 10%, the diffraction angles were 5.6°, 7.1°, 7.6°, 11.4°, 15.1°, 15.4°, 16.6°, 18.2°, 20.4°, 21.5°, 22.3°, 22.7°, 23.1°, 24.4°, 24.9° and 25.6° (2θ±0.2°).

TABLE 19

| 2θ (±0.2) | d Value (Å) | I/I$_o$ (%) |
|---|---|---|
| 5.6 | 15.7 | 11.7 |
| 7.1 | 12.4 | 45.5 |
| 7.6 | 11.6 | 100 |
| 9.1 | 9.7 | 5.4 |
| 11.1 | 8.0 | 5.3 |
| 11.4 | 7.8 | 17.5 |
| 13.4 | 6.6 | 8.4 |
| 13.7 | 6.5 | 4.4 |
| 14.6 | 6.1 | 7.6 |
| 15.1 | 5.9 | 18.6 |
| 15.4 | 5.8 | 50.9 |
| 16.0 | 5.5 | 3.8 |
| 16.6 | 5.3 | 12.5 |
| 17.1 | 5.2 | 4.8 |
| 17.8 | 5.0 | 7.4 |
| 18.2 | 4.9 | 22.4 |
| 18.5 | 4.8 | 3.8 |

TABLE 19-continued

| 2θ (±0.2) | d Value (Å) | I/I$_o$ (%) |
|---|---|---|
| 19.0 | 4.7 | 8.4 |
| 19.8 | 4.5 | 3 |
| 20.4 | 4.4 | 12.4 |
| 21.5 | 4.1 | 20.5 |
| 22.3 | 4.0 | 11.3 |
| 22.7 | 3.9 | 11.4 |
| 23.1 | 3.9 | 21.5 |
| 23.6 | 3.8 | 4.1 |
| 24.1 | 3.7 | 6.7 |
| 24.4 | 3.6 | 18.5 |
| 24.9 | 3.6 | 17.7 |
| 25.6 | 3.5 | 17.9 |
| 26.3 | 3.4 | 8.8 |
| 26.8 | 3.3 | 3.7 |
| 27.2 | 3.3 | 4.7 |
| 28.3 | 3.2 | 4.9 |
| 28.9 | 3.1 | 5.4 |
| 29.6 | 3.0 | 9.6 |
| 30.1 | 3.0 | 3.2 |
| 30.5 | 2.9 | 4.3 |
| 31.0 | 2.9 | 4.4 |
| 32.3 | 2.8 | 3.7 |
| 32.9 | 2.7 | 4.5 |
| 33.8 | 2.7 | 4.1 |
| 34.7 | 2.6 | 4.2 |
| 34.9 | 2.6 | 3.7 |
| 36.2 | 2.5 | 3.6 |
| 37.0 | 2.4 | 4.3 |
| 38.2 | 2.4 | 3.3 |
| 38.6 | 2.3 | 3.9 |
| 39.1 | 2.3 | 3.4 |
| 39.4 | 2.3 | 3.6 |
| — | — | — |

Example 16: Preparation of a Crystalline Form of a Free Base of a Compound of Formula (I)

200.0 g of a crystalline form of a dihydrochloride salt (2HCl) of the compound of Formula (I) was charged into a reactor of 10 L, then 1.0 L of DMSO and 4.0 L of MeOH were added. The resulting suspension was heated to 55 to 60° C. to dissolve the compound of Formula (I) while stirring with a mechanical stirrer. While maintaining the temperature of the reactor at 55 to 60° C. and stirring at 200 rpm, 347 mL of DIPEA was added to the reaction mixture over 2 hrs. While maintaining the temperature of the reactor at 55 to 60° C. and with weak stirring at 50 to 60 rpm, the resulting mixture was heated and stirred for 36 hrs to form a precipitate. The reaction mixture was cooled to 20 to 25° C. and then stirred for 6 hrs. Generated precipitates were filtered and then washed with 10.0 L of MeOH. Filtered solids were dried in a vacuum oven at 40° C. for 48 hrs. Yield: 146 g (94.6%).

Analysis of Characteristics

Figure 29:
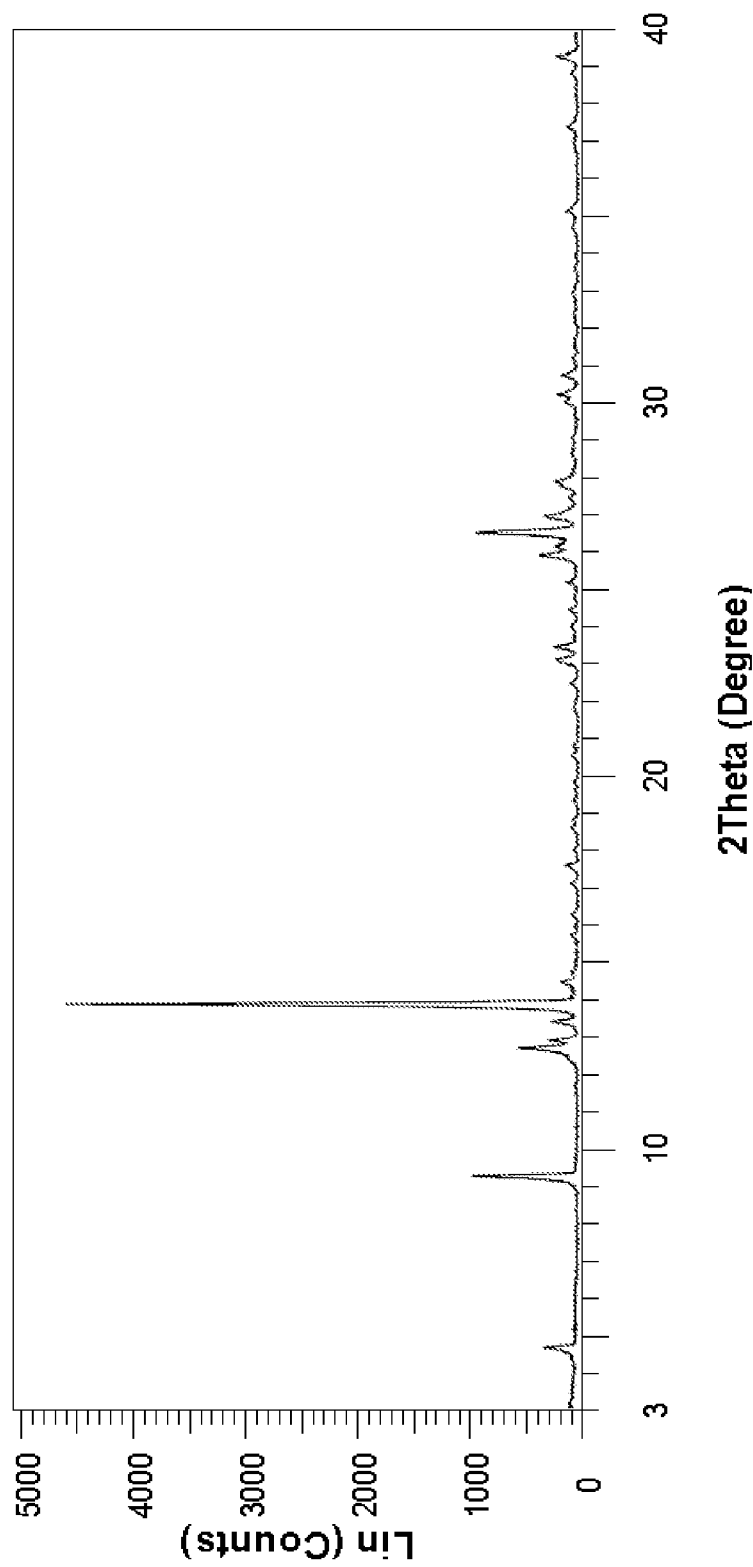
FIG. 29 shows a PXRD pattern for crystalline Formula (I) free base.

The results of PXRD analysis of the crystalline form prepared in Example 16 are shown in FIG. 29.

The peaks having a relative intensity (I/Io) of 3% or higher in the PXRD spectrum of the above crystalline form are shown in Table 20 below. For peaks having a I/Io ratio equal to or higher than 10%, the diffraction angles were 9.2°, 12.7°, 13.8° and 26.5° 2θ±0.2°).

TABLE 20

| 2θ (±0.2) | d Value (Å) | I/I$_o$ (%) |
|---|---|---|
| 4.6 | 19.1 | 7 |
| 9.2 | 9.6 | 20.9 |
| 12.7 | 7.0 | 12 |
| 12.9 | 6.9 | 5.9 |
| 13.4 | 6.6 | 5.4 |
| 13.8 | 6.4 | 100 |
| 14.4 | 6.1 | 3.7 |
| 23.1 | 3.8 | 4.5 |
| 23.4 | 3.8 | 5.1 |
| 25.9 | 3.4 | 8 |
| 26.2 | 3.4 | 4.9 |
| 26.5 | 3.4 | 20.3 |
| 27.0 | 3.3 | 6.9 |
| 27.9 | 3.2 | 4.6 |
| 30.3 | 3.0 | 4.4 |
| 30.8 | 2.9 | 3.4 |
| 39.3 | 2.3 | 4.6 |
| — | — | — |

Comparative Example 1: Preparation of an Amorphous Form of the Compound of Formula (I) Free Base An amorphous form of the compound of Formula (I) was prepared according to the method disclosed in WO 2013/100632 referenced herein.

Analysis of Characteristics

Figure 30:
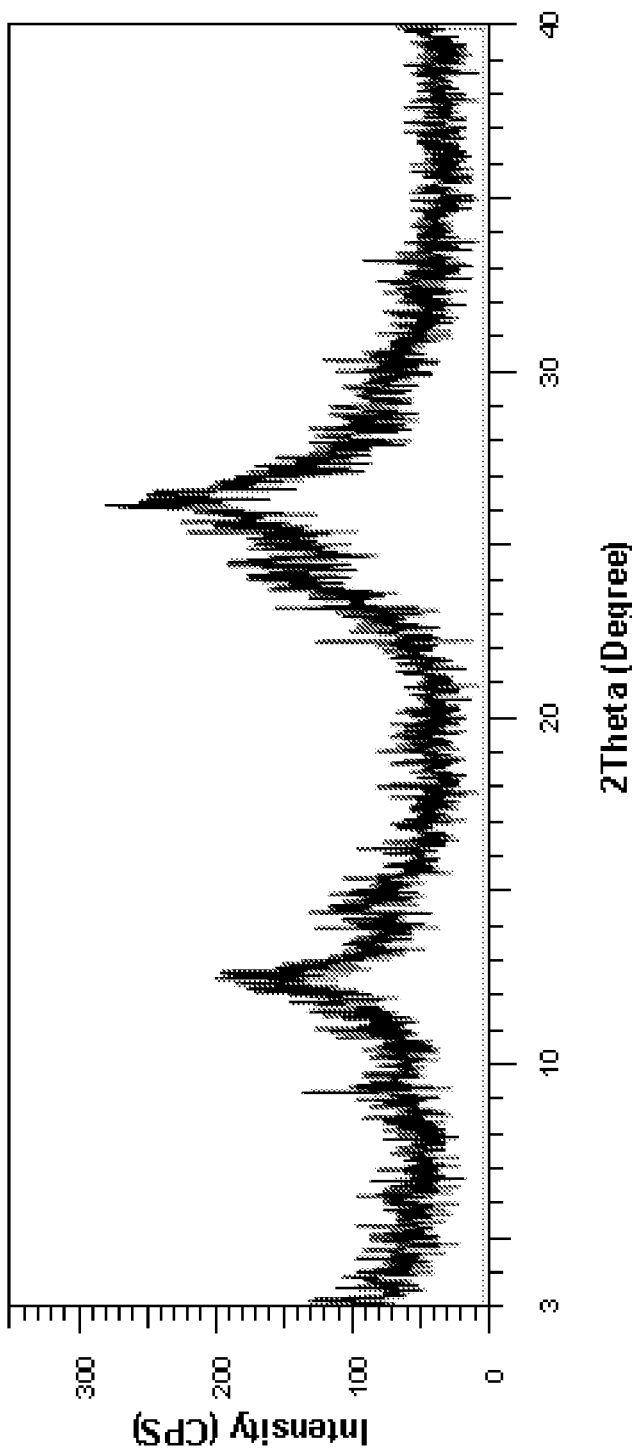
FIG. 30 shows a PXRD pattern for amorphous Formula (I) free base.

The results of PXRD analysis of the amorphous form prepared in Comparative Example 1 are shown in FIG. 30.

The amorphous form failed to show any particular diffraction pattern in an PXRD spectrum.

Comparative Example 2: Preparation of an Amorphous Form of the Compound of Formula (I) Bis-Hydrochloride 5 g of Formula (I) bis-hydrochloride salt (100.2% assay, 12.0% H$_2$O) was charged into a reactor, then 25 mL of DMSO was added. The suspension mixture was heated to 130° C. for 1.5 hrs to form a yellow clear solution. The reaction mixture was cooled to 20 to 25° C. 50 mL of acetone was dropwise for 15 mins at 20 to 25° C. to form a slurry, the resulting solid was stirred for 18 hrs at 20 to 25° C., and the slurry was then filtered and washed with 50 mL of acetone. Filtered solids were dried in a vacuum oven at 50° C. for 24 hrs. Yield: 4.26 g (85%), moisture: 5.5%, residual solvent: 12% DMSO.

Figure 31:
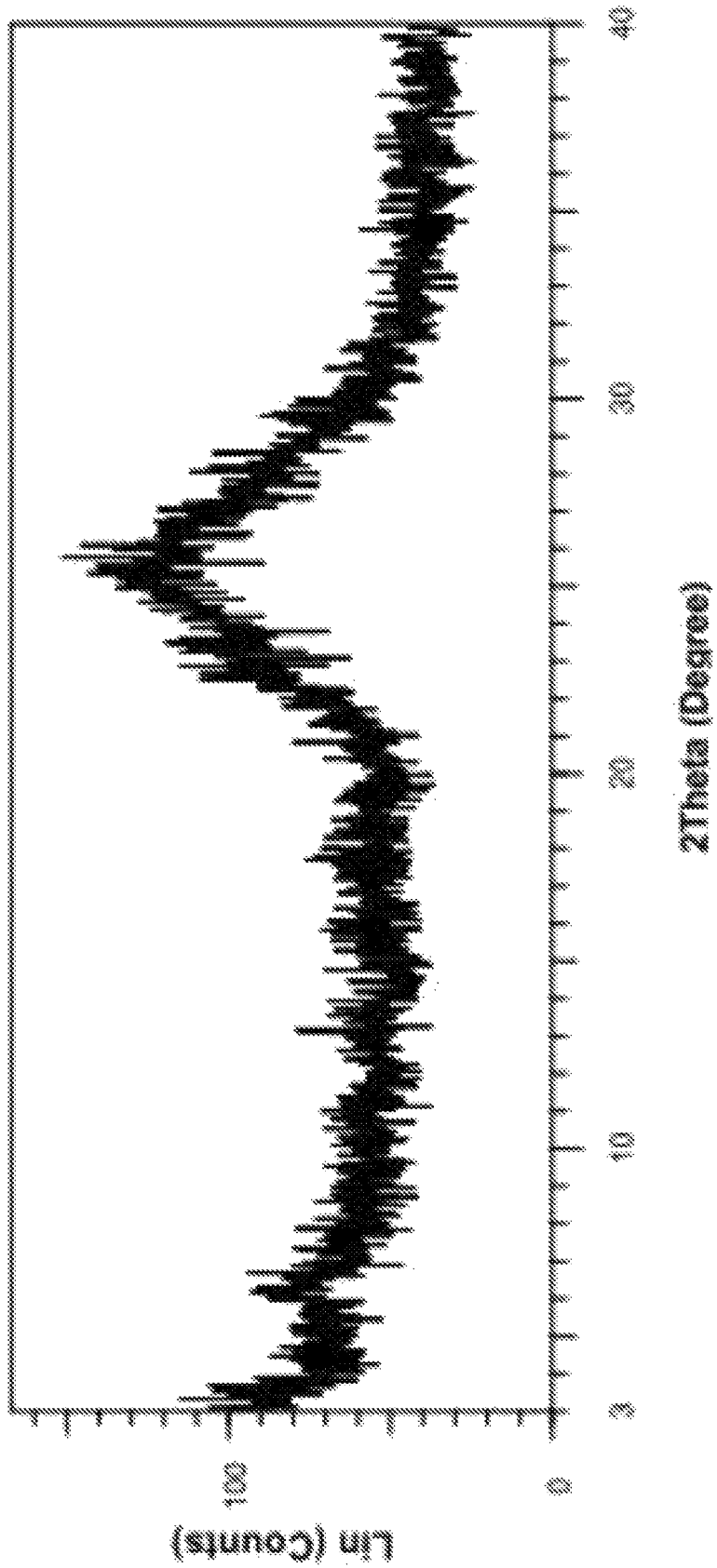
FIG. 31 shows a PXRD pattern for amorphous Formula (I) bis-hydrochloride salt.

FIG. 31 shows the PXRD pattern characterized by an absence of sharp peaks and denoting the amorphous form of Formula (I) bis-hydrochloride.

Figure 32:
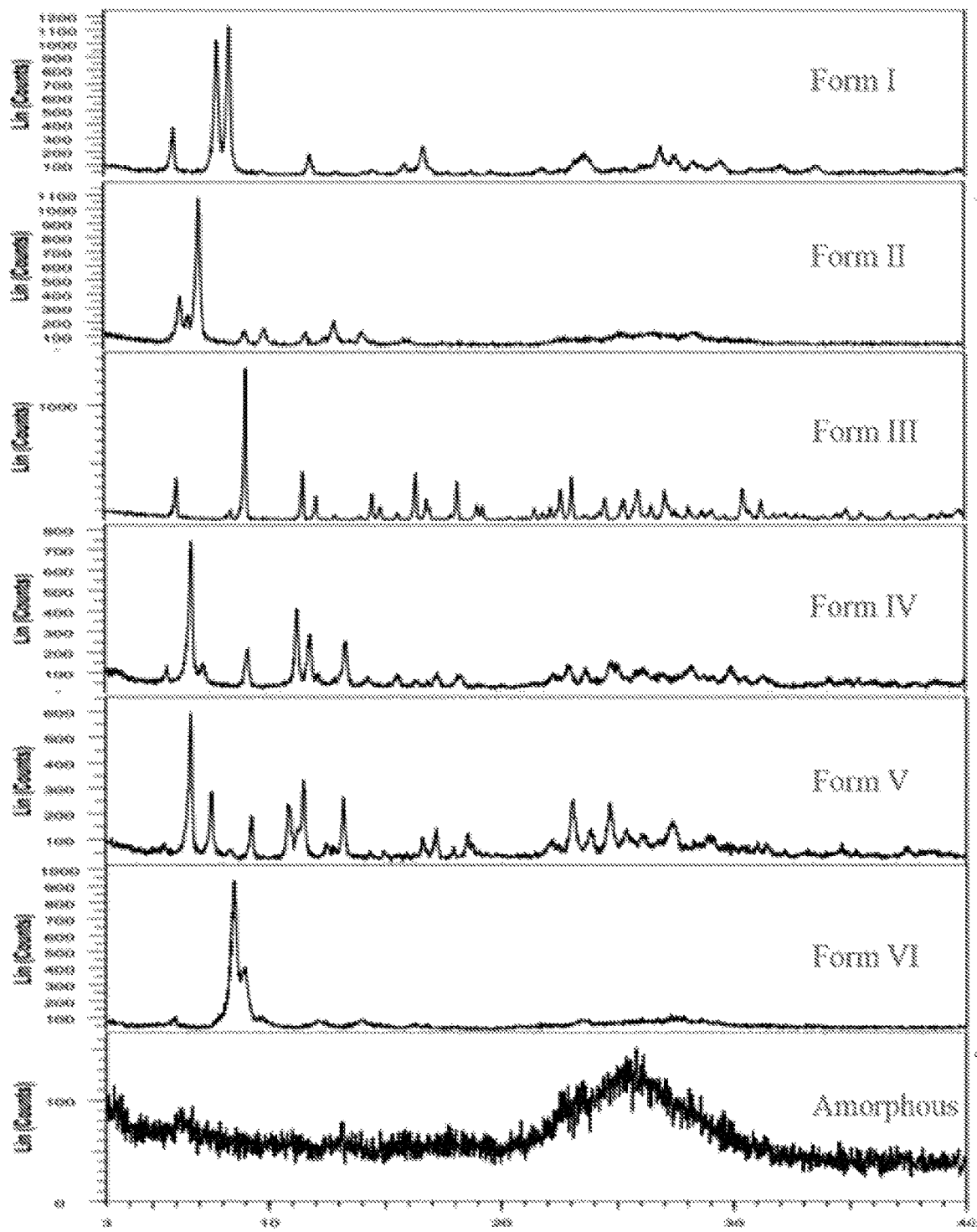
FIG. 32 shows PXRD pattern overlays for Formula (I) bis-hydrochloride salt crystalline polymorph Forms I to VI and for amorphous Formula (I) bis-hydrochloride salt.

FIG. 32 shows and overlay of PXRD patterns for Formula (I) bis-hydrochloride crystalline Forms I to VI and for amorphous Formula (I) bis-hydrochloride.

Test Example 1: Stress Stability Test

In order to compare physicochemical stability among the crystalline form prepared in Example 3 (crystalline Formula (I) bis-hydrochloride Form I) and 16 (Formula (I) crystalline free base), and the amorphous form prepared in Comparative Example 1, a stress stability test was conducted by storing samples at 60° C., for different periods of time up to 4 weeks. The results are summarized in Table 21 below.

TABLE 21

| Compound | Test items (A % by HPLC) | Initial | 1 day | 3 days | 7 days | 2 weeks | 4 weeks |
|---|---|---|---|---|---|---|---|
| Example 3 | Purity(%) | 99.8 | 99.8 | 99.8 | 99.8 | 99.8 | 99.8 |
|  | Total impurities(%) | 0.17 | 0.17 | 0.15 | 0.19 | 0.16 | 0.23 |
| Example 16 | Purity(%) | 99.7 | — | — | 99.7 | 99.7 | — |
|  | Total impurities(%) | 0.29 | — | — | 0.29 | 0.29 | — |
| Comparative Example 1 | Purity(%) | 99.7 | 99.7 | 99.7 | 99.6 | 99.5 | 99.3 |
|  | Total impurities(%) | 0.32 | 0.30 | 0.31 | 0.38 | 0.485 | 0.68 |

As shown in Table 21 above, the crystalline form of the free base and the crystalline form (Form I) of the dihydrochloride exhibited remarkably superior stability over the amorphous form. The amorphous form showed a change of purity after 7 days. Therefore, it can be seen that the crystalline forms according to the present invention show superior physicochemical stability over the amorphous form.

Figure 33:
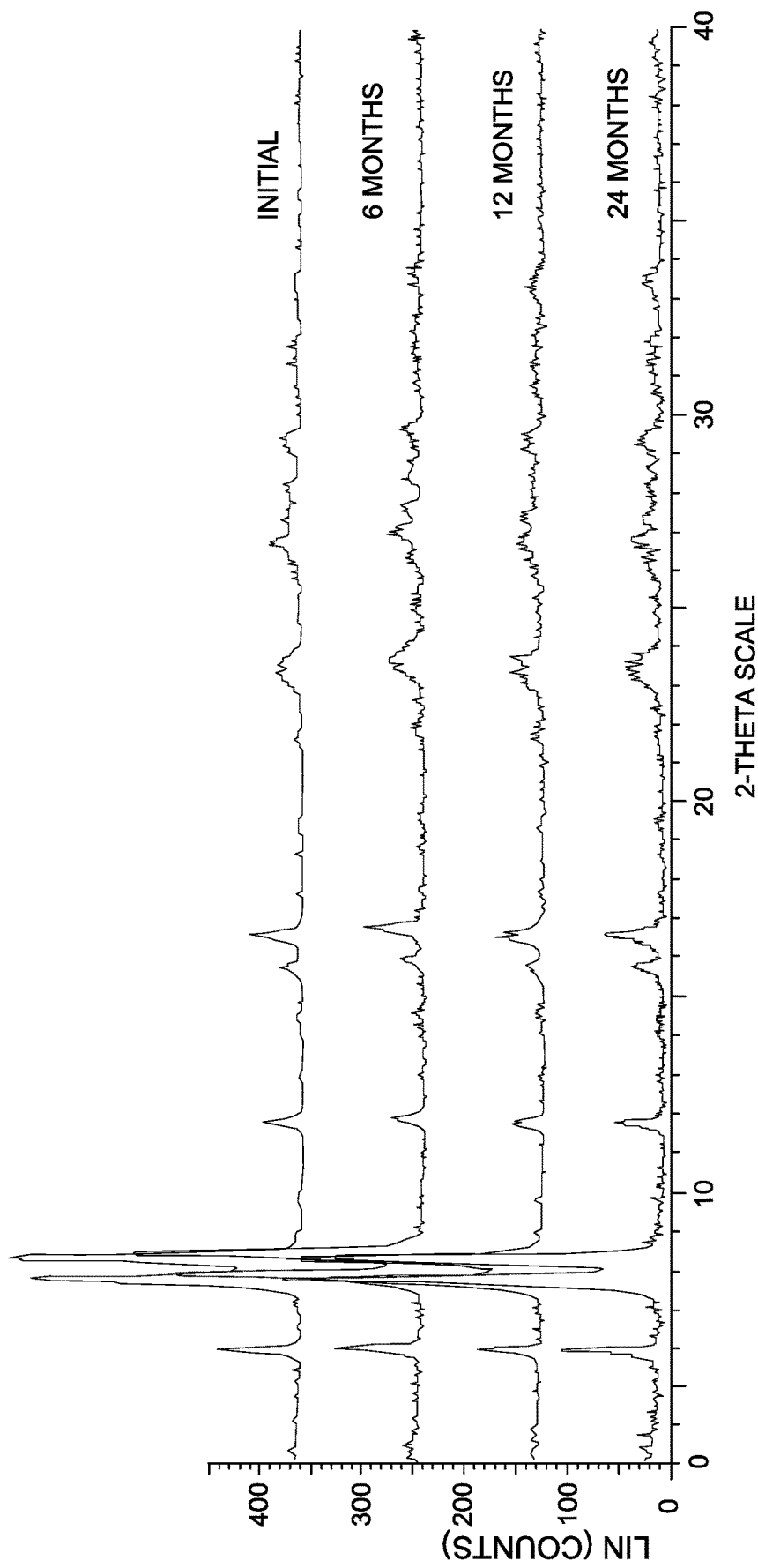
FIG. 33 shows PXRD patterns for crystalline Formula (I) bis-hydrochloride Form I at 6 months, 12 months and 24 months after exposure to conditions of 20° C. to 30° C. at 60% relative humidity and protection from light.

The stability of crystalline Formula (I) bis-hydrochloride Form I was evaluated at 3 months, 6 months, 9 months, 12 months, 18 months and 24 under conditions of 20° C. to 30° C. at 60% relative humidity and protection from light. Stability criteria included the following. At each interval from 3 to 24 months the crystalline Formula (I) bis-hydrochloride Form I appeared as a pale brown to off-white powder. Identification was performed by IR, PXRD and HPLC methods as described elsewhere herein with results reported as pass/fail. Purity was determined by HPLC with known impurities at relative retention times ("RRT") of 1.1, 1.7 and 2.1. The results are shown in Table 22 where "Init" refers to initial, "Iden" refers to identification, "Imp" refers to impurity, "A.U.I." refers to any unspecified impurity, "T.U.I." refers to total unspecified impurity, "T.I." refers to total impurities, and "N.D." refers to not detected. The PXRD results at initial, 6 months, 12 months and 24 months are depicted in FIG. 33.

The invention claimed is:

1. A compound selected from pharmaceutically acceptable salts of a compound of Formula (I), in crystalline form:

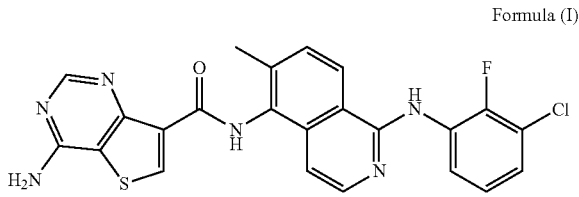 [SMILES: Cc1ccc2c(Nc3cccc(Cl)c3F)nccc2c1NC(=O)c1csc2c(N)ncnc12]

Formula (I)

wherein the salt is selected from:
a bis-hydrochloride salt polymorph Form I characterized by a powder X-ray diffraction pattern having three or more peaks selected from those at diffraction angle 2θ values of 5.89°±0.2°, 7.77°±0.2°, 8.31°±0.2°, 16.68°±0.2° and 26.89°±0.2°, when irradiated with a Cu-Kα light source; and
a bis-methanesulfonate salt characterized by a powder X-ray diffraction pattern having three or more peaks selected from those at diffraction angle 2θ values of 7.1°±0.2°, 7.6°±0.2°, 15.4°±0.2°, 18.2°±0.2°, and 23.1°±0.2°, when irradiated with a Cu-Kα light source.

2. The compound of claim 1 wherein the salt is bis-hydrochloride salt polymorph Form I characterized by a powder X-ray diffraction pattern in accordance with FIG. 35.

3. The compound of claim 1 wherein the bis-hydrochloride salt is polymorph Form I characterized by a powder X-ray diffraction pattern having three or more peaks selected from those at diffraction angle 2θ values of 5.89°±0.2°,

TABLE 22

| Test | Init | 3 mo | 6 mo | 9 mo | 12 mo | 18 mo | 24 mo |
|---|---|---|---|---|---|---|---|
| Identity |  |  |  |  |  |  |  |
| IR | pass | — | pass | — | Pass | — | — |
| PXRD | pass | — | pass | — | Pass | — | — |
| HPLC | pass | pass | pass | pass | pass | pass | pass |
| Purity |  |  |  |  |  |  |  |
| Purity | 99.9% | 99.8% | 99.8% | 99.8% | 99.8% | 99.9% | 99.8% | 99.8% |
| Imp 1 | 0.01% | 0.02% | 0.03% | 0.02% | 0.02% | 0.02% | 0.02% | 0.02% |
| Imp RRT 1.1 | N.D. | N.D. | N.D. | N.D. | N.D. | N.D. | N.D. | N.D. |
| Imp RRT 1.7 | 0.08% | 0.08% | 0.08% | 0.08% | 0.02% | 0.02% | 0.02% | 0.02% |
| Imp RRT 2.1 | N.D. | N.D. | N.D. | N.D. | N.D. | N.D. | N.D. | N.D. |
| A.U.I. | 0.04% | 0.03% | 0.03% | 0.03% | 0.06% | 0.06% | 0.06% | 0.06% |
| T.U.I | 0.05% | 0.05% | 0.05% | 0.05% | 0.09% | 0.09% | 0.11% | 0.12% |
| T.I. | 0.14% | 0.15% | 0.16% | 0.16% | 0.14% | 0.13% | 0.15% | 0.16% |

7.77°±0.2°, 8.31°±0.2°, 11.80°±0.2°, 16.68°±0.2°, 23.22°±0.2°, 23.69°±0.2°, 26.89°±0.2°, 27.51°±0.2°, and 29.53°±0.2°, when irradiated with a Cu-Kα light source.

4. The compound of claim 1 wherein the bis-hydrochloride salt is a trihydrate.

5. The compound of claim 1 wherein the salt is the bis-methanesulfonate salt characterized by a powder X-ray diffraction pattern in accordance with FIG. 7.

6. The compound of claim 1 wherein the bis-methanesulfonate salt is characterized by a powder X-ray diffraction pattern having three or more peaks selected from those at diffraction angle 2θ values of 7.1°±0.2°, 7.6°±0.2°, 15.1°±0.2°, 15.4°±0.2°, 18.2°±0.2°, 21.5°±0.2°, 23.1°±0.2°, 24.4°±0.2°, 24.9°±0.2°, and 25.6°±0.2°, when irradiated with a Cu-Kα light source.

7. A pharmaceutical composition comprising the compound of claim 1, and at least one pharmaceutically acceptable excipient.

8. The pharmaceutical composition of claim 7, wherein the Formula (I) salt is the bis-methanesulfonate salt.

9. A method for treating abnormal cell growth disease in a mammal wherein the abnormal cell growth disease is caused by abnormal activation of a RAF kinase, the method comprising administering the pharmaceutical composition of claim 7 to the mammal.

10. The method of claim 9, wherein the Formula (I) salt is the bis-methanesulfonate salt.

11. A method for preparing a crystalline salt form of a compound of Formula (I)

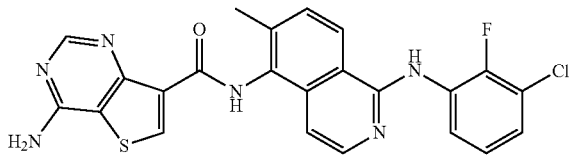

Formula (I)

the method comprising:
(a) adding an organic solvent to the free base of the compound of Formula (I) to form an admixture;
(b) adding 2 to 3 equivalents of an acid to each equivalent of Formula (I) free base in the admixture obtained in step (a) to form a slurry containing solid Formula (I) crystalline salt; and
(c) isolating the solid Formula (I) crystalline salt from the slurry,
wherein the acid is selected from the group consisting of hydrochloric acid, sulfuric acid, p-toluenesulfonic acid, ethanesulfonic acid, methanesulfonic acid, benzenesulfonic acid, and mixtures thereof.

12. The method of claim 11, wherein:
the organic solvent is ethanol;
the acid is hydrochloric acid;
the Formula (I) salt is the crystalline bis-hydrochloride salt;
the method further comprises isolating solid crystalline Formula (I) bis-hydrochloride salt from the slurry; and
the method further comprises drying the isolated crystalline Formula (I) bis-hydrochloride salt,
wherein the dried crystalline Formula (I) bis-hydrochloride salt is exposed to air comprising water vapor, and the resulting polymorph is the Form I polymorph.

13. A pharmaceutically acceptable bis-hydrochloride salt of a compound of Formula (I), in crystalline form:

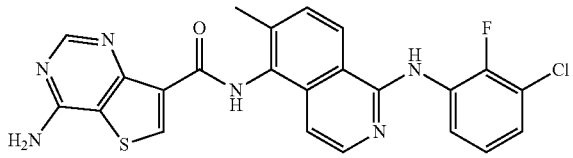

Formula (I)

wherein the bis-hydrochloride salt is polymorph Form I characterized by a powder X-ray diffraction pattern having three or more peaks selected from those at diffraction angle 2θ values of 5.89°±0.2°, 7.77°±0.2°, 8.31°±0.2°, 11.80°±0.2°, 16.68°±0.2°, 23.22°±0.2°, 23.69°±0.2°, 26.89°±0.2°, 27.51°±0.2°, and 29.53°±0.2°, when irradiated with a Cu-Kα light source.

14. The compound of claim 13 wherein the bis-hydrochloride salt is polymorph Form I characterized by a powder X-ray diffraction pattern in accordance with FIG. 35.

15. A pharmaceutically acceptable bis-methanesulfonate salt of a compound of Formula (I), in crystalline form:

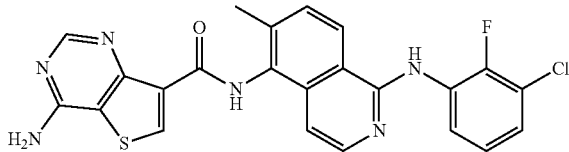

Formula (I)

wherein the bis-methanesulfonate salt is characterized by a powder X-ray diffraction pattern having three or more peaks selected from those at diffraction angle 2θ values of 7.1°±0.2°, 7.6°±0.2°, 15.1°±0.2°, 15.4°±0.2°, 18.2°±0.2°, 21.5°±0.2°, 23.1°±0.2°, 24.4°±0.2°, 24.9°±0.2°, and 25.6°±0.2°, when irradiated with a Cu-Kα light source.

16. The compound of claim 15 wherein the bis-methanesulfonate salt is characterized by a powder X-ray diffraction pattern in accordance with FIG. 7.

17. A salt of a compound of Formula (I), wherein the salt is selected from the group consisting of a hydrochloride salt, a hydrogensulfate salt, a p-toluenesulfonate salt, an ethanesulfonate salt and a methanesulfonate salt:

Formula (I)

wherein the salt is in the amorphous form.

18. The compound of claim 17 wherein the salt is selected from the bis-hydrochloride salt, the bis-hydrogensulfate salt, the bis-p-toluenesulfonate salt, the bis-ethanesulfonate salt, and the bis-methanesulfonate salt.

19. The salt of a compound of Formula (I) of claim 17, wherein the Formula (I) salt is the bis-methanesulfonate salt.

* * * * *

UNITED STATES PATENT AND TRADEMARK OFFICE
CERTIFICATE OF CORRECTION

PATENT NO. : 11,649,246 B2
APPLICATION NO. : 16/768535
DATED : May 16, 2023
INVENTOR(S) : Chang Hee Park et al.

It is certified that error appears in the above-identified patent and that said Letters Patent is hereby corrected as shown below:

On the Title Page

In item (54), in Title, delete "SALTS OF 4-AMINO-N-(L-((3-CHLORO-2-FLUOROPHENYL)AMINO)-6-METHYLISOQUINOLIN-5-YL)THIENO[3,2-D]PYRIMIDINE-7-CARBOXAMIDE, AND CRYSTALLINE FORMS THEREOF" and insert therefor -- SALTS OF 4-AMINO-N-(1-((3-CHLORO-2-FLUOROPHENYL)AMINO)-6-METHYLISOQUINOLIN-5-YL)THIENO[3,2-D]PYRIMIDINE-7-CARBOXAMIDE, AND CRYSTALLINE FORMS THEREOF --.

In the Specification

Column 1, Lines 1-5, delete "SALTS OF 4-AMINO-N-(L-((3-CHLORO-2-FLUOROPHENYL)AMINO)-6-METHYLISOQUINOLIN-5-YL)THIENO[3,2-D]PYRIMIDINE-7-CARBOXAMIDE, AND CRYSTALLINE FORMS THEREOF" and insert therefor -- SALTS OF 4-AMINO-N-(1-((3-CHLORO-2-FLUOROPHENYL)AMINO)-6-METHYLISOQUINOLIN-5-YL)THIENO[3,2-D]PYRIMIDINE-7-CARBOXAMIDE, AND CRYSTALLINE FORMS THEREOF --.

Signed and Sealed this
Seventeenth Day of October, 2023

Katherine Kelly Vidal
*Director of the United States Patent and Trademark Office*